US009684165B2

(12) United States Patent
Border

(10) Patent No.: US 9,684,165 B2
(45) Date of Patent: Jun. 20, 2017

(54) EYE IMAGING IN HEAD WORN COMPUTING

(71) Applicant: Osterhout Group, Inc., San Francisco, CA (US)

(72) Inventor: John N. Border, Eaton, NH (US)

(73) Assignee: Osterhout Group, Inc., San Francisco, CA (US)

( * ) Notice: Subject to any disclaimer, the term of this patent is extended or adjusted under 35 U.S.C. 154(b) by 0 days.

(21) Appl. No.: 14/524,813

(22) Filed: Oct. 27, 2014

(65) Prior Publication Data

US 2015/0205101 A1 Jul. 23, 2015

Related U.S. Application Data

(63) Continuation of application No. 14/216,175, filed on Mar. 17, 2014, now Pat. No. 9,298,007, which is a (Continued)

(51) Int. Cl.
*A61B 3/14* (2006.01)
*G02B 27/14* (2006.01)
(Continued)

(52) U.S. Cl.
CPC .......... *G02B 27/0093* (2013.01); *A61B 3/145* (2013.01); *G02B 27/01* (2013.01); *G02B 27/017* (2013.01); *G02B 27/0172* (2013.01); *G06F 1/163* (2013.01); *G06F 3/005* (2013.01); *G06F 3/013* (2013.01); *G06K 9/00604* (2013.01); *H04N 5/33* (2013.01); *G02B 27/14* (2013.01);
(Continued)

(58) Field of Classification Search
CPC G02B 27/0093; G02B 27/01; G02B 27/0101; G02B 27/017; G02B 27/0172; G02B 2027/0138; G02B 2027/0178; G06F 1/163; G06F 3/01; G06F 3/013; H04N 7/144; H04N 7/147; A61B 3/10; A61B 3/14; A61B 3/152; A61B 3/156; G09G 5/00
USPC ......... 359/630–634, 636; 345/7–9, 156, 207, 345/419, 420, 633; 348/36, 47, 78; 351/41, 158, 205–207, 209, 210, 215
See application file for complete search history.

(56) References Cited

U.S. PATENT DOCUMENTS 3,305,294 A 2/1967 Alvarez
4,034,401 A 7/1977 Mann
(Continued)

FOREIGN PATENT DOCUMENTS

EP 368898 A1 5/1990
EP 777867 A1 6/1997
(Continued)

OTHER PUBLICATIONS

US 9,195,056, 11/2015, Border et al. (withdrawn)
(Continued)

*Primary Examiner* — Loha Ben
(74) *Attorney, Agent, or Firm* — GTC Law Group PC & Affiliates

(57) ABSTRACT

Aspects of the present invention relate to methods and systems for imaging, recognizing, and tracking of a user's eye that is wearing a HWC. Aspects further relate to the processing of images reflected from the user's eye and controlling displayed content in accordance therewith.

7 Claims, 61 Drawing Sheets

Related U.S. Application Data continuation-in-part of application No. 14/160,377, filed on Jan. 21, 2014, and a continuation-in-part of application No. 14/172,901, filed on Feb. 4, 2014, which is a continuation-in-part of application No. 14/163,646, filed on Jan. 24, 2014, now Pat. No. 9,400,390, which is a continuation-in-part of application No. 14/160,377, filed on Jan. 21, 2014, said application No. 14/216,175 is a continuation-in-part of application No. 14/181,459, filed on Feb. 14, 2014, which is a continuation-in-part of application No. 14/178,047, filed on Feb. 11, 2014, now Pat. No. 9,229,233, which is a continuation-in-part of application No. 14/172,901, filed on Feb. 4, 2014, which is a continuation-in-part of application No. 14/163,646, filed on Jan. 24, 2014, now Pat. No. 9,400,390, which is a continuation-in-part of application No. 14/160,377, filed on Jan. 21, 2014.

(51) Int. Cl.
| | |
|---|---|
| *G09G 5/00* | (2006.01) |
| *G02B 27/00* | (2006.01) |
| *G06K 9/00* | (2006.01) |
| *G02B 27/01* | (2006.01) |
| *H04N 5/33* | (2006.01) |
| *G06F 1/16* | (2006.01) |
| *G06F 3/00* | (2006.01) |
| *G06F 3/01* | (2006.01) |
| *H04N 7/14* | (2006.01) |
| *H04N 7/18* | (2006.01) |

(52) U.S. Cl.
CPC ............ *G02B 2027/0138* (2013.01); *G02B 2027/0178* (2013.01); *G02B 2027/0198* (2013.01); *G06F 1/1686* (2013.01); *G09G 5/00* (2013.01); *H04N 7/144* (2013.01); *H04N 7/185* (2013.01)

(56) References Cited

U.S. PATENT DOCUMENTS

| | | | |
|---|---|---|---|
| 4,668,155 | A | 5/1987 | Kaufmann et al. |
| 4,852,988 | A | 8/1989 | Velez et al. |
| 4,928,301 | A | 5/1990 | Smoot et al. |
| D327,674 | S | 7/1992 | Kuo |
| 5,151,722 | A | 9/1992 | Massof et al. |
| 5,257,094 | A | 10/1993 | LaRussa et al. |
| D352,930 | S | 11/1994 | Tsuji |
| D375,748 | S | 11/1996 | Hartman |
| D376,790 | S | 12/1996 | Goulet et al. |
| 5,621,424 | A | 4/1997 | Shimada et al. |
| 5,699,057 | A | 12/1997 | Ikeda et al. |
| 5,699,194 | A | 12/1997 | Takahashi |
| 5,717,422 | A | 2/1998 | Fergason et al. |
| D392,959 | S | 3/1998 | Edwards |
| 5,729,242 | A | 3/1998 | Margerum et al. |
| 5,767,841 | A | 6/1998 | Hartman |
| 5,788,195 | A | 8/1998 | Rice |
| D410,638 | S | 6/1999 | Sheehan et al. |
| 5,914,818 | A | 6/1999 | Tejada et al. |
| 5,949,583 | A | 9/1999 | Rallison et al. |
| 5,991,084 | A | 11/1999 | Hildebrand et al. |
| 6,028,608 | A | 2/2000 | Jenkins |
| 6,034,653 | A | 3/2000 | Robertson et al. |
| 6,046,712 | A | 4/2000 | Beller et al. |
| 6,160,552 | A | 12/2000 | Wilsher et al. |
| 6,222,677 | B1 | 4/2001 | Budd |
| 6,297,749 | B1 | 10/2001 | Smith et al. |
| D451,892 | S | 12/2001 | Carrere |
| 6,347,764 | B1 | 2/2002 | Brandon et al. |
| 6,384,982 | B1 | 5/2002 | Spitzer |
| 6,456,438 | B1 | 9/2002 | Lee et al. |
| 6,461,000 | B1 | 10/2002 | Magarill |
| 6,478,429 | B1 | 11/2002 | Aritake et al. |
| 6,480,174 | B1 | 11/2002 | Kaufmann et al. |
| 6,491,389 | B2 | 12/2002 | Yaguchi et al. |
| D470,144 | S | 2/2003 | Li |
| 6,535,182 | B2 | 3/2003 | Stanton |
| D473,871 | S | 4/2003 | Santos |
| 6,563,626 | B1 | 5/2003 | Iwasaki et al. |
| D478,052 | S | 8/2003 | Thomas |
| 6,642,945 | B1 | 11/2003 | Sharpe et al. |
| 6,747,611 | B1 | 6/2004 | Budd et al. |
| 6,795,041 | B2 | 9/2004 | Ogawa et al. |
| 6,847,336 | B1 | 1/2005 | Lemelson et al. |
| 6,906,836 | B2 | 6/2005 | Parker et al. |
| D512,027 | S | 11/2005 | Sarasjoki et al. |
| D513,233 | S | 12/2005 | Stauffer |
| 6,987,787 | B1 | 1/2006 | Mick |
| D514,525 | S | 2/2006 | Stauffer |
| 7,003,308 | B1 | 2/2006 | Fuoss et al. |
| 7,016,116 | B2 | 3/2006 | Dolgoff et al. |
| 7,030,925 | B1 | 4/2006 | Tsunekawa et al. |
| D521,493 | S | 5/2006 | Wai |
| 7,088,234 | B2 | 8/2006 | Naito et al. |
| D529,467 | S | 10/2006 | Rose |
| D541,226 | S | 4/2007 | Wakisaka et al. |
| 7,199,934 | B2 | 4/2007 | Yamasaki |
| D559,793 | S | 1/2008 | Fan |
| D571,816 | S | 6/2008 | Corcoran et al. |
| 7,414,791 | B2 | 8/2008 | Urakawa et al. |
| 7,417,617 | B2 | 8/2008 | Eichenlaub |
| 7,457,040 | B2 | 11/2008 | Amitai |
| 7,522,344 | B1 | 4/2009 | Curatu et al. |
| 7,542,210 | B2 * | 6/2009 | Chirieleison, Sr. G02B 27/0093 345/8 |
| 7,543,943 | B1 | 6/2009 | Hubby et al. |
| 7,646,540 | B2 | 1/2010 | Dolgoff et al. |
| 7,690,799 | B2 | 4/2010 | Nestorovic et al. |
| 7,728,799 | B2 | 6/2010 | Kerr et al. |
| 7,777,690 | B2 | 8/2010 | Winsor et al. |
| 7,777,723 | B2 | 8/2010 | Namiki et al. |
| 7,777,960 | B2 | 8/2010 | Freeman |
| 7,812,842 | B2 | 10/2010 | Gordon |
| 7,830,370 | B2 | 11/2010 | Yamazaki et al. |
| 7,850,301 | B2 | 12/2010 | DiChiara et al. |
| 7,855,743 | B2 | 12/2010 | Sako et al. |
| D631,881 | S | 2/2011 | Quinn et al. |
| D631,882 | S | 2/2011 | Odgers |
| 7,928,926 | B2 | 4/2011 | Yamamoto et al. |
| 8,004,765 | B2 | 8/2011 | Amitai |
| 8,018,579 | B1 | 9/2011 | Krah et al. |
| 8,092,007 | B2 | 1/2012 | DiChiara |
| 8,166,421 | B2 | 4/2012 | Magal et al. |
| 8,212,859 | B2 | 7/2012 | Tang et al. |
| 8,228,315 | B1 | 7/2012 | Starner et al. |
| 8,235,529 | B1 | 8/2012 | Raffle et al. |
| 8,246,170 | B2 | 8/2012 | Yamamoto et al. |
| 8,376,548 | B2 | 2/2013 | Schultz |
| 8,378,924 | B2 | 2/2013 | Jacobsen et al. |
| D680,112 | S | 4/2013 | Monahan |
| 8,427,396 | B1 | 4/2013 | Kim |
| 8,487,838 | B2 * | 7/2013 | Lewis .................. A61B 3/113 345/8 |
| 8,489,326 | B1 | 7/2013 | Na et al. |
| 8,494,215 | B2 | 7/2013 | Kimchi et al. |
| 8,505,430 | B2 | 8/2013 | Andryukov et al. |
| D689,862 | S | 9/2013 | Liu |
| 8,531,394 | B2 * | 9/2013 | Maltz .................... G02B 7/287 345/156 |
| D690,684 | S | 10/2013 | Lee et al. |
| 8,553,910 | B1 | 10/2013 | Dong et al. |
| 8,564,883 | B2 | 10/2013 | Totani et al. |
| 8,570,273 | B1 | 10/2013 | Smith |
| 8,570,656 | B1 | 10/2013 | Weissman et al. |
| 8,576,276 | B2 | 11/2013 | Bar-Zeev et al. |
| 8,576,491 | B2 | 11/2013 | Takagi et al. |
| 8,587,869 | B2 | 11/2013 | Totani et al. |
| 8,593,795 | B1 | 11/2013 | Chi et al. |
| 8,594,467 | B2 | 11/2013 | Lu et al. |

(56) References Cited

U.S. PATENT DOCUMENTS

| | | |
|---|---|---|
| 8,611,015 B2 | 12/2013 | Wheeler et al. |
| 8,662,686 B2 | 3/2014 | Takagi et al. |
| 8,670,183 B2 | 3/2014 | Clavin et al. |
| 8,678,581 B2 | 3/2014 | Blum et al. |
| 8,698,157 B2 | 4/2014 | Hanamura |
| 8,711,487 B2 | 4/2014 | Takeda et al. |
| 8,730,129 B2 * | 5/2014 | Solomon ............... G02B 26/105 345/32 |
| 8,743,052 B1 | 6/2014 | Keller et al. |
| 8,745,058 B1 | 6/2014 | Garcia-Barrio |
| 8,750,541 B1 | 6/2014 | Dong et al. |
| 8,752,963 B2 | 6/2014 | McCulloch et al. |
| 8,760,765 B2 | 6/2014 | Gupta et al. |
| 8,767,306 B1 | 7/2014 | Miao et al. |
| 8,786,675 B2 | 7/2014 | Deering et al. |
| 8,786,686 B1 | 7/2014 | Amirparviz |
| 8,787,006 B2 | 7/2014 | Golko et al. |
| 8,803,867 B2 | 8/2014 | Oikawa |
| 8,814,691 B2 | 8/2014 | Osterhout et al. |
| 8,823,071 B2 | 9/2014 | Oyamada |
| 8,824,779 B1 | 9/2014 | Smyth |
| 8,832,557 B2 | 9/2014 | Tang et al. |
| 8,836,768 B1 | 9/2014 | Zuccarino et al. |
| 8,837,880 B2 | 9/2014 | Takeda et al. |
| 8,854,433 B1 | 10/2014 | Rafii |
| 8,866,702 B1 | 10/2014 | Mirov et al. |
| 8,867,139 B2 | 10/2014 | Gupta |
| D716,813 S | 11/2014 | Deng |
| 8,878,749 B1 | 11/2014 | Wu et al. |
| D719,568 S | 12/2014 | Heinrich et al. |
| D719,569 S | 12/2014 | Heinrich et al. |
| D719,570 S | 12/2014 | Heinrich et al. |
| 8,922,530 B2 | 12/2014 | Pance |
| 8,947,323 B1 | 2/2015 | Geiss et al. |
| 8,955,973 B2 | 2/2015 | Raffle et al. |
| 8,964,298 B2 | 2/2015 | Haddick et al. |
| D724,083 S | 3/2015 | Olsson et al. |
| 8,971,023 B2 | 3/2015 | Olsson et al. |
| 8,982,014 B2 * | 3/2015 | Evans ............... G02B 27/017 345/7 |
| 8,982,471 B1 | 3/2015 | Starner et al. |
| D727,317 S | 4/2015 | Olsson et al. |
| 9,020,832 B2 | 4/2015 | Fisher et al. |
| D728,573 S | 5/2015 | Deng |
| 9,024,842 B1 | 5/2015 | Wheeler et al. |
| 9,031,273 B2 | 5/2015 | Dong et al. |
| 9,033,502 B2 | 5/2015 | Schmidt et al. |
| D732,025 S | 6/2015 | Heinrich et al. |
| 9,046,999 B1 | 6/2015 | King et al. |
| 9,063,563 B1 | 6/2015 | Gray et al. |
| D733,709 S | 7/2015 | Kawai |
| 9,076,368 B2 | 7/2015 | Evans et al. |
| 9,096,920 B1 | 8/2015 | Gomez |
| 9,107,622 B2 | 8/2015 | Nistico et al. |
| 9,116,337 B1 | 8/2015 | Miao |
| D738,373 S | 9/2015 | Davies et al. |
| 9,122,054 B2 | 9/2015 | Osterhout et al. |
| 9,128,281 B2 | 9/2015 | Osterhout et al. |
| 9,129,157 B2 | 9/2015 | Chao et al. |
| 9,129,295 B2 | 9/2015 | Border et al. |
| 9,143,693 B1 | 9/2015 | Zhou et al. |
| 9,158,115 B1 | 10/2015 | Worley et al. |
| 9,158,116 B1 | 10/2015 | Osterhout et al. |
| D743,963 S | 11/2015 | Osterhout |
| 9,176,582 B1 | 11/2015 | Johnson et al. |
| 9,229,233 B2 | 1/2016 | Osterhout et al. |
| 9,229,234 B2 | 1/2016 | Osterhout |
| D751,552 S | 3/2016 | Osterhout |
| 9,286,728 B2 | 3/2016 | Osterhout et al. |
| 9,298,001 B2 | 3/2016 | Border et al. |
| 9,298,002 B2 | 3/2016 | Border et al. |
| 9,298,007 B2 | 3/2016 | Border |
| 9,299,194 B2 | 3/2016 | Border et al. |
| D753,114 S | 4/2016 | Osterhout |
| 9,310,610 B2 | 4/2016 | Border |
| 9,316,833 B2 | 4/2016 | Border et al. |
| 9,329,387 B2 | 5/2016 | Border et al. |
| 2001/0019240 A1 | 9/2001 | Takahashi et al. |
| 2001/0050817 A1 | 12/2001 | Travers et al. |
| 2002/0005108 A1 | 1/2002 | Ludwig et al. |
| 2002/0109903 A1 | 8/2002 | Kaeriyama et al. |
| 2002/0148655 A1 | 10/2002 | Cho et al. |
| 2002/0149545 A1 | 10/2002 | Hanayama et al. |
| 2002/0183101 A1 | 12/2002 | Oh et al. |
| 2002/0191297 A1 | 12/2002 | Gleckman et al. |
| 2003/0030912 A1 | 2/2003 | Gleckman et al. |
| 2003/0151834 A1 | 8/2003 | Penn et al. |
| 2003/0209953 A1 | 11/2003 | Park et al. |
| 2003/0234823 A1 | 12/2003 | Sato et al. |
| 2004/0024287 A1 | 2/2004 | Patton et al. |
| 2004/0027312 A1 | 2/2004 | Owada et al. |
| 2004/0032392 A1 | 2/2004 | Chi et al. |
| 2004/0066363 A1 | 4/2004 | Yamano et al. |
| 2004/0066547 A1 | 4/2004 | Parker et al. |
| 2004/0130522 A1 | 7/2004 | Lin et al. |
| 2004/0150631 A1 | 8/2004 | Fleck et al. |
| 2004/0194880 A1 | 10/2004 | Jiang et al. |
| 2004/0227994 A1 | 11/2004 | Ma et al. |
| 2005/0041289 A1 | 2/2005 | Berman et al. |
| 2005/0156915 A1 | 7/2005 | Fisher et al. |
| 2005/0212980 A1 | 9/2005 | Miyazaki et al. |
| 2006/0047386 A1 | 3/2006 | Kanevsky et al. |
| 2006/0050146 A1 | 3/2006 | Richardson et al. |
| 2006/0061542 A1 | 3/2006 | Stokic et al. |
| 2006/0092131 A1 | 5/2006 | Kuroki et al. |
| 2006/0098293 A1 | 5/2006 | Garoutte et al. |
| 2006/0119794 A1 | 6/2006 | Hillis et al. |
| 2006/0132457 A1 | 6/2006 | Rimas-Ribikauskas et al. |
| 2006/0132924 A1 | 6/2006 | Mimran et al. |
| 2006/0170652 A1 | 8/2006 | Bannai et al. |
| 2006/0173351 A1 | 8/2006 | Marcotte et al. |
| 2006/0224238 A1 | 10/2006 | Azar et al. |
| 2006/0250322 A1 | 11/2006 | Hall et al. |
| 2006/0288233 A1 | 12/2006 | Kozlay et al. |
| 2007/0003168 A1 | 1/2007 | Oliver et al. |
| 2007/0004451 A1 | 1/2007 | C. et al. |
| 2007/0024750 A1 | 2/2007 | Wing Chung et al. |
| 2007/0024763 A1 | 2/2007 | Chung et al. |
| 2007/0024764 A1 | 2/2007 | Chung et al. |
| 2007/0024820 A1 | 2/2007 | Chung et al. |
| 2007/0024823 A1 | 2/2007 | Chung et al. |
| 2007/0025273 A1 | 2/2007 | Chung et al. |
| 2007/0030456 A1 | 2/2007 | Duncan et al. |
| 2007/0035563 A1 | 2/2007 | Biocca et al. |
| 2007/0038960 A1 | 2/2007 | Rekimoto et al. |
| 2007/0058868 A1 | 3/2007 | Seino et al. |
| 2007/0100637 A1 | 5/2007 | McCune et al. |
| 2007/0120836 A1 | 5/2007 | Yamaguchi et al. |
| 2007/0132662 A1 | 6/2007 | Morita et al. |
| 2007/0178950 A1 | 8/2007 | Lewis et al. |
| 2007/0233376 A1 | 10/2007 | Gershony et al. |
| 2007/0263174 A1 | 11/2007 | Shyu et al. |
| 2007/0273611 A1 | 11/2007 | Torch |
| 2008/0005702 A1 | 1/2008 | Skourup et al. |
| 2008/0066973 A1 | 3/2008 | Furuki et al. |
| 2008/0121441 A1 | 5/2008 | Sheets et al. |
| 2008/0186255 A1 | 8/2008 | Cohen et al. |
| 2008/0191965 A1 | 8/2008 | Pandozy et al. |
| 2008/0219025 A1 | 9/2008 | Spitzer et al. |
| 2008/0266645 A1 | 10/2008 | Dharmatilleke et al. |
| 2008/0291277 A1 | 11/2008 | Jacobsen et al. |
| 2009/0015735 A1 | 1/2009 | Simmonds et al. |
| 2009/0040296 A1 | 2/2009 | Moscato et al. |
| 2009/0108837 A1 | 4/2009 | Johansson et al. |
| 2009/0110241 A1 | 4/2009 | Takemoto et al. |
| 2009/0183929 A1 | 7/2009 | Zhang et al. |
| 2009/0251441 A1 | 10/2009 | Edgecomb et al. |
| 2009/0279180 A1 | 11/2009 | Amitai et al. |
| 2010/0007852 A1 | 1/2010 | Bietry et al. |
| 2010/0046075 A1 | 2/2010 | Powell et al. |
| 2010/0056274 A1 | 3/2010 | Uusitalo et al. |
| 2010/0060713 A1 | 3/2010 | Snyder et al. |
| 2010/0079508 A1 | 4/2010 | Hodge et al. |
| 2010/0085325 A1 | 4/2010 | King-Smith et al. |

(56) References Cited

U.S. PATENT DOCUMENTS

| | | |
|---|---|---|
| 2010/0094161 A1 | 4/2010 | Kiderman et al. |
| 2010/0097580 A1 | 4/2010 | Yamamoto et al. |
| 2010/0103075 A1 | 4/2010 | Kalaboukis et al. |
| 2010/0130140 A1 | 5/2010 | Waku et al. |
| 2010/0149073 A1 | 6/2010 | Chaum et al. |
| 2010/0178101 A1 | 7/2010 | Day et al. |
| 2010/0194682 A1 | 8/2010 | Orr et al. |
| 2010/0240988 A1 | 9/2010 | Varga et al. |
| 2010/0254017 A1 | 10/2010 | Martins et al. |
| 2010/0283774 A1 | 11/2010 | Bovet et al. |
| 2010/0290127 A1 | 11/2010 | Kessler et al. |
| 2011/0006982 A1 | 1/2011 | Rhee et al. |
| 2011/0007081 A1 | 1/2011 | Gordon et al. |
| 2011/0012874 A1 | 1/2011 | Kurozuka et al. |
| 2011/0089325 A1 | 4/2011 | Ottney |
| 2011/0096100 A1 | 4/2011 | Sprague et al. |
| 2011/0102234 A1 | 5/2011 | Adams et al. |
| 2011/0130958 A1 | 6/2011 | Stahl et al. |
| 2011/0131495 A1 | 6/2011 | Bull et al. |
| 2011/0157236 A1 | 6/2011 | Inoue et al. |
| 2011/0164047 A1 | 7/2011 | Pance et al. |
| 2011/0164163 A1 | 7/2011 | Bilbrey et al. |
| 2011/0164221 A1 | 7/2011 | Tilleman et al. |
| 2011/0176106 A1 | 7/2011 | Lewkowski et al. |
| 2011/0196610 A1 | 8/2011 | Waldman et al. |
| 2011/0199171 A1 | 8/2011 | Prest et al. |
| 2011/0201213 A1 | 8/2011 | Dabov et al. |
| 2011/0202823 A1 | 8/2011 | Berger et al. |
| 2011/0213664 A1 | 9/2011 | Osterhout et al. |
| 2011/0221672 A1 | 9/2011 | Osterhout et al. |
| 2011/0221896 A1 | 9/2011 | Haddick et al. |
| 2011/0227820 A1 | 9/2011 | Haddick et al. |
| 2011/0234631 A1 | 9/2011 | Kim et al. |
| 2011/0248963 A1 | 10/2011 | Lawrence et al. |
| 2011/0285638 A1 | 11/2011 | Harris et al. |
| 2012/0026088 A1 | 2/2012 | Goran |
| 2012/0035934 A1 | 2/2012 | Cunningham et al. |
| 2012/0050140 A1 | 3/2012 | Border et al. |
| 2012/0050493 A1 | 3/2012 | Ernst et al. |
| 2012/0056093 A1 | 3/2012 | Poteet et al. |
| 2012/0062444 A1 | 3/2012 | Cok et al. |
| 2012/0062594 A1 | 3/2012 | Campbell et al. |
| 2012/0062998 A1 | 3/2012 | Schultz et al. |
| 2012/0068913 A1 | 3/2012 | Bar-Zeev et al. |
| 2012/0069413 A1 | 3/2012 | Schultz et al. |
| 2012/0075168 A1 | 3/2012 | Osterhout et al. |
| 2012/0078628 A1 | 3/2012 | Ghulman |
| 2012/0092328 A1 | 4/2012 | Flaks et al. |
| 2012/0092329 A1 | 4/2012 | Koo et al. |
| 2012/0113514 A1 | 5/2012 | Rodman |
| 2012/0119978 A1 | 5/2012 | Bietry et al. |
| 2012/0120103 A1 | 5/2012 | Border et al. |
| 2012/0127284 A1 | 5/2012 | Bar-Zeev et al. |
| 2012/0163013 A1 | 6/2012 | Buelow, II et al. |
| 2012/0176682 A1 | 7/2012 | DeJong et al. |
| 2012/0188245 A1 | 7/2012 | Hyatt et al. |
| 2012/0194550 A1 | 8/2012 | Osterhout et al. |
| 2012/0194553 A1 | 8/2012 | Osterhout et al. |
| 2012/0200935 A1 | 8/2012 | Miyao et al. |
| 2012/0212398 A1 | 8/2012 | Border et al. |
| 2012/0212499 A1 | 8/2012 | Haddick et al. |
| 2012/0212593 A1 | 8/2012 | Na'Aman et al. |
| 2012/0218301 A1 | 8/2012 | Miller |
| 2012/0223885 A1 | 9/2012 | Perez |
| 2012/0229367 A1 | 9/2012 | Magyari et al. |
| 2012/0233000 A1 | 9/2012 | Fisher et al. |
| 2012/0237085 A1 | 9/2012 | Meier et al. |
| 2012/0242251 A1 | 9/2012 | Kwisthout et al. |
| 2012/0249741 A1 | 10/2012 | Maciocci et al. |
| 2012/0250152 A1 | 10/2012 | Larson et al. |
| 2012/0264510 A1 | 10/2012 | Wigdor et al. |
| 2012/0287398 A1 | 11/2012 | Baker et al. |
| 2012/0293548 A1 | 11/2012 | Perez et al. |
| 2012/0294478 A1 | 11/2012 | Publicover et al. |
| 2012/0306850 A1 | 12/2012 | Balan et al. |
| 2012/0326948 A1 | 12/2012 | Crocco et al. |
| 2012/0327040 A1 | 12/2012 | Simon et al. |
| 2012/0327116 A1 | 12/2012 | Liu et al. |
| 2013/0009366 A1 | 1/2013 | Hannegan et al. |
| 2013/0009907 A1 | 1/2013 | Rosenberg et al. |
| 2013/0069985 A1 | 3/2013 | Wong et al. |
| 2013/0070344 A1 | 3/2013 | Takeda et al. |
| 2013/0077049 A1 | 3/2013 | Bohn et al. |
| 2013/0083009 A1 | 4/2013 | Geisner et al. |
| 2013/0083055 A1 | 4/2013 | Piemonte et al. |
| 2013/0088413 A1 | 4/2013 | Raffle et al. |
| 2013/0100259 A1 | 4/2013 | Ramaswamy |
| 2013/0106674 A1 | 5/2013 | Wheeler et al. |
| 2013/0120224 A1 | 5/2013 | Cajigas et al. |
| 2013/0120841 A1 | 5/2013 | Shpunt et al. |
| 2013/0127980 A1 | 5/2013 | Haddick |
| 2013/0135198 A1 | 5/2013 | Hodge et al. |
| 2013/0141434 A1 | 6/2013 | Sugden et al. |
| 2013/0154913 A1 | 6/2013 | Genc et al. |
| 2013/0162632 A1 | 6/2013 | Varga et al. |
| 2013/0176533 A1 | 7/2013 | Raffle et al. |
| 2013/0185052 A1 | 7/2013 | Boyd et al. |
| 2013/0194389 A1 | 8/2013 | Vaught et al. |
| 2013/0196757 A1 | 8/2013 | Latta et al. |
| 2013/0201080 A1 | 8/2013 | Evans et al. |
| 2013/0201081 A1 | 8/2013 | Evans et al. |
| 2013/0207970 A1 | 8/2013 | Shpunt et al. |
| 2013/0215149 A1 | 8/2013 | Hayashi et al. |
| 2013/0230215 A1 | 9/2013 | Gurman et al. |
| 2013/0234914 A1 | 9/2013 | Fujimaki et al. |
| 2013/0241805 A1 | 9/2013 | Gomez et al. |
| 2013/0241948 A1 | 9/2013 | Kimura |
| 2013/0242405 A1 | 9/2013 | Gupta et al. |
| 2013/0248691 A1 | 9/2013 | Mirov et al. |
| 2013/0249778 A1 | 9/2013 | Morimoto et al. |
| 2013/0249787 A1 | 9/2013 | Morimoto |
| 2013/0250207 A1 | 9/2013 | Bohn et al. |
| 2013/0250430 A1 | 9/2013 | Robbins et al. |
| 2013/0250503 A1 | 9/2013 | Olsson et al. |
| 2013/0257622 A1 | 10/2013 | Davalos et al. |
| 2013/0265212 A1 | 10/2013 | Kato et al. |
| 2013/0265227 A1 | 10/2013 | Julian et al. |
| 2013/0278631 A1 | 10/2013 | Border et al. |
| 2013/0293530 A1 | 11/2013 | Perez et al. |
| 2013/0293580 A1 | 11/2013 | Spivack et al. |
| 2013/0300637 A1 | 11/2013 | Smits et al. |
| 2013/0300652 A1 | 11/2013 | Raffle et al. |
| 2013/0321265 A1 | 12/2013 | Bychkov et al. |
| 2013/0321271 A1 | 12/2013 | Bychkov et al. |
| 2013/0321932 A1 | 12/2013 | Hsu et al. |
| 2013/0335301 A1 | 12/2013 | Wong et al. |
| 2013/0335461 A1 | 12/2013 | Rekimoto et al. |
| 2013/0336528 A1 | 12/2013 | Itani et al. |
| 2013/0336629 A1 | 12/2013 | Mulholland et al. |
| 2013/0342571 A1 | 12/2013 | Kinnebrew et al. |
| 2013/0342981 A1 | 12/2013 | Cox et al. |
| 2013/0346245 A1 | 12/2013 | Desore et al. |
| 2014/0028704 A1 | 1/2014 | Wu et al. |
| 2014/0043682 A1 | 2/2014 | Hussey et al. |
| 2014/0062854 A1 | 3/2014 | Cho |
| 2014/0063054 A1 | 3/2014 | Osterhout et al. |
| 2014/0063473 A1 | 3/2014 | Pasolini |
| 2014/0078043 A1 | 3/2014 | Kim et al. |
| 2014/0078282 A1 | 3/2014 | Aoki et al. |
| 2014/0091984 A1 | 4/2014 | Ashbrook et al. |
| 2014/0101608 A1 | 4/2014 | Ryskamp et al. |
| 2014/0104692 A1 | 4/2014 | Bickerstaff et al. |
| 2014/0125785 A1 | 5/2014 | Na et al. |
| 2014/0129328 A1 | 5/2014 | Mathew |
| 2014/0146394 A1 | 5/2014 | Tout et al. |
| 2014/0147829 A1 | 5/2014 | Jerauld |
| 2014/0152530 A1 | 6/2014 | Venkatesha et al. |
| 2014/0152558 A1 | 6/2014 | Salter et al. |
| 2014/0152676 A1 | 6/2014 | Rohn et al. |
| 2014/0153173 A1 | 6/2014 | Pombo et al. |
| 2014/0159995 A1 | 6/2014 | Adams et al. |
| 2014/0160055 A1 | 6/2014 | Margolis et al. |
| 2014/0160157 A1 | 6/2014 | Poulos et al. |
| 2014/0160170 A1 | 6/2014 | Lyons |

(56) References Cited

U.S. PATENT DOCUMENTS

| | | |
|---|---|---|
| 2014/0168266 A1 | 6/2014 | Kimura et al. |
| 2014/0168716 A1 | 6/2014 | King et al. |
| 2014/0168735 A1 | 6/2014 | Yuan et al. |
| 2014/0176591 A1 | 6/2014 | Klein et al. |
| 2014/0176603 A1 | 6/2014 | Kumar et al. |
| 2014/0177023 A1 | 6/2014 | Gao et al. |
| 2014/0183269 A1 | 7/2014 | Glaser et al. |
| 2014/0204759 A1 | 7/2014 | Orlik et al. |
| 2014/0225814 A1 | 8/2014 | English et al. |
| 2014/0232651 A1 | 8/2014 | Kress et al. |
| 2014/0247286 A1 | 9/2014 | Chi et al. |
| 2014/0253588 A1 | 9/2014 | Mandala et al. |
| 2014/0267010 A1 | 9/2014 | Pasquero et al. |
| 2014/0285631 A1 | 9/2014 | Janky et al. |
| 2014/0306866 A1 | 10/2014 | Miller et al. |
| 2014/0310075 A1 | 10/2014 | Ricci et al. |
| 2014/0320389 A1 | 10/2014 | Scavezze et al. |
| 2014/0341441 A1 | 11/2014 | Ady et al. |
| 2014/0361957 A1 | 12/2014 | Hua et al. |
| 2014/0363797 A1 | 12/2014 | Hu et al. |
| 2014/0372957 A1 | 12/2014 | Kipman et al. |
| 2014/0375542 A1 | 12/2014 | Bohn et al. |
| 2014/0375545 A1 | 12/2014 | Finocchio et al. |
| 2014/0375683 A1 | 12/2014 | Massey et al. |
| 2015/0029088 A1 | 1/2015 | Kim et al. |
| 2015/0042544 A1 | 2/2015 | Tatsuta et al. |
| 2015/0097719 A1 | 4/2015 | Balachandreswaran et al. |
| 2015/0143297 A1 | 5/2015 | Wheeler et al. |
| 2015/0145839 A1 | 5/2015 | Hack et al. |
| 2015/0146004 A1 | 5/2015 | Rakshit et al. |
| 2015/0161913 A1 | 6/2015 | Dominguez et al. |
| 2015/0169953 A1 | 6/2015 | Border et al. |
| 2015/0178932 A1 | 6/2015 | Wyatt et al. |
| 2015/0198807 A1 | 7/2015 | Hirai |
| 2015/0201834 A1 | 7/2015 | Border et al. |
| 2015/0201835 A1 | 7/2015 | Border et al. |
| 2015/0201836 A1 | 7/2015 | Border et al. |
| 2015/0202962 A1 | 7/2015 | Habashima et al. |
| 2015/0205035 A1 | 7/2015 | Border et al. |
| 2015/0205100 A1 | 7/2015 | Border |
| 2015/0205101 A1 | 7/2015 | Border |
| 2015/0205102 A1 | 7/2015 | Border |
| 2015/0205103 A1 | 7/2015 | Border |
| 2015/0205104 A1 | 7/2015 | Border |
| 2015/0205105 A1 | 7/2015 | Border |
| 2015/0205107 A1 | 7/2015 | Border |
| 2015/0205108 A1 | 7/2015 | Border et al. |
| 2015/0205111 A1 | 7/2015 | Border et al. |
| 2015/0205112 A1 | 7/2015 | Border |
| 2015/0205113 A1 | 7/2015 | Border et al. |
| 2015/0205114 A1 | 7/2015 | Border et al. |
| 2015/0205115 A1 | 7/2015 | Border et al. |
| 2015/0205116 A1 | 7/2015 | Border et al. |
| 2015/0205117 A1 | 7/2015 | Border et al. |
| 2015/0205118 A1 | 7/2015 | Border et al. |
| 2015/0205119 A1 | 7/2015 | Osterhout et al. |
| 2015/0205120 A1 | 7/2015 | Border et al. |
| 2015/0205121 A1 | 7/2015 | Border et al. |
| 2015/0205122 A1 | 7/2015 | Border et al. |
| 2015/0205123 A1 | 7/2015 | Border |
| 2015/0205124 A1 | 7/2015 | Border |
| 2015/0205125 A1 | 7/2015 | Border et al. |
| 2015/0205126 A1 | 7/2015 | Schowengerdt |
| 2015/0205127 A1 | 7/2015 | Border et al. |
| 2015/0205128 A1 | 7/2015 | Border |
| 2015/0205129 A1 | 7/2015 | Border et al. |
| 2015/0205130 A1 | 7/2015 | Border |
| 2015/0205131 A1 | 7/2015 | Border et al. |
| 2015/0205132 A1 | 7/2015 | Osterhout et al. |
| 2015/0205135 A1 | 7/2015 | Border et al. |
| 2015/0205346 A1 | 7/2015 | Border |
| 2015/0205347 A1 | 7/2015 | Border |
| 2015/0205348 A1 | 7/2015 | Nortrup et al. |
| 2015/0205349 A1 | 7/2015 | Nortrup et al. |
| 2015/0205351 A1 | 7/2015 | Osterhout et al. |
| 2015/0205373 A1 | 7/2015 | Osterhout et al. |
| 2015/0205378 A1 | 7/2015 | Osterhout |
| 2015/0205384 A1 | 7/2015 | Osterhout et al. |
| 2015/0205385 A1 | 7/2015 | Osterhout et al. |
| 2015/0205387 A1 | 7/2015 | Osterhout et al. |
| 2015/0205388 A1 | 7/2015 | Osterhout |
| 2015/0205401 A1 | 7/2015 | Osterhout |
| 2015/0205402 A1 | 7/2015 | Osterhout |
| 2015/0205494 A1 | 7/2015 | Scott et al. |
| 2015/0205566 A1 | 7/2015 | Osterhout |
| 2015/0206008 A1 | 7/2015 | Border et al. |
| 2015/0206173 A1 | 7/2015 | Nortrup et al. |
| 2015/0212324 A1 | 7/2015 | Osterhout |
| 2015/0212327 A1 | 7/2015 | Osterhout et al. |
| 2015/0213584 A1 | 7/2015 | Ishikawa et al. |
| 2015/0213650 A1 | 7/2015 | Barzuza et al. |
| 2015/0226966 A1 | 8/2015 | Osterhout |
| 2015/0226967 A1 | 8/2015 | Osterhout et al. |
| 2015/0228099 A1 | 8/2015 | Osterhout |
| 2015/0228119 A1 | 8/2015 | Osterhout et al. |
| 2015/0228120 A1 | 8/2015 | Osterhout et al. |
| 2015/0229019 A1 | 8/2015 | Osterhout |
| 2015/0234508 A1 | 8/2015 | Cho et al. |
| 2015/0235422 A1 | 8/2015 | Lohse et al. |
| 2015/0235429 A1 | 8/2015 | Miller et al. |
| 2015/0235622 A1 | 8/2015 | Border et al. |
| 2015/0241963 A1 | 8/2015 | Nortrup et al. |
| 2015/0241964 A1 | 8/2015 | Nortrup et al. |
| 2015/0241965 A1 | 8/2015 | Nortrup et al. |
| 2015/0241966 A1 | 8/2015 | Nortrup et al. |
| 2015/0243039 A1 | 8/2015 | Holz |
| 2015/0260986 A1 | 9/2015 | Nortrup |
| 2015/0277113 A1 | 10/2015 | Border et al. |
| 2015/0277118 A1 | 10/2015 | Border et al. |
| 2015/0277120 A1 | 10/2015 | Border |
| 2015/0277122 A1 | 10/2015 | Border |
| 2015/0277549 A1 | 10/2015 | Border |
| 2015/0279104 A1 | 10/2015 | Border et al. |
| 2015/0279107 A1 | 10/2015 | Border et al. |
| 2015/0279108 A1 | 10/2015 | Border |
| 2015/0287048 A1 | 10/2015 | Nortrup et al. |
| 2015/0294156 A1 | 10/2015 | Border et al. |
| 2015/0294627 A1 | 10/2015 | Yoo et al. |
| 2015/0301593 A1 | 10/2015 | Border et al. |
| 2015/0302646 A1 | 10/2015 | Osterhout et al. |
| 2015/0302647 A1 | 10/2015 | Osterhout et al. |
| 2015/0309313 A1 | 10/2015 | Border et al. |
| 2015/0309314 A1 | 10/2015 | Border et al. |
| 2015/0309317 A1 | 10/2015 | Osterhout et al. |
| 2015/0309534 A1 | 10/2015 | Osterhout |
| 2015/0309562 A1 | 10/2015 | Shams et al. |
| 2015/0309995 A1 | 10/2015 | Osterhout |
| 2015/0316769 A1 | 11/2015 | Border et al. |
| 2015/0316770 A1 | 11/2015 | Border et al. |
| 2015/0316771 A1 | 11/2015 | Border et al. |
| 2015/0316772 A1 | 11/2015 | Border et al. |
| 2015/0331241 A1 | 11/2015 | Haddick et al. |
| 2015/0338661 A1 | 11/2015 | Osterhout et al. |
| 2015/0346496 A1 | 12/2015 | Haddick et al. |
| 2015/0346511 A1 | 12/2015 | Osterhout et al. |
| 2015/0347823 A1 | 12/2015 | Monnerat et al. |
| 2015/0355466 A1 | 12/2015 | Border |
| 2015/0355468 A1 | 12/2015 | Osterhout et al. |
| 2015/0356772 A1 | 12/2015 | Osterhout et al. |
| 2015/0356775 A1 | 12/2015 | Osterhout et al. |
| 2015/0356776 A1 | 12/2015 | Osterhout et al. |
| 2015/0356777 A1 | 12/2015 | Osterhout et al. |
| 2015/0356778 A1 | 12/2015 | Osterhout et al. |
| 2015/0356779 A1 | 12/2015 | Osterhout et al. |
| 2015/0363975 A1 | 12/2015 | Osterhout et al. |
| 2015/0382305 A1 | 12/2015 | Drincic |
| 2016/0005003 A1 | 1/2016 | Norris et al. |
| 2016/0011417 A1 | 1/2016 | Border et al. |
| 2016/0015470 A1 | 1/2016 | Border |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0018644 A1 | 1/2016 | Border et al. |
| 2016/0018645 A1 | 1/2016 | Haddick et al. |

(56) References Cited

U.S. PATENT DOCUMENTS

| | | |
|---|---|---|
| 2016/0018646 A1 | 1/2016 | Osterhout et al. |
| 2016/0018647 A1 | 1/2016 | Osterhout et al. |
| 2016/0018648 A1 | 1/2016 | Osterhout et al. |
| 2016/0018649 A1 | 1/2016 | Osterhout et al. |
| 2016/0018650 A1 | 1/2016 | Haddick et al. |
| 2016/0018651 A1 | 1/2016 | Haddick et al. |
| 2016/0018652 A1 | 1/2016 | Haddick et al. |
| 2016/0018653 A1 | 1/2016 | Haddick et al. |
| 2016/0018654 A1 | 1/2016 | Haddick et al. |
| 2016/0019715 A1 | 1/2016 | Haddick et al. |
| 2016/0019719 A1 | 1/2016 | Osterhout et al. |
| 2016/0021304 A1 | 1/2016 | Osterhout |
| 2016/0025974 A1 | 1/2016 | Osterhout et al. |
| 2016/0025977 A1 | 1/2016 | Osterhout |
| 2016/0025979 A1 | 1/2016 | Border et al. |
| 2016/0025980 A1 | 1/2016 | Osterhout et al. |
| 2016/0026239 A1 | 1/2016 | Border et al. |
| 2016/0027211 A1 | 1/2016 | Osterhout et al. |
| 2016/0027414 A1 | 1/2016 | Osterhout et al. |
| 2016/0048019 A1 | 2/2016 | Haddick et al. |
| 2016/0048021 A1 | 2/2016 | Border |
| 2016/0048023 A1 | 2/2016 | Haddick et al. |
| 2016/0048160 A1 | 2/2016 | Haddick et al. |
| 2016/0049008 A1 | 2/2016 | Haddick et al. |
| 2016/0054566 A1 | 2/2016 | Osterhout et al. |
| 2016/0062118 A1 | 3/2016 | Osterhout |
| 2016/0062121 A1 | 3/2016 | Border et al. |
| 2016/0062122 A1 | 3/2016 | Border |
| 2016/0077342 A1 | 3/2016 | Osterhout et al. |
| 2016/0085071 A1 | 3/2016 | Border |
| 2016/0085072 A1 | 3/2016 | Haddick et al. |
| 2016/0085278 A1 | 3/2016 | Osterhout et al. |
| 2016/0091718 A1 | 3/2016 | Border et al. |
| 2016/0091719 A1 | 3/2016 | Border |
| 2016/0109709 A1 | 4/2016 | Osterhout |
| 2016/0109711 A1 | 4/2016 | Border |
| 2016/0109713 A1 | 4/2016 | Osterhout |
| 2016/0116738 A1 | 4/2016 | Osterhout et al. |
| 2016/0116745 A1 | 4/2016 | Osterhout et al. |
| 2016/0116979 A1 | 4/2016 | Border |

FOREIGN PATENT DOCUMENTS

| | | |
|---|---|---|
| EP | 1326121 A2 | 7/2003 |
| EP | 2207164 A2 | 7/2010 |
| EP | 2486450 A1 | 8/2012 |
| EP | 2502410 A1 | 9/2012 |
| JP | 07110735 A | 4/1995 |
| JP | 2000102036 A | 4/2000 |
| JP | 2005138755 A | 6/2005 |
| JP | 2009171505 A | 7/2009 |
| JP | 5017989 B2 | 9/2012 |
| JP | 2012212990 A | 11/2012 |
| KR | 1020110101944 A | 9/2011 |
| WO | 2011143655 A1 | 11/2011 |
| WO | 2012040030 A2 | 3/2012 |
| WO | 2012058175 A1 | 5/2012 |
| WO | 2012064546 A1 | 5/2012 |
| WO | 2012082807 A2 | 6/2012 |
| WO | 2012118573 A1 | 9/2012 |
| WO | 2012118575 A2 | 9/2012 |
| WO | 2013043288 A2 | 3/2013 |
| WO | 2013049248 A2 | 4/2013 |
| WO | 2013050650 A1 | 4/2013 |
| WO | 2013103825 A1 | 7/2013 |
| WO | 2013110846 A1 | 8/2013 |
| WO | 2013170073 A1 | 11/2013 |
| WO | 2013176079 A1 | 11/2013 |
| WO | 2015/109145 A1 | 7/2015 |
| WO | 2015109145 A9 | 7/2015 |
| WO | 2015164276 A1 | 10/2015 |
| WO | 2015179877 A2 | 11/2015 |
| WO | 2015179877 A3 | 11/2015 |
| WO | 2015195444 A1 | 12/2015 |
| WO | 2016/044035 | 3/2016 |

OTHER PUBLICATIONS

US 8,743,465, 6/2014, Totani, et al., (withdrawn).
US 8,792,178, 7/2014, Totani, et al., (withdrawn).
PCT/US2015/011697, "International Application Serial No. PCT/US2015/011697, International Search Report and Written Opinion mailed Apr. 13, 2015", Osterhout Group, Inc., 14 pages.
Schedwill, "Bidirectional OLED Microdisplay", Fraunhofer Research Institution for Organics, Materials and Electronic Device Comedd, Apr. 11, 2014, 2 pages.
Vogel, et al., "Data glasses controlled by eye movements", Information and communication, Fraunhofer-Gesellschaft, Sep. 22, 2013, 2 pages.
"Audio Spotlight", by Holosonics, http://www.holosonics.com, accessed Jul. 3, 2014, 3 pages.
"Genius Ring Mice", http://www.geniusnet.com/Genius/wSite/productCompare/compare.jsp, Dec. 23, 2014, 1 page.
"Help Requested! Comments and input needed for new coaxial UAS—DIY Drones", http://diydrones.com/profiles/blogs/help-requested-comments-and-input-needed-for-new-coaxial-uas, Mar. 5, 2015, pp. 1-3.
"How Ascent AeroSystems is looking to add to your outdoor adventure", http://droneblog.com/2015/03/23/how-ascent-aerosystems-is-looking-to-add-to-your-outdoor-adventure/#!prettyPhoto, Mar. 23, 2015, pp. 1-10.
"Meet Nod, the Bluetooth Ring That Wants to Replace Your Mouse", http://www.pcmag.com/article2/0,2817,2457238,00.asp, Apr. 29, 2014, 6 pages.
"Sound from Ultrasound", Wikipedia entry, http://en.m.wikipedia.org/wiki/Sound_from_ultrasound, accessed Jul. 3, 2014, 13 pages.
Allison, Robert S. et al., ""Tolerance of Temporal Delay in Virtual Environments"", VR '01 Proceedings of the Virtual Reality 2001 Conference (VR'01), Centre for Vision Research and Departments of Computer Science and Psychology, Mar. 2001, 2-8.
Bezryadin, Sergey et al., "Brightness Calculation in Digital Image Processing", Technologies for Digital Fulfillment 2007, Las Vegas, NV, 2007, pp. 1-6.
Huang, Jin-Bin , "Image Completion Using Planar Structure Guidelines", ACM Transactions on Graphics, vol. 33, No. 4, Article 129, Jul. 2014, 1-10.
Janin, Adam L. et al., "Calibration of Head-Mounted Displays for Augmented Reality Applications", Research and Technology, Boeing Computer Services, MS 7L-48 P.O. Box 24346, Seattle, WA 98124-0346, Virtual Reality Annual International Symposium, 1993., 1993 IEEE,, 1993, 10 Pages.
Lang, Manuel et al., ""Nonlinear Disparity Mapping for Stereoscopic 3D"", Jul. 2010, pp. 1-10.
Logbar Inc., "Ring: Shortcut Everything", https://www.kickstarter.com/projects/1761670738/ring-shortcut-everything, Jun. 2012, 1 page.
Mastandrea, Nick , "Mycestro, The Next Generation 3D Mouse", https://www.kickstarter.com/projects/mycestro/mycestrotm-the-next-generation-3d-mouse, Dec. 2014, 22 pages.
Pamplona, Vitor R. et al., "Photorealistic Models for Pupil Light Reflex and Iridal Pattern Deformation", ACM Transactions on Graphics, vol. 28, No. 4, Article 106, Publication date: Aug. 2009, pp. 1-12.
PCT/US2015/026704, "International Search Report and Written Opinion", Osterhout Group, Inc., 15 pages.
PCT/US2015/035192, "International Application Serial No. PCT/US2015/035192, International Search Report and Written Opinion mailed Sep. 03, 2015", Osterhout Group, Inc., 11 pages.
PCT/US2015/059264, "International Application Serial No. PCT/US2015/059264, International Search Report and Written Opinion mailed Feb. 19, 2016". Osterhout Group, Inc., 11 Pages.
PCT/US2015/033379, "International Application Serial No. PCT/US2015/033379, International Search Report and Written Opinion mailed Nov. 30, 2016". Osterhout Group, Inc., 12 Pages.
Plainis, Sotiris et al., "The Physiologic Mechanism of Accommodation", Cataract & Refractive Surgery Today Europe, Apr. 2014, Pages 23-29.

(56) References Cited

OTHER PUBLICATIONS

Walton, Zach, "Wear This Smartphone Controller on Your Finger", http://www.webpronews.com/wear-this-smartphone-controller-on-your-finger-2012-06, 5 pages.
Ye, Hui et al., "High Quality Voice Morphing", Cambridge University Engineering Department Trumpington Street, Cambridge, England, CB2 1PZ, 2004, pp. 1-9 - 1-11.

* cited by examiner

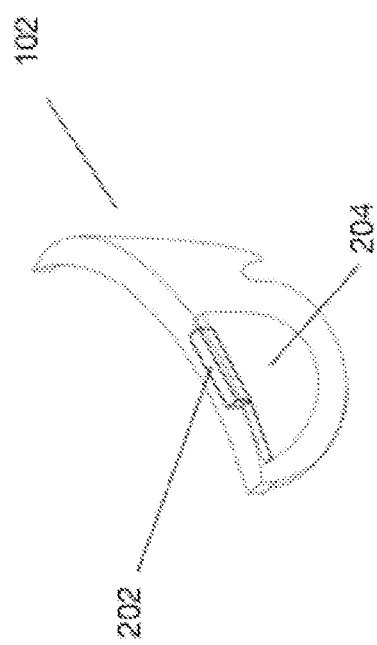

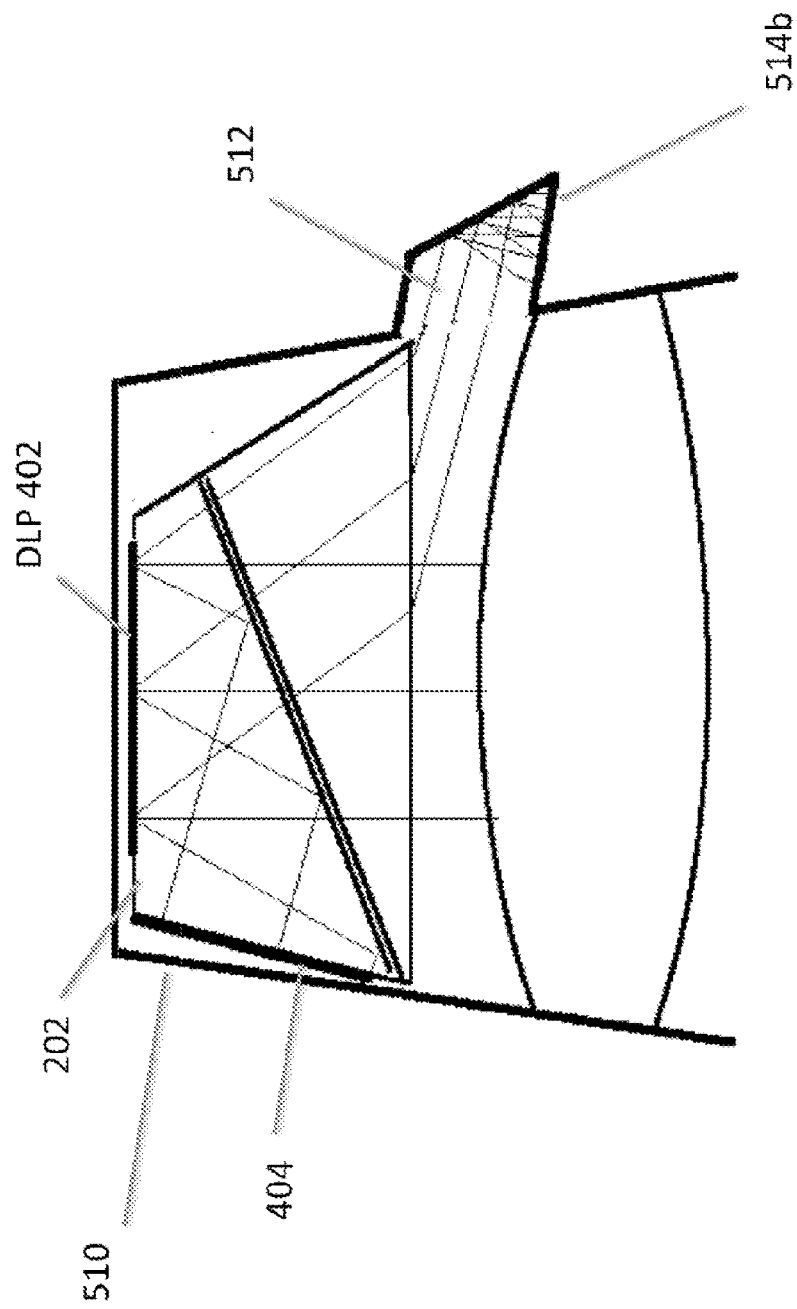

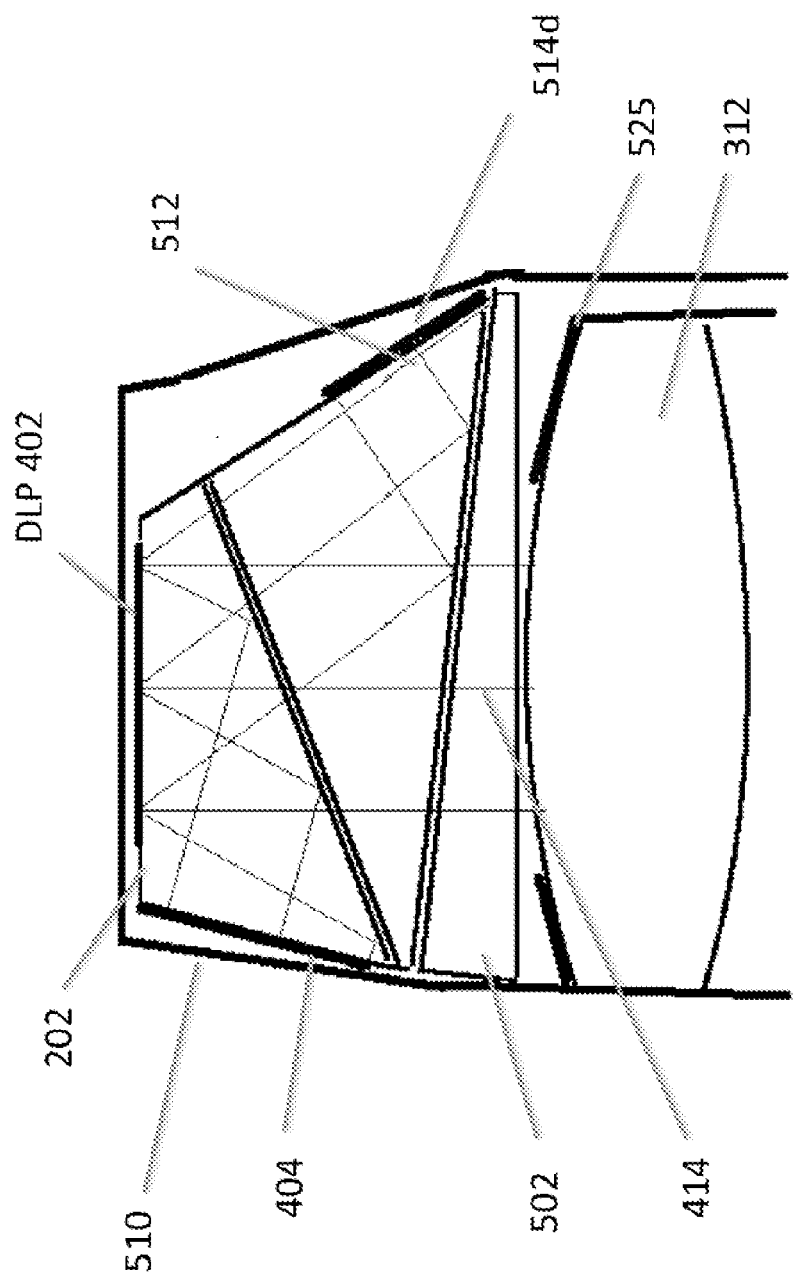

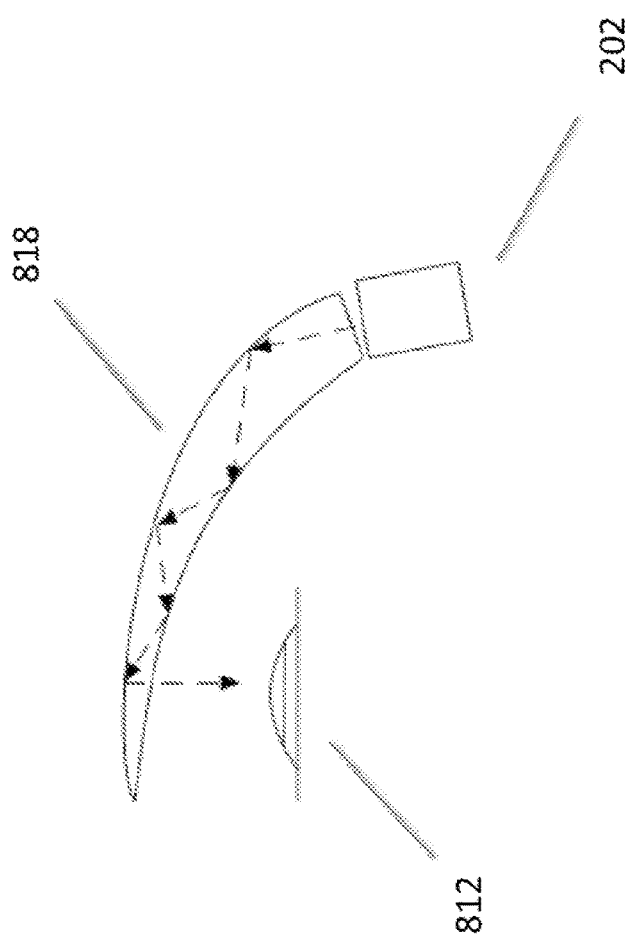

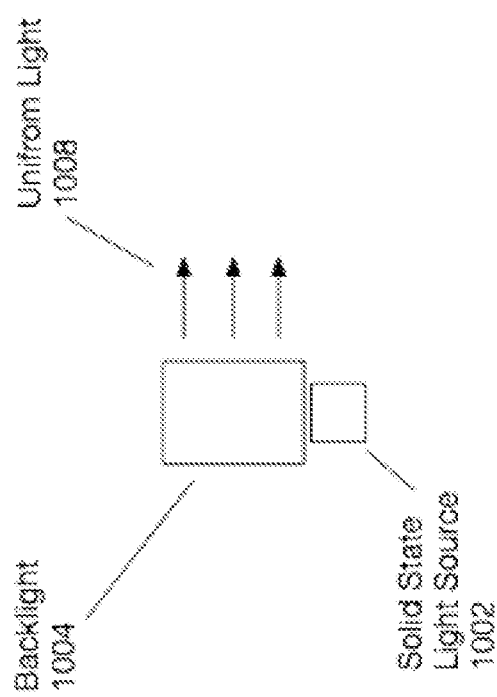

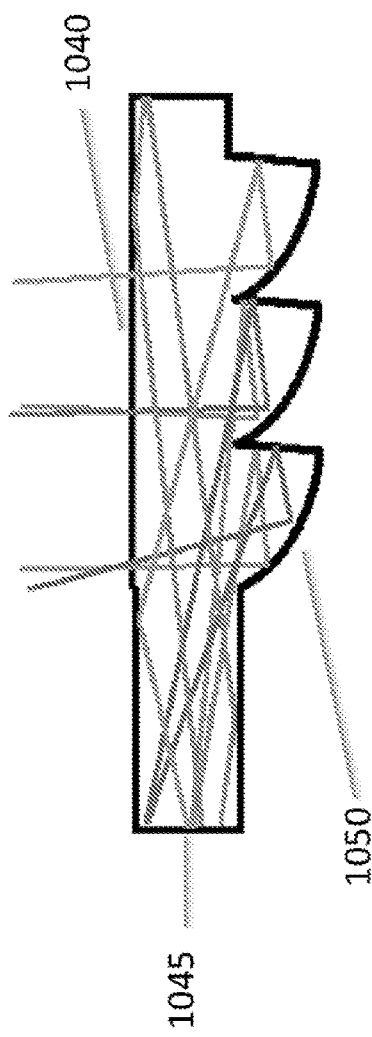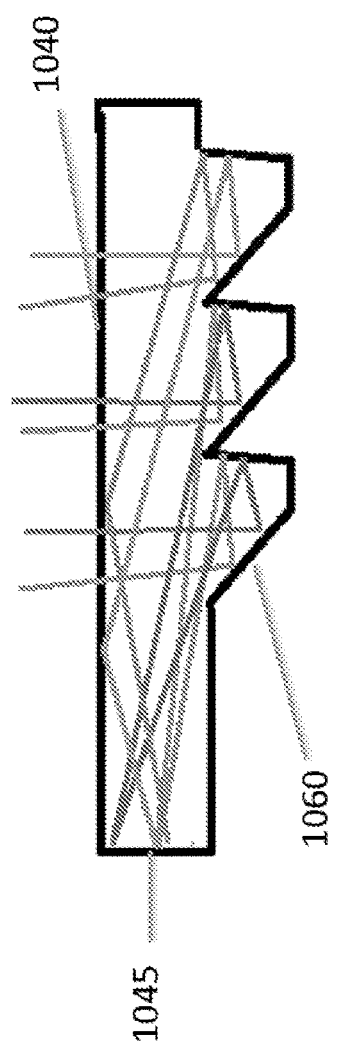

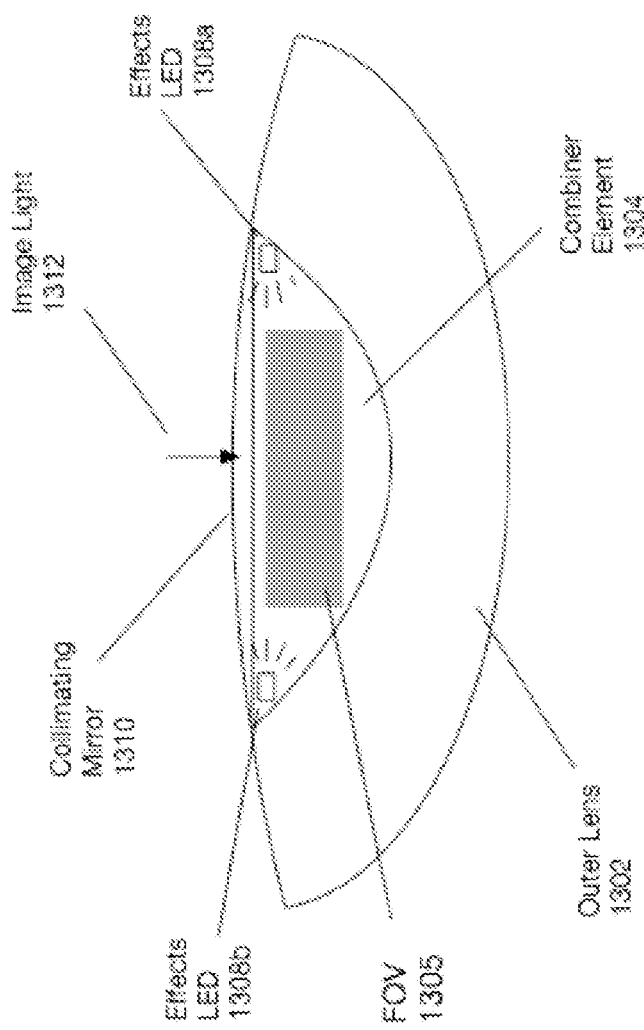

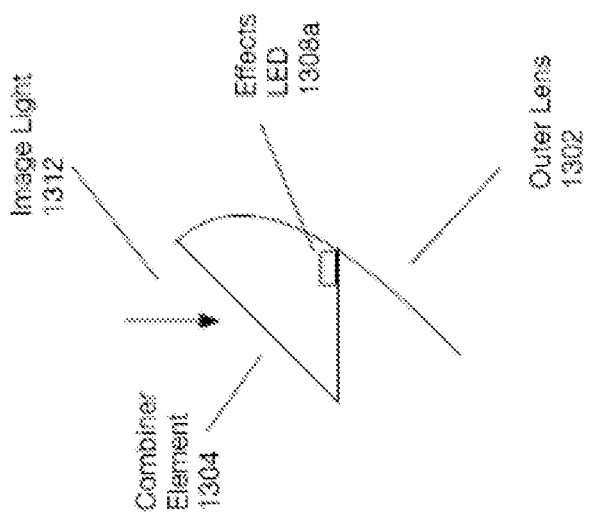

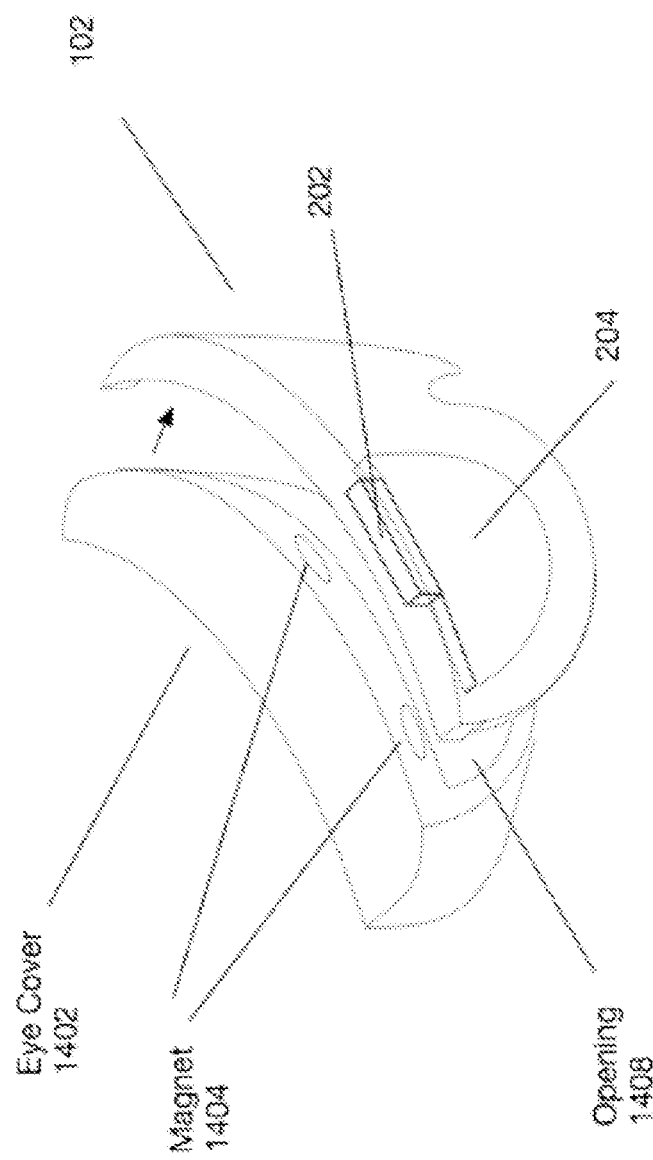

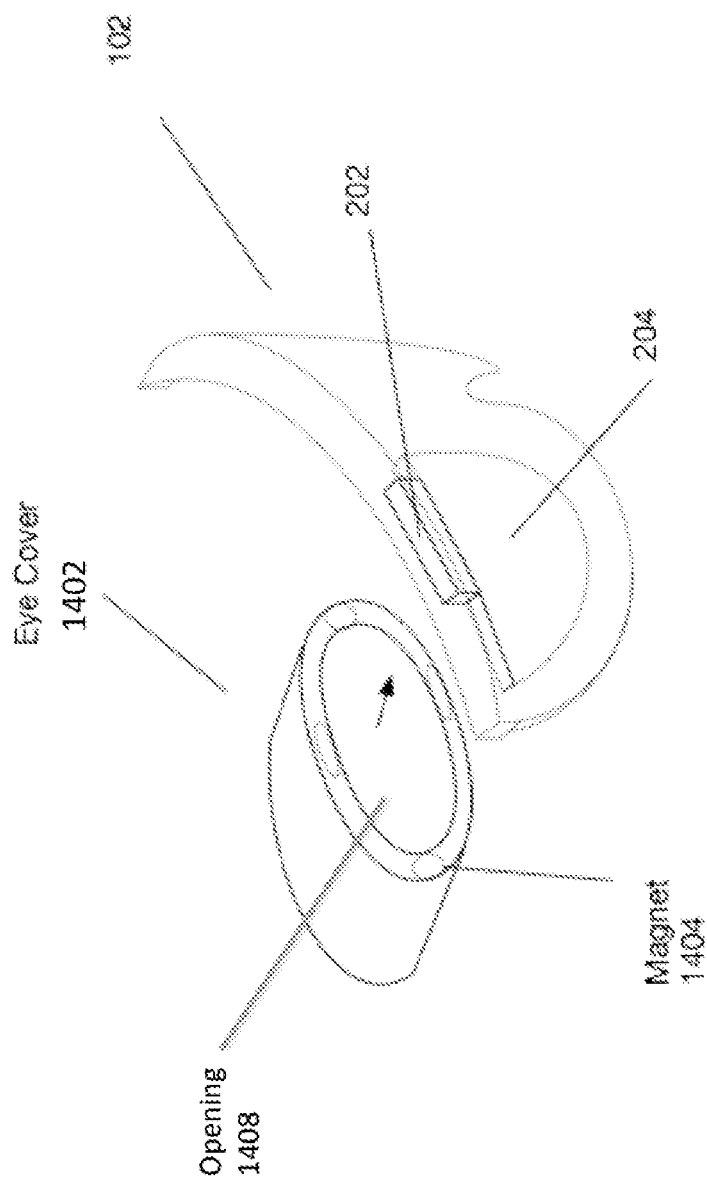

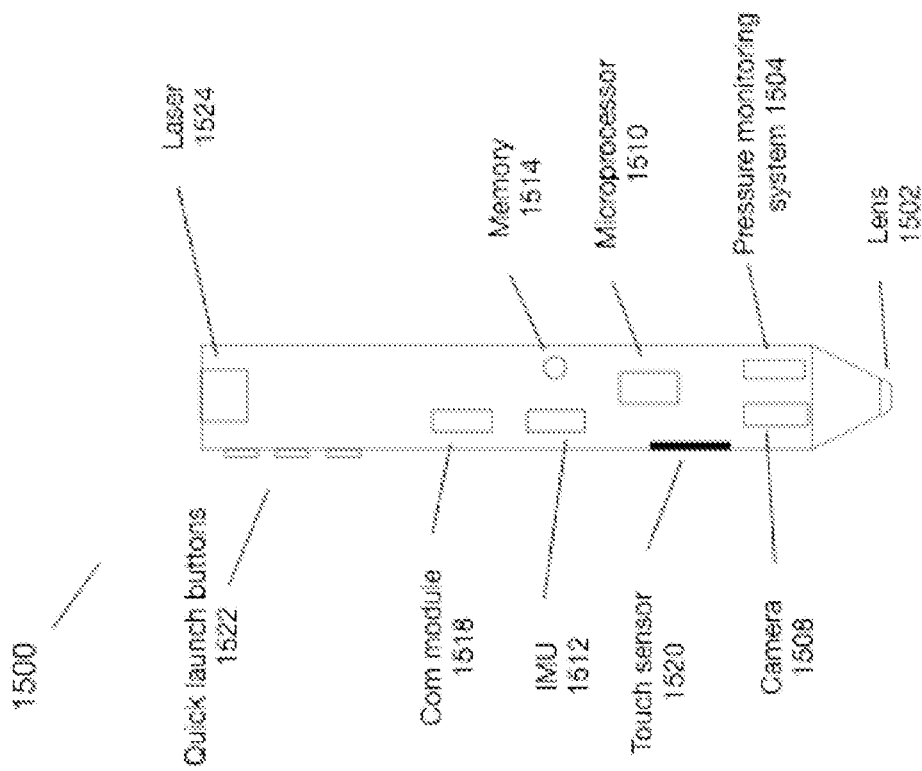

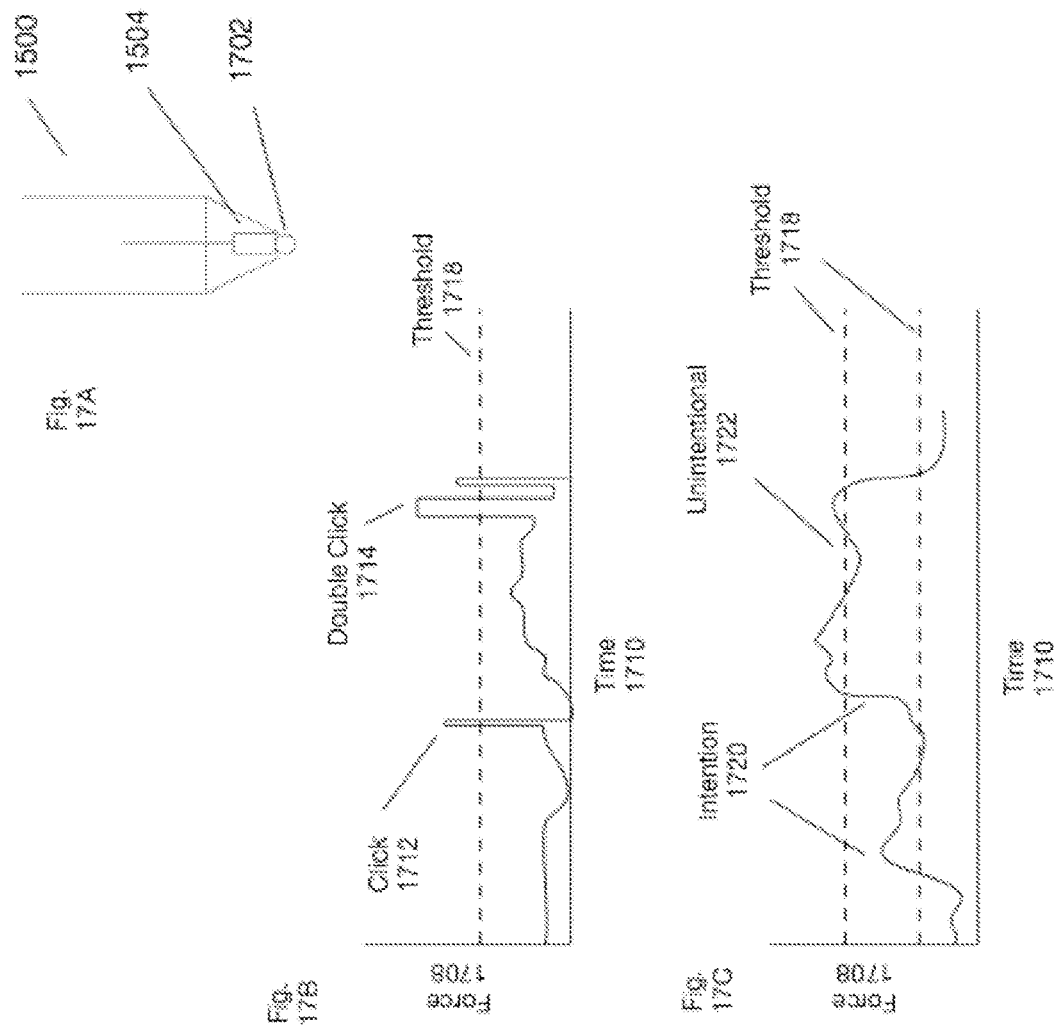

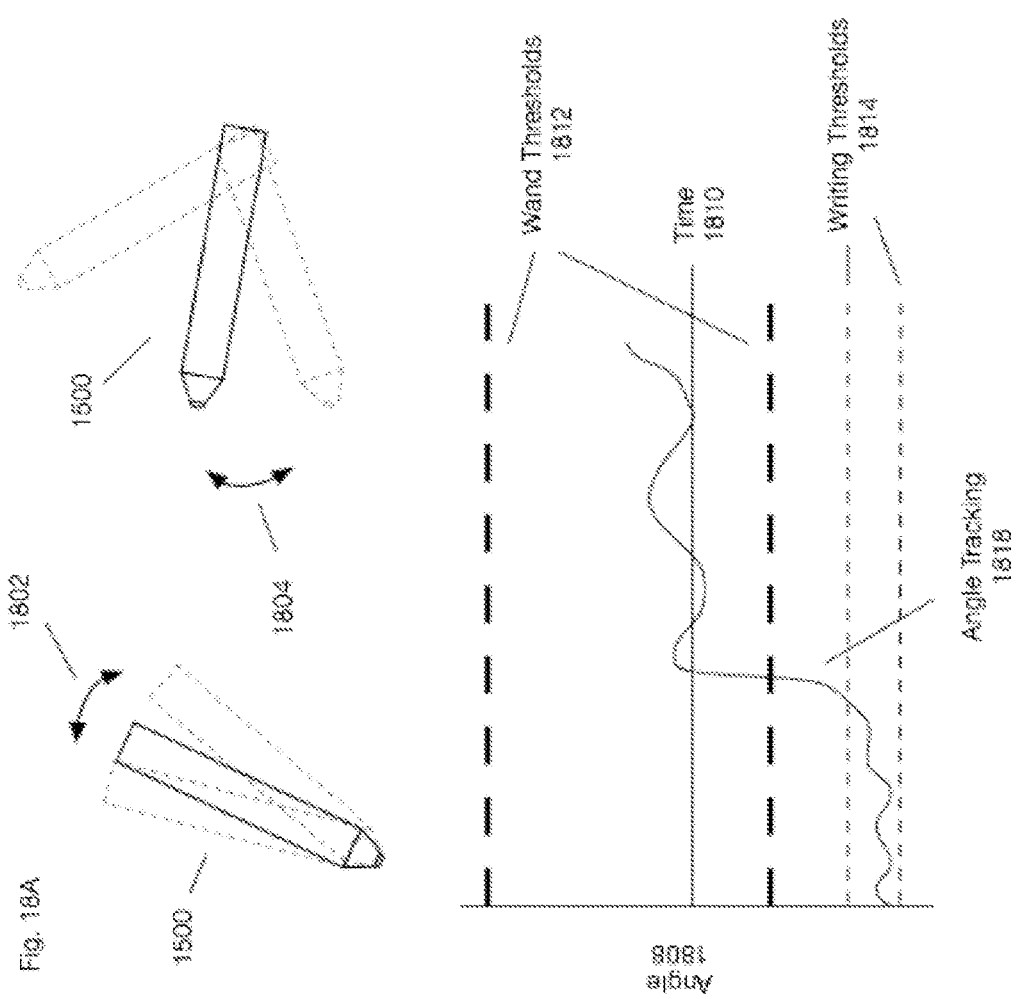

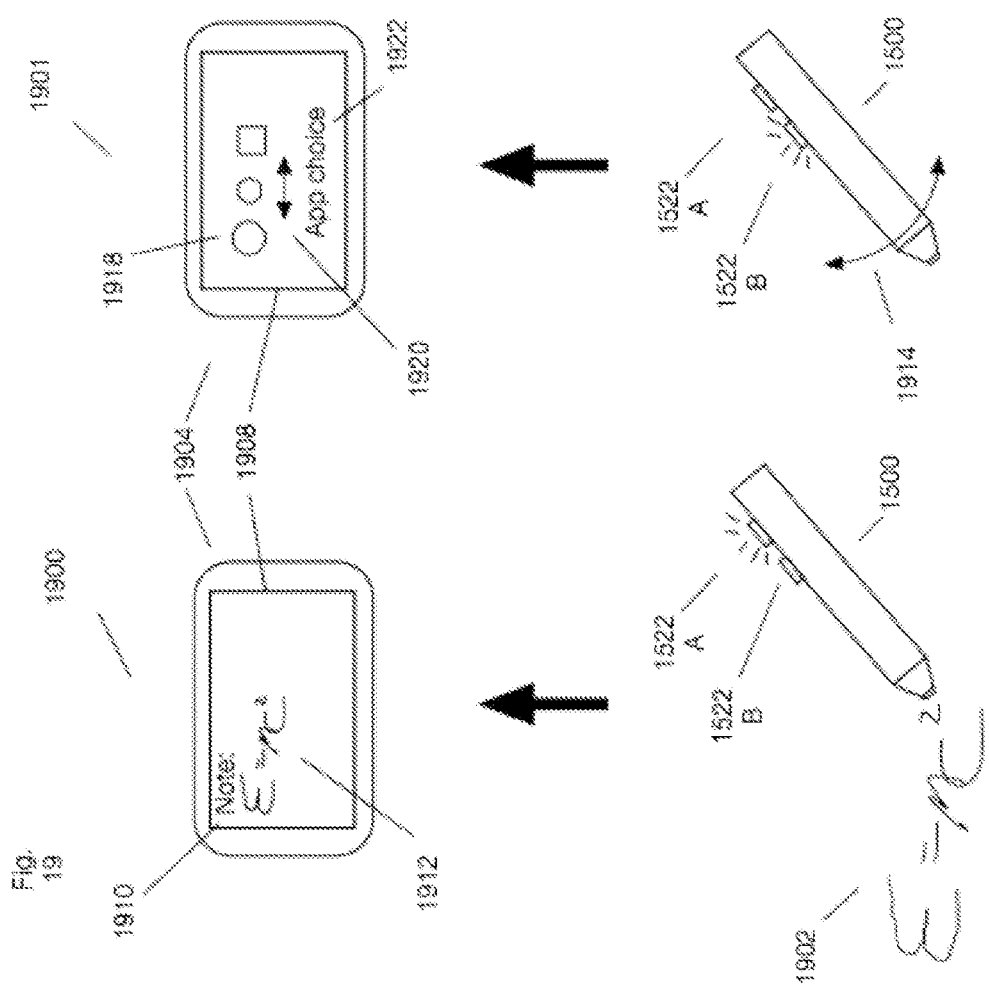

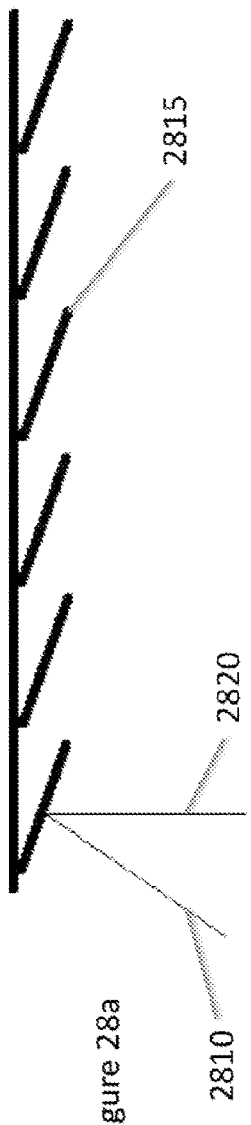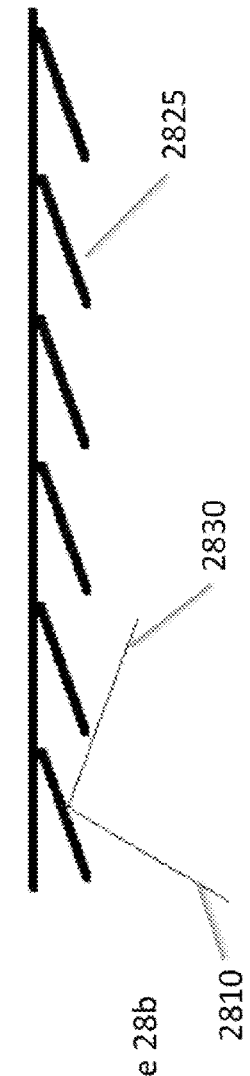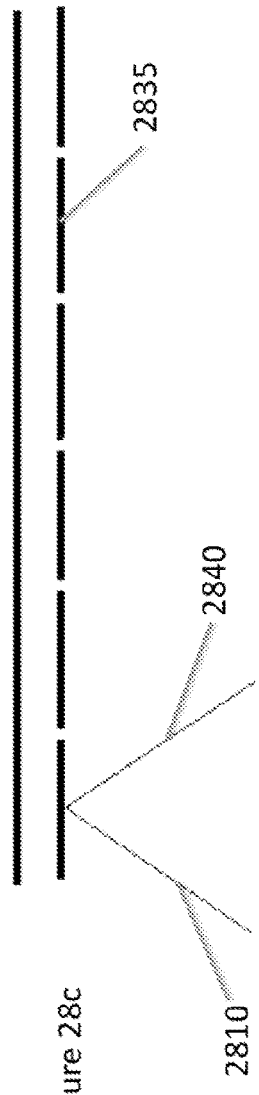

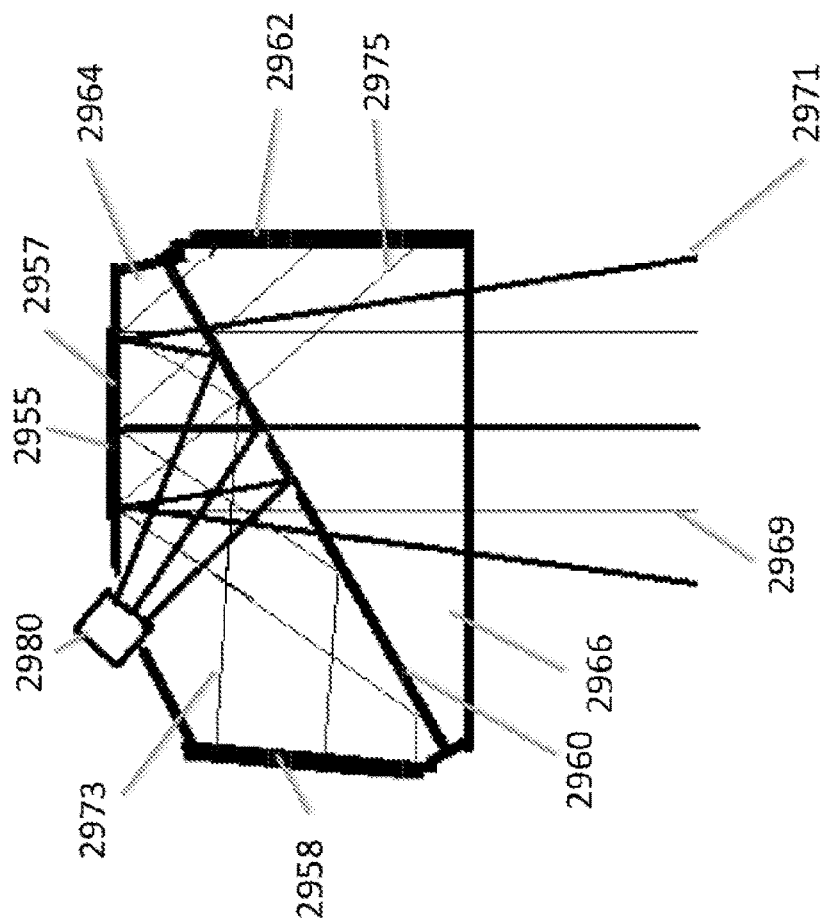

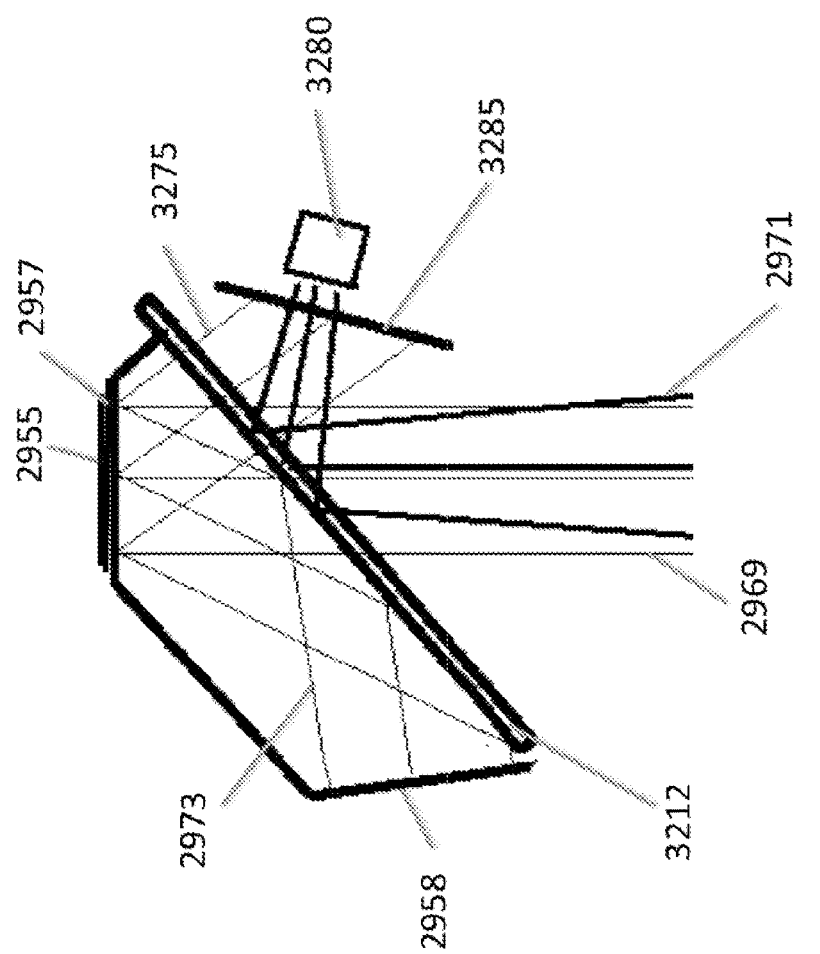

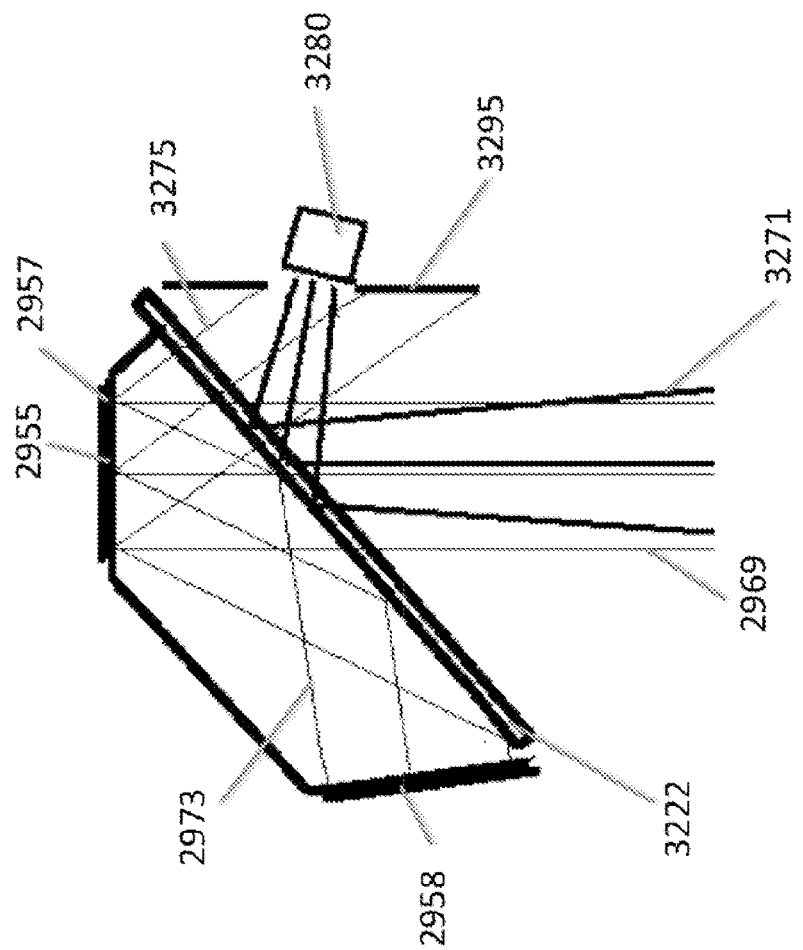

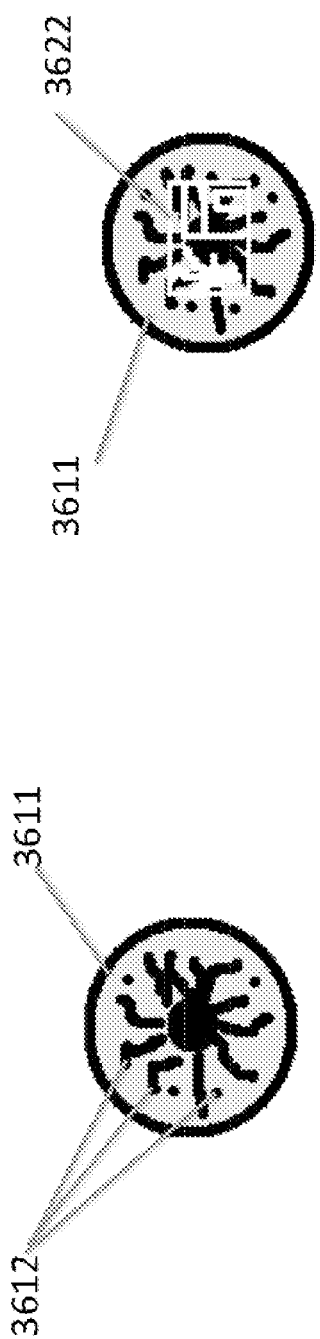

EYE IMAGING IN HEAD WORN COMPUTING

CROSS REFERENCE TO RELATED APPLICATIONS

This application claims the benefit of priority to and is a continuation of U.S. non-provisional application Ser. No. 14/216,175, entitled Eye Imaging in Head Worn Computing, filed Mar. 17, 2014 now U.S. Pat. No. 9,298,007.

U.S. non-provisional application Ser. No. 14/216,175 is a continuation-in-part of the following three U.S. patent applications:

U.S. non-provisional application Ser. No. 14/160,377, entitled Optical Configurations for Head Worn Computing, filed Jan. 21, 2014;

U.S. non-provisional application Ser. No. 14/172,901, entitled Optical Configurations for Head Worn Computing, filed Feb. 4, 2014, which is a continuation-in-part of application Ser. No. 14/163,646, filed Jan. 24, 2014 now U.S. Pat. No. 9,400,233, and U.S. non-provisional application Ser. No. 14/160,377, filed Jan. 21, 2014; and U.S. non-provisional application Ser. No. 14/181,459, entitled Suppression of Stray Light in Head Worn Computing, filed Feb. 14, 2014, which is a continuation-in-part of U.S. non-provisional application Ser. No. 14/178,047, filed Feb. 11, 2014 now U.S. Pat. No. 9,229,233, U.S. non-provisional application Ser. No. 14/172,901, filed Feb. 4, 2014, U.S. non-provisional application Ser. No. 14/163,646, filed Jan. 24, 2014 and U.S. non-provisional application Ser. No. 14/160,377, filed Jan. 21, 2014.

Each of the above applications are incorporated herein by reference in their entirety.

BACKGROUND

Field of the Invention

This invention relates to head worn computing. More particularly, this invention relates to suppression of stray light in head worn computing.

Description of Related Art

Wearable computing systems have been developed and are beginning to be commercialized. Many problems persist in the wearable computing field that need to be resolved to make them meet the demands of the market.

SUMMARY

Aspects of the present invention relate to methods and systems for imaging, recognizing, and tracking of a user's eye that is wearing a HWC. Aspects further relate to the processing of images reflected from the user's eye and controlling displayed content in accordance therewith.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE DRAWINGS

Embodiments are described with reference to the following Figures. The same numbers may be used throughout to reference like features and components that are shown in the Figures:

FIG. 2 illustrates a head worn computing system with optical system in accordance with the principles of the present invention.

FIG. 5c illustrates an upper optical module and dark light trap according to the principles of the present invention.

FIG. 5e illustrates an upper optical module and dark light trap according to the principles of the present invention.

FIG. 8b illustrates upper and lower optical modules in accordance with the principles of the present invention.

FIG. 10 illustrates a light source in accordance with the principles of the present invention.

FIG. 10a illustrates a back lighting system in accordance with the principles of the present invention.

FIG. 10b illustrates a back lighting system in accordance with the principles of the present invention.

FIGS. 13a to 13c illustrate peripheral lighting systems in accordance with the principles of the present invention.

FIGS. 14a to 14c illustrate a light suppression systems in accordance with the principles of the present invention.

FIG. 15 illustrates an external user interface in accordance with the principles of the present invention.

FIGS. 17a to 17c illustrate force interpretation systems in accordance with the principles of the present invention.

FIGS. 18a to 18c illustrate user interface mode selection systems in accordance with the principles of the present invention.

FIG. 19 illustrates interaction systems in accordance with the principles of the present invention.

FIGS. 28a to 28c illustrate DLP mirror angles.

FIGS. 29 to 33 illustrate eye imaging systems according to the principles of the present invention.

FIG. 36a illustrates eye characteristics that may be used in personal identification through analysis of a system according to the principles of the present invention.

FIG. 36b illustrates a digital content presentation reflection off of the wearer's eye that may be analyzed in accordance with the principles of the present invention.

While the invention has been described in connection with certain preferred embodiments, other embodiments would be understood by one of ordinary skill in the art and are encompassed herein.

DETAILED DESCRIPTION OF THE PREFERRED EMBODIMENT(S)

Aspects of the present invention relate to head-worn computing ("HWC") systems. HWC involves, in some instances, a system that mimics the appearance of head-worn glasses or sunglasses. The glasses may be a fully developed computing platform, such as including computer displays presented in each of the lenses of the glasses to the eyes of the user. In embodiments, the lenses and displays may be configured to allow a person wearing the glasses to see the environment through the lenses while also seeing, simultaneously, digital imagery, which forms an overlaid image that is perceived by the person as a digitally augmented image of the environment, or augmented reality ("AR").

HWC involves more than just placing a computing system on a person's head. The system may need to be designed as a lightweight, compact and fully functional computer display, such as wherein the computer display includes a high resolution digital display that provides a high level of emersion comprised of the displayed digital content and the see-through view of the environmental surroundings. User interfaces and control systems suited to the HWC device may be required that are unlike those used for a more conventional computer such as a laptop. For the HWC and associated systems to be most effective, the glasses may be equipped with sensors to determine environmental conditions, geographic location, relative positioning to other points of interest, objects identified by imaging and movement by the user or other users in a connected group, and the like. The HWC may then change the mode of operation to match the conditions, location, positioning, movements, and the like, in a method generally referred to as a contextually aware HWC. The glasses also may need to be connected, wirelessly or otherwise, to other systems either locally or through a network. Controlling the glasses may be achieved through the use of an external device, automatically through contextually gathered information, through user gestures captured by the glasses sensors, and the like. Each technique may be further refined depending on the software application being used in the glasses. The glasses may further be used to control or coordinate with external devices that are associated with the glasses.

Figure 1:
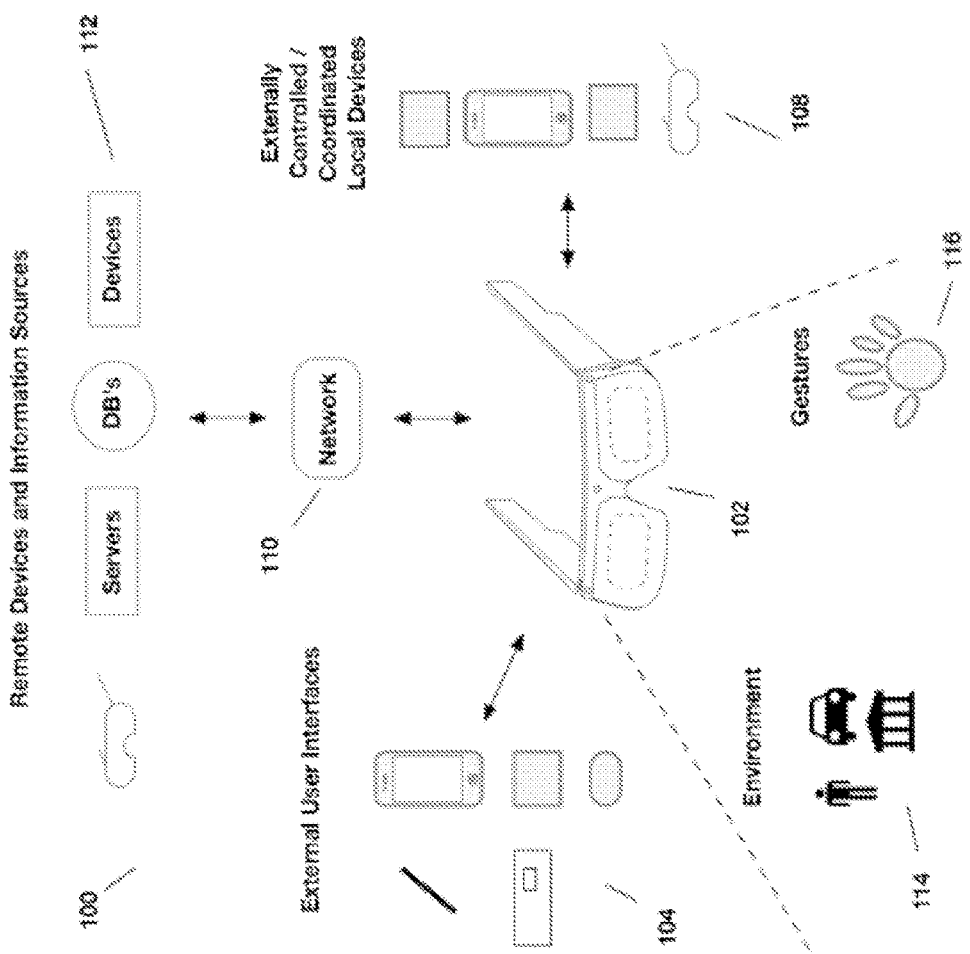
FIG. 1 illustrates a head worn computing system in accordance with the principles of the present invention.

Referring to FIG. 1, an overview of the HWC system 100 is presented. As shown, the HWC system 100 comprises a HWC 102, which in this instance is configured as glasses to be worn on the head with sensors such that the HWC 102 is aware of the objects and conditions in the environment 114. In this instance, the HWC 102 also receives and interprets control inputs such as gestures and movements 116. The HWC 102 may communicate with external user interfaces 104. The external user interfaces 104 may provide a physical user interface to take control instructions from a user of the HWC 102 and the external user interfaces 104 and the HWC 102 may communicate bi-directionally to affect the user's command and provide feedback to the external device 108. The HWC 102 may also communicate bi-directionally with externally controlled or coordinated local devices 108. For example, an external user interface 104 may be used in connection with the HWC 102 to control an externally controlled or coordinated local device 108. The externally controlled or coordinated local device 108 may provide feedback to the HWC 102 and a customized GUI may be presented in the HWC 102 based on the type of device or specifically identified device 108. The HWC 102 may also interact with remote devices and information sources 112 through a network connection 110. Again, the external user interface 104 may be used in connection with the HWC 102 to control or otherwise interact with any of the remote devices 108 and information sources 112 in a similar way as when the external user interfaces 104 are used to control or otherwise interact with the externally controlled or coordinated local devices 108. Similarly, HWC 102 may interpret gestures 116 (e.g captured from forward, downward, upward, rearward facing sensors such as camera(s), range finders, IR sensors, etc.) or environmental conditions sensed in the environment 114 to control either local or remote devices 108 or 112.

We will now describe each of the main elements depicted on FIG. 1 in more detail; however, these descriptions are intended to provide general guidance and should not be construed as limiting. Additional description of each element may also be further described herein.

The HWC 102 is a computing platform intended to be worn on a person's head. The HWC 102 may take many different forms to fit many different functional requirements. In some situations, the HWC 102 will be designed in the form of conventional glasses. The glasses may or may not have active computer graphics displays. In situations where the HWC 102 has integrated computer displays the displays may be configured as see-through displays such that the digital imagery can be overlaid with respect to the user's view of the environment 114. There are a number of see-through optical designs that may be used, including ones that have a reflective display (e.g. LCoS, DLP), emissive displays (e.g. OLED, LED), hologram, TIR waveguides, and the like. In embodiments, lighting systems used in connection with the display optics may be solid state lighting systems, such as LED, OLED, quantum dot, quantum dot LED, etc. In addition, the optical configuration may be monocular or binocular. It may also include vision corrective optical components. In embodiments, the optics may be packaged as contact lenses. In other embodiments, the HWC 102 may be in the form of a helmet with a see-through shield, sunglasses, safety glasses, goggles, a mask, fire helmet with see-through shield, police helmet with see through shield, military helmet with see-through shield, utility form customized to a certain work task (e.g. inventory control, logistics, repair, maintenance, etc.), and the like.

The HWC 102 may also have a number of integrated computing facilities, such as an integrated processor, integrated power management, communication structures (e.g. cell net, WiFi, Bluetooth, local area connections, mesh connections, remote connections (e.g. client server, etc.)), and the like. The HWC 102 may also have a number of positional awareness sensors, such as GPS, electronic compass, altimeter, tilt sensor, IMU, and the like. It may also have other sensors such as a camera, rangefinder, hyperspectral camera, Geiger counter, microphone, spectral illumination detector, temperature sensor, chemical sensor, biologic sensor, moisture sensor, ultrasonic sensor, and the like.

The HWC 102 may also have integrated control technologies. The integrated control technologies may be contextual based control, passive control, active control, user control, and the like. For example, the HWC 102 may have an integrated sensor (e.g. camera) that captures user hand or body gestures 116 such that the integrated processing system can interpret the gestures and generate control commands for the HWC 102. In another example, the HWC 102 may have sensors that detect movement (e.g. a nod, head shake, and the like) including accelerometers, gyros and other inertial measurements, where the integrated processor may interpret the movement and generate a control command in response. The HWC 102 may also automatically control itself based on measured or perceived environmental conditions. For example, if it is bright in the environment the HWC 102 may increase the brightness or contrast of the displayed image. In embodiments, the integrated control technologies may be mounted on the HWC 102 such that a user can interact with it directly. For example, the HWC 102 may have a button(s), touch capacitive interface, and the like.

As described herein, the HWC 102 may be in communication with external user interfaces 104. The external user interfaces may come in many different forms. For example, a cell phone screen may be adapted to take user input for control of an aspect of the HWC 102. The external user interface may be a dedicated UI, such as a keyboard, touch surface, button(s), joy stick, and the like. In embodiments, the external controller may be integrated into another device such as a ring, watch, bike, car, and the like. In each case, the external user interface 104 may include sensors (e.g. IMU, accelerometers, compass, altimeter, and the like) to provide additional input for controlling the HWC 102.

As described herein, the HWC 102 may control or coordinate with other local devices 108. The external devices 108 may be an audio device, visual device, vehicle, cell phone, computer, and the like. For instance, the local external device 108 may be another HWC 102, where information may then be exchanged between the separate HWCs 108.

Similar to the way the HWC 102 may control or coordinate with local devices 106, the HWC 102 may control or coordinate with remote devices 112, such as the HWC 102 communicating with the remote devices 112 through a network 110. Again, the form of the remote device 112 may have many forms. Included in these forms is another HWC 102. For example, each HWC 102 may communicate its GPS position such that all the HWCs 102 know where all of HWCs 102 are located.

FIG. 2 illustrates a HWC 102 with an optical system that includes an upper optical module 202 and a lower optical module 204. While the upper and lower optical modules 202 and 204 will generally be described as separate modules, it should be understood that this is illustrative only and the present invention includes other physical configurations, such as that when the two modules are combined into a single module or where the elements making up the two modules are configured into more than two modules. In embodiments, the upper module 202 includes a computer controlled display (e.g. LCoS, DLP, OLED, etc.) and image light delivery optics. In embodiments, the lower module includes eye delivery optics that are configured to receive the upper module's image light and deliver the image light to the eye of a wearer of the HWC. In FIG. 2, it should be noted that while the upper and lower optical modules 202 and 204 are illustrated in one side of the HWC such that image light can be delivered to one eye of the wearer, that it is envisioned by the present invention that embodiments will contain two image light delivery systems, one for each eye.

Figure 3A:
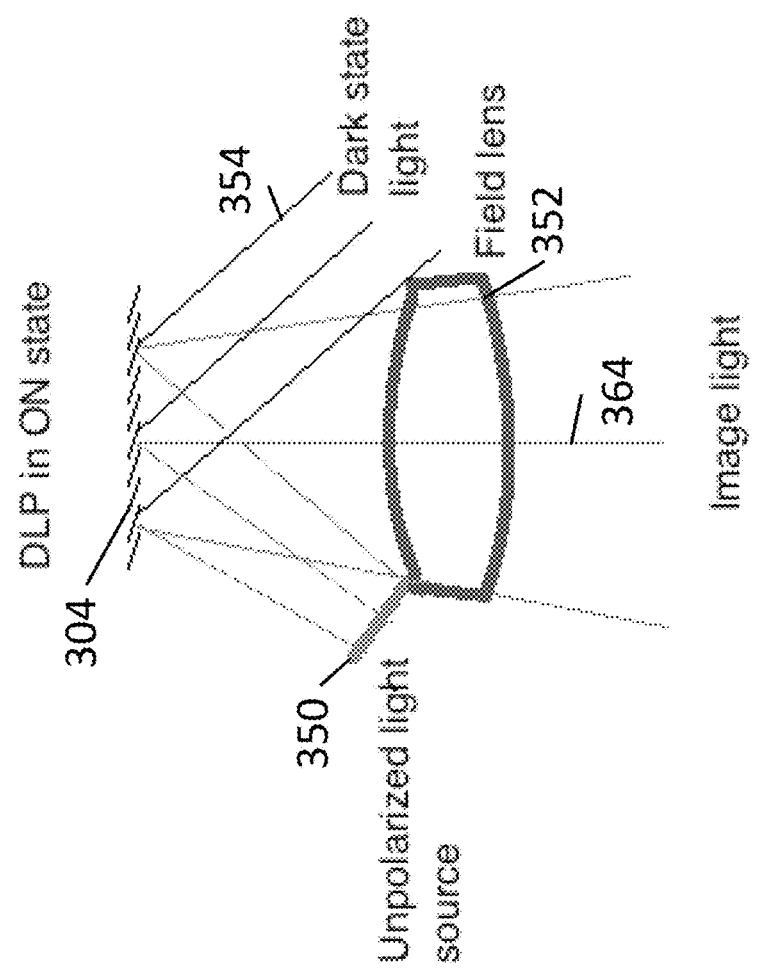
FIG. 3a illustrates a large prior art optical arrangement.
Figure 3B:
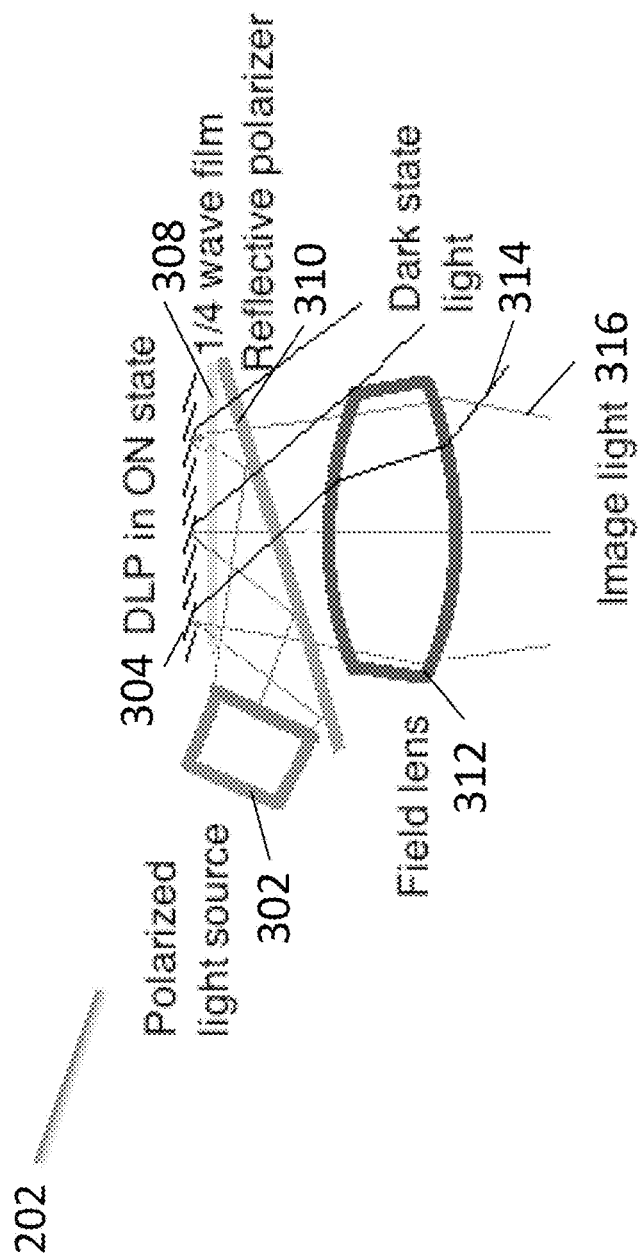
FIG. 3b illustrates an upper optical module in accordance with the principles of the present invention.

FIG. 3b illustrates an upper optical module 202 in accordance with the principles of the present invention. In this embodiment, the upper optical module 202 includes a DLP (also known as DMD or digital micromirror device) computer operated display 304 which includes pixels comprised of rotatable mirrors (such as, for example, the Digital Light Processing (DLP) display 3000 available from Texas Instruments), polarized light source 302, ¼ wave retarder film 308, reflective polarizer 310 and a field lens 312. The polarized light source 302 provides substantially uniform polarized light that is generally directed towards the reflective polarizer 310. The reflective polarizer reflects light of one polarization state (e.g. S polarized light) and transmits light of the other polarization state (e.g. P polarized light). The polarized light source 302 and the reflective polarizer 310 are oriented so that the polarized light from the polarized light source 302 is reflected generally towards the DLP display 304. The light then passes through the ¼ wave film 308 once before illuminating the pixels of the DLP display 304 and then again after being reflected by the pixels of the DLP display 304. In passing through the ¼ wave film 308 twice, the light is converted from one polarization state to the other polarization state (e.g. the light is converted from S to P polarized light). The light then passes through the reflective polarizer 310. In the event that the DLP display pixel(s) are in the "on" state (i.e. the mirrors are positioned to reflect light towards the field lens 312, the "on" pixels reflect the light generally along the optical axis and into the field lens 312. This light that is reflected by "on" pixels and which is directed generally along the optical axis of the field lens 312 will be referred to as image light 316. The image light 316 then passes through the field lens to be used by a lower optical module 204.

The light that is provided by the polarized light source 302, which is subsequently reflected by the reflective polarizer 310 before it reflects from the DLP display 304, will generally be referred to as illumination light. The light that is reflected by the "off" pixels of the DLP display 304 is reflected at a different angle than the light reflected by the 'on" pixels, so that the light from the "off" pixels is generally directed away from the optical axis of the field lens 312 and toward the side of the upper optical module 202 as shown in FIG. 3. The light that is reflected by the "off" pixels of the DLP display 304 will be referred to as dark state light 314.

The DLP display 304 operates as a computer controlled display and is generally thought of as a MEMs device. The DLP display pixels are comprised of small mirrors that can be directed. The mirrors generally flip from one angle to another angle. The two angles are generally referred to as states. When light is used to illuminate the DLP display, the mirrors will reflect the light in a direction depending on the state. In embodiments herein, we generally refer to the two states as "on" and "off," which is intended to depict the condition of a display pixel. "On" pixels will be seen by a viewer of the display as emitting light because the light is directed along the optical axis and into the field lens and the associated remainder of the display system. "Off" pixels will be seen by a viewer of the display as not emitting light because the light from these pixels is directed to the side of the optical housing and into a light trap or light dump where the light is absorbed. The pattern of "on" and "off" pixels produces image light that is perceived by a viewer of the display as a computer generated image. Full color images can be presented to a user by sequentially providing illumination light with complimentary colors such as red, green and blue. Where the sequence is presented in a recurring cycle that is faster than the user can perceive as separate images and as a result the user perceives a full color image comprised of the sum of the sequential images. Bright pixels in the image are provided by pixels that remain in the "on" state for the entire time of the cycle, while dimmer pixels in the image are provided by pixels that switch between the "on" state and "off" state within the time of the cycle, or frame time when in a video sequence of images.

FIG. 3a shows an illustration of a system for a DLP display 304 in which the unpolarized light source 350 is pointed directly at the DLP display 304. In this case, the angle required for the illumination light is such that the field lens 352 must be positioned substantially distant from the DLP display 304 to avoid the illumination light from being clipped by the field lens 352. The large distance between the field lens 352 and the DLP display 304 along with the straight path of the dark state light 354, means that the light trap for the dark state light 354 is also located at a substantial distance from the DLP display. For these reasons, this configuration is larger in size compared to the upper optics module 202 of the preferred embodiments.

The configuration illustrated in FIG. 3b can be lightweight and compact such that it fits into a small portion of a HWC. For example, the upper modules 202 illustrated herein can be physically adapted to mount in an upper frame of a HWC such that the image light can be directed into a lower optical module 204 for presentation of digital content to a wearer's eye. The package of components that combine to generate the image light (i.e. the polarized light source 302, DLP display 304, reflective polarizer 310 and ¼ wave film 308) is very light and is compact. The height of the system, excluding the field lens, may be less than 8 mm. The width (i.e. from front to back) may be less than 8 mm. The weight may be less than 2 grams. The compactness of this upper optical module 202 allows for a compact mechanical design of the HWC and the light weight nature of these embodiments help make the HWC lightweight to provide for a HWC that is comfortable for a wearer of the HWC.

The configuration illustrated in FIG. 3b can produce sharp contrast, high brightness and deep blacks, especially when compared to LCD or LCoS displays used in HWC. The "on" and "off" states of the DLP display provide for a strong differentiator in the light reflection path representing an "on" pixel and an "off" pixel. As will be discussed in more detail below, the dark state light from the "off" pixel reflections can be managed to reduce stray light in the display system to produce images with high contrast.

Figure 4:
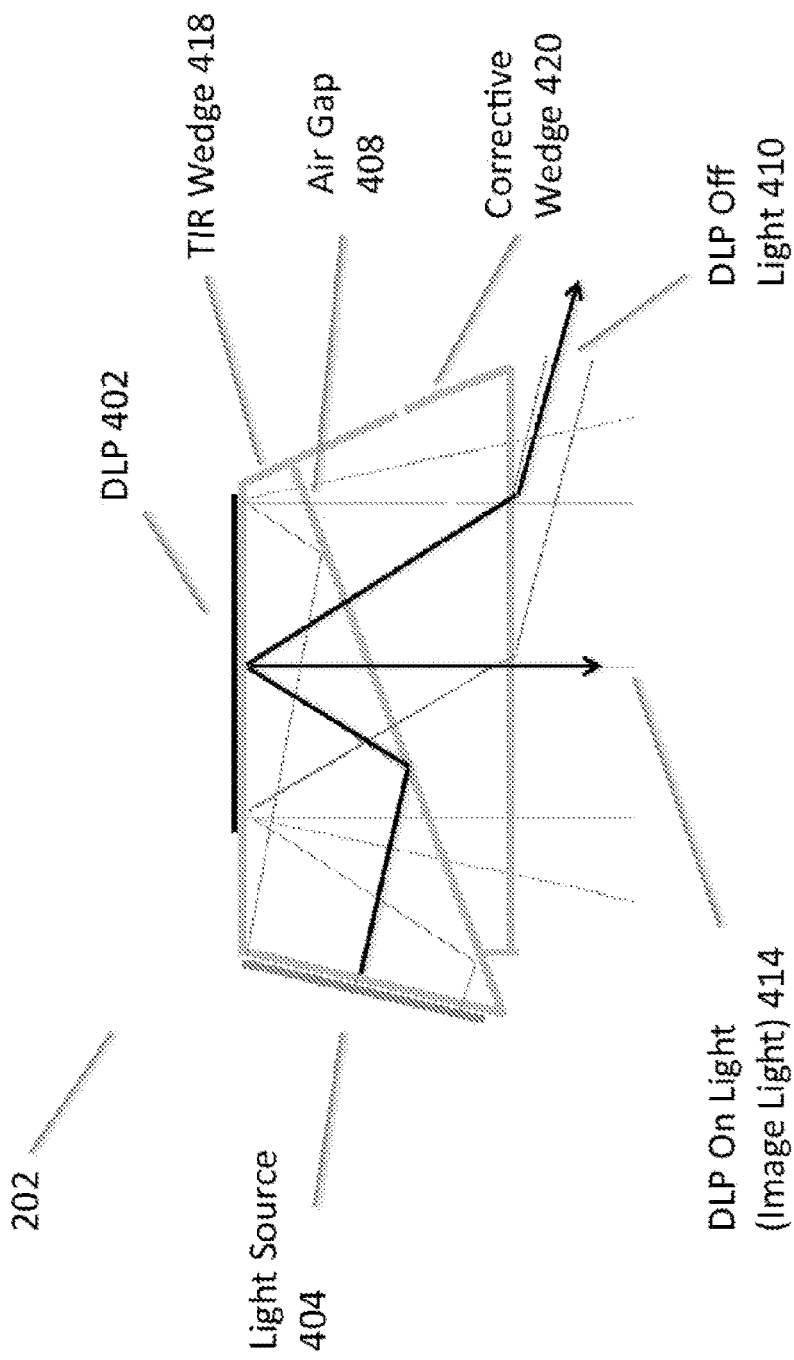
FIG. 4 illustrates an upper optical module in accordance with the principles of the present invention.

FIG. 4 illustrates another embodiment of an upper optical module 202 in accordance with the principles of the present invention. This embodiment includes a light source 404, but in this case, the light source can provide unpolarized illumination light. The illumination light from the light source 404 is directed into a TIR wedge 418 such that the illumination light is incident on an internal surface of the TIR wedge 418 (shown as the angled lower surface of the TRI wedge 418 in FIG. 4) at an angle that is beyond the critical angle as defined by Eqn 1.

$$\text{Critical angle} = \arcsin(1/n) \qquad \text{Eqn 1}$$

Where the critical angle is the angle beyond which the illumination light is reflected from the internal surface when the internal surface comprises an interface from a solid with a higher refractive index (n) to air with a refractive index of 1 (e.g. for an interface of acrylic, with a refractive index of n=1.5, to air, the critical angle is 41.8 degrees; for an interface of polycarbonate, with a refractive index of n=1.59, to air the critical angle is 38.9 degrees). Consequently, the TIR wedge 418 is associated with a thin air gap 408 along the internal surface to create an interface between a solid with a higher refractive index and air. By choosing the angle of the light source 404 relative to the DLP 402 in correspondence to the angle of the internal surface of the TIR wedge 418, illumination light is turned toward the DLP 402 at an angle suitable for providing image light 414 as reflected from "on" pixels. Wherein, the illumination light is provided to the DLP 402 at approximately twice the angle of the pixel mirrors in the DLP 402 that are in the "on" state, such that after reflecting from the pixel mirrors, the image light 414 is directed generally along the optical axis of the field lens. Depending on the state of the DLP pixels, the illumination light from "on" pixels may be reflected as image light 414 which is directed towards a field lens and a lower optical module 204, while illumination light reflected from "off" pixels (generally referred to herein as "dark" state light, "off" pixel light or "off" state light) 410 is directed in a separate direction, which may be trapped and not used for the image that is ultimately presented to the wearer's eye.

The light trap for the dark state light 410 may be located along the optical axis defined by the direction of the dark state light 410 and in the side of the housing, with the function of absorbing the dark state light. To this end, the light trap may be comprised of an area outside of the cone of image light 414 from the "on" pixels. The light trap is typically made up of materials that absorb light including coatings of black paints or other light absorbing materials to prevent light scattering from the dark state light degrading the image perceived by the user. In addition, the light trap may be recessed into the wall of the housing or include masks or guards to block scattered light and prevent the light trap from being viewed adjacent to the displayed image.

The embodiment of FIG. 4 also includes a corrective wedge 420 to correct the effect of refraction of the image light 414 as it exits the TIR wedge 418. By including the corrective wedge 420 and providing a thin air gap 408 (e.g. 25 micron), the image light from the "on" pixels can be maintained generally in a direction along the optical axis of the field lens (i.e. the same direction as that defined by the image light 414) so it passes into the field lens and the lower optical module 204. As shown in FIG. 4, the image light 414 from the "on" pixels exits the corrective wedge 420 generally perpendicular to the surface of the corrective wedge 420 while the dark state light exits at an oblique angle. As a result, the direction of the image light 414 from the "on" pixels is largely unaffected by refraction as it exits from the surface of the corrective wedge 420. In contrast, the dark state light 410 is substantially changed in direction by refraction when the dark state light 410 exits the corrective wedge 420.

Figure 4A:
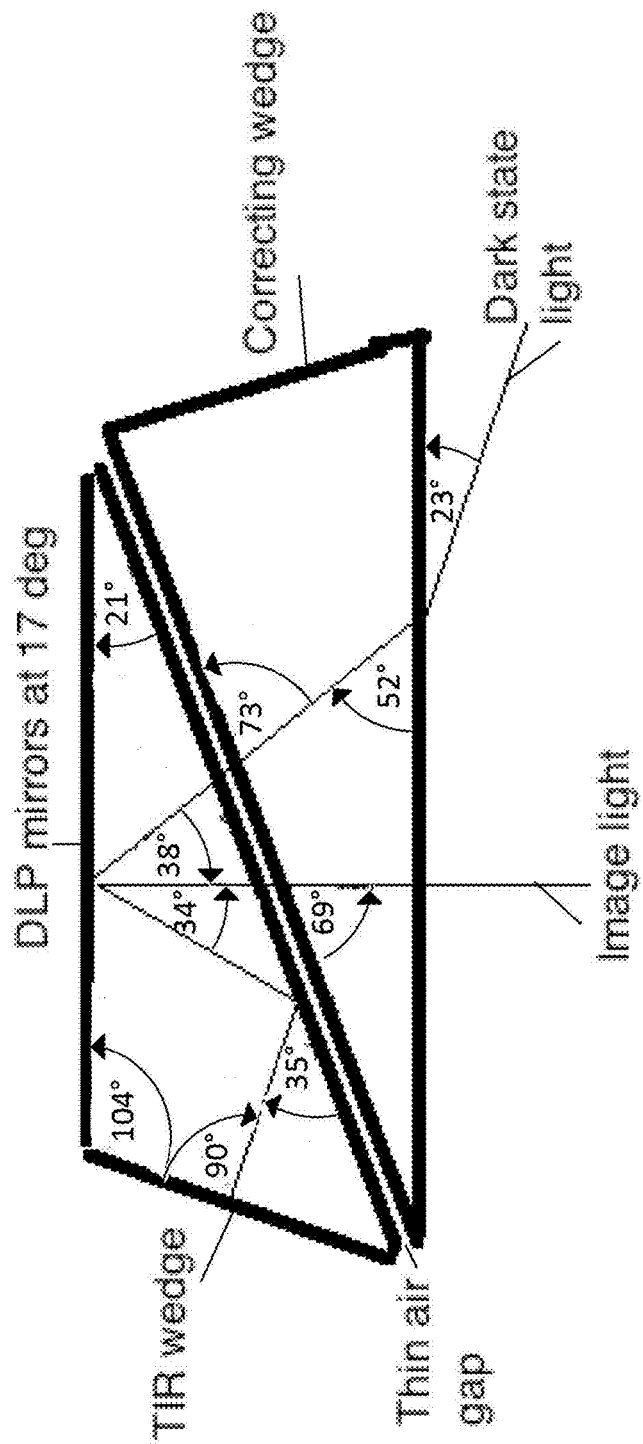
FIG. 4a illustrates an upper optical module in accordance with the principles of the present invention.

The embodiment illustrated in FIG. 4 has the similar advantages of those discussed in connection with the embodiment of FIG. 3b. The dimensions and weight of the upper module 202 depicted in FIG. 4 may be approximately 8×8 mm with a weight of less than 3 grams. A difference in overall performance between the configuration illustrated in FIGS. 3b and the configuration illustrated in FIG. 4 is that the embodiment of FIG. 4 doesn't require the use of polarized light as supplied by the light source 404. This can be an advantage in some situations as will be discussed in more detail below (e.g. increased see-through transparency of the HWC optics from the user's perspective). Polarized light may be used in connection with the embodiment depicted in FIG. 4, in embodiments. An additional advantage of the embodiment of FIG. 4 compared to the embodiment shown in FIG. 3b is that the dark state light (shown as DLP off light 410) is directed at a steeper angle away from the optical axis of the image light 414 due to the added refraction encountered when the dark state light 410 exits the corrective wedge 420. This steeper angle of the dark state light 410 allows for the light trap to be positioned closer to the DLP 402 so that the overall size of the upper module 202 can be reduced. The light trap can also be made larger since the light trap doesn't interfere with the field lens, thereby the efficiency of the light trap can be increased and as a result, stray light can be reduced and the contrast of the image perceived by the user can be increased. FIG. 4a illustrates the embodiment described in connection with FIG. 4 with an example set of corresponding angles at the various surfaces with the reflected angles of a ray of light passing through the upper optical module 202. In this example, the DLP mirrors are provided at 17 degrees to the surface of the DLP device. The angles of the TIR wedge are selected in correspondence to one another to provide TIR reflected illumination light at the correct angle for the DLP mirrors while allowing the image light and dark state light to pass through the thin air gap, various combinations of angles are possible to achieve this.

Figure 5:
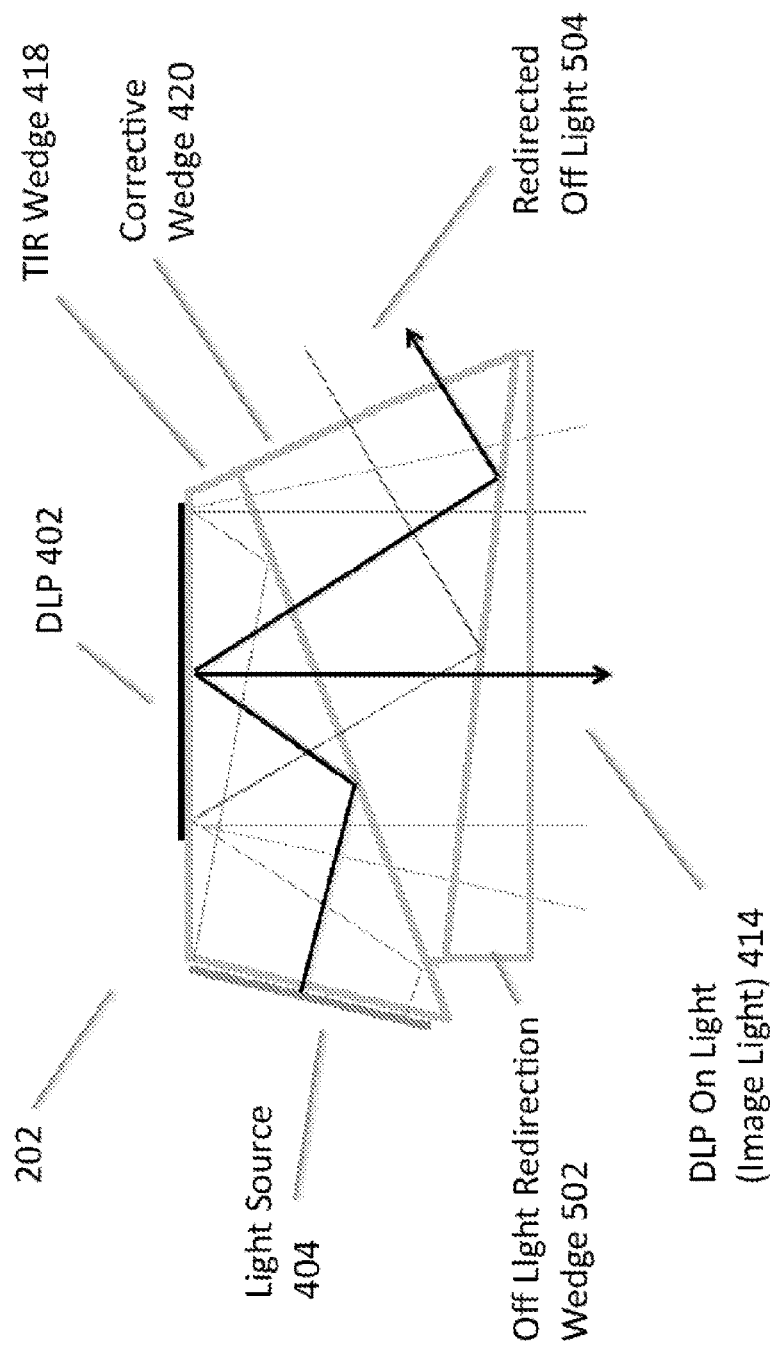
FIG. 5 illustrates an upper optical module in accordance with the principles of the present invention.
Figure 5A:
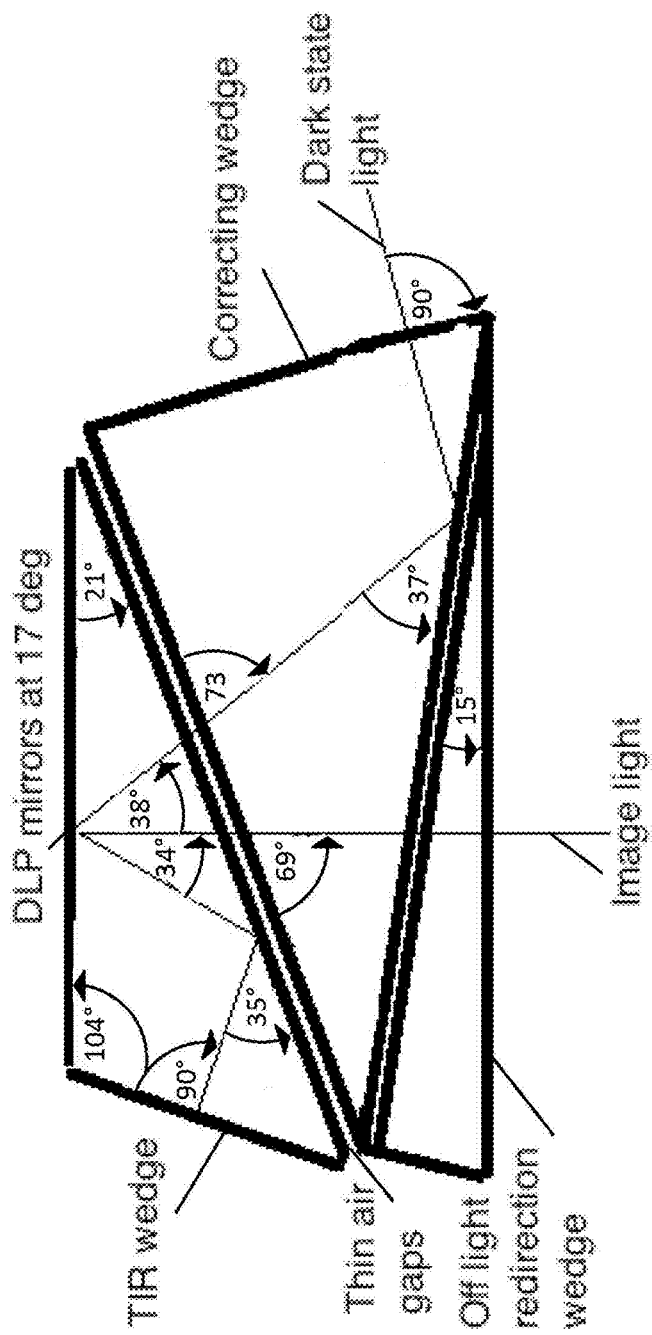
FIG. 5a illustrates an upper optical module in accordance with the principles of the present invention.

FIG. 5 illustrates yet another embodiment of an upper optical module 202 in accordance with the principles of the present invention. As with the embodiment shown in FIG. 4, the embodiment shown in FIG. 5 does not require the use of polarized light. Polarized light may be used in connection with this embodiment, but it is not required. The optical module 202 depicted in FIG. 5 is similar to that presented in connection with FIG. 4; however, the embodiment of FIG. 5 includes an off light redirection wedge 502. As can be seen from the illustration, the off light redirection wedge 502 allows the image light 414 to continue generally along the optical axis toward the field lens and into the lower optical module 204 (as illustrated). However, the off light 504 is redirected substantially toward the side of the corrective wedge 420 where it passes into the light trap. This configuration may allow further height compactness in the HWC because the light trap (not illustrated) that is intended to absorb the off light 504 can be positioned laterally adjacent the upper optical module 202 as opposed to below it. In the embodiment depicted in FIG. 5 there is a thin air gap between the TIR wedge 418 and the corrective wedge 420 (similar to the embodiment of FIG. 4). There is also a thin air gap between the corrective wedge 420 and the off light redirection wedge 502. There may be HWC mechanical configurations that warrant the positioning of a light trap for the dark state light elsewhere and the illustration depicted in FIG. 5 should be considered illustrative of the concept that the off light can be redirected to create compactness of the overall HWC. FIG. 5a illustrates an example of the embodiment described in connection with FIG. 5 with the addition of more details on the relative angles at the various surfaces and a light ray trace for image light and a light ray trace for dark light are shown as it passes through the upper optical module 202. Again, various combinations of angles are possible.

Figure 4B:
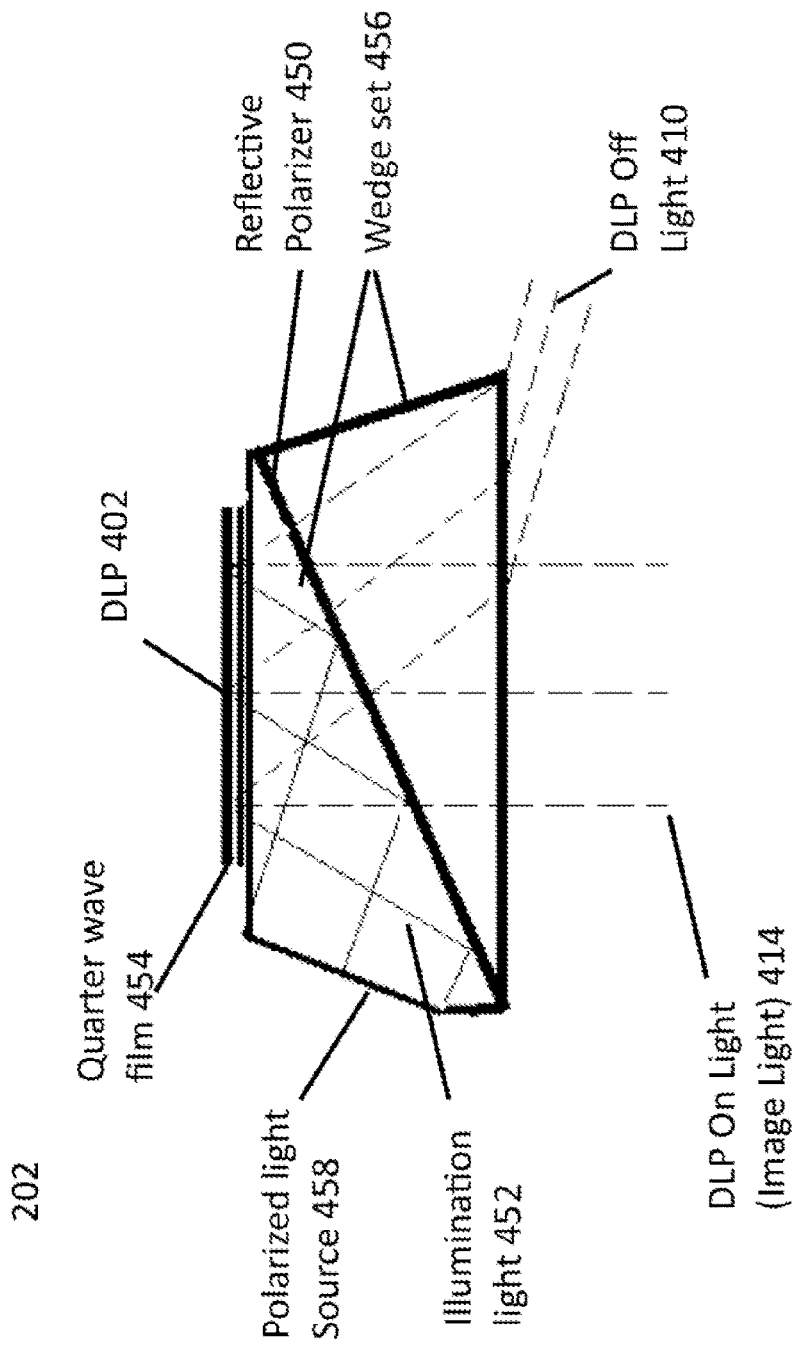
FIG. 4b illustrates an upper optical module in accordance with the principles of the present invention.

FIG. 4b shows an illustration of a further embodiment in which a solid transparent matched set of wedges 456 is provided with a reflective polarizer 450 at the interface between the wedges. Wherein the interface between the wedges in the wedge set 456 is provided at an angle so that illumination light 452 from the polarized light source 458 is reflected at the proper angle (e.g. 34 degrees for a 17 degree DLP mirror) for the DLP mirror "on" state so that the reflected image light 414 is provided along the optical axis of the field lens. The general geometry of the wedges in the wedge set 456 is similar to that shown in FIGS. 4 and 4a. A quarter wave film 454 is provided on the DLP 402 surface so that the illumination light 452 is one polarization state (e.g. S polarization state) while in passing through the quarter wave film 454, reflecting from the DLP mirror and passing back through the quarter wave film 454, the image light 414 is converted to the other polarization state (e.g. P polarization state). The reflective polarizer is oriented such that the illumination light 452 with it's polarization state is reflected and the image light 414 with it's other polarization state is transmitted. Since the dark state light from the "off" pixels 410 also passes through the quarter wave film 454 twice, it is also the other polarization state (e.g. P polarization state) so that it is transmitted by the reflective polarizer 450.

The angles of the faces of the wedge set 450 correspond to the needed angles to provide illumination light 452 at the angle needed by the DLP mirrors when in the "on" state so that the reflected image light 414 is reflected from the DLP along the optical axis of the field lens. The wedge set 456 provides an interior interface where a reflective polarizer film can be located to redirect the illumination light 452 toward the mirrors of the DLP 402. The wedge set also provides a matched wedge on the opposite side of the reflective polarizer 450 so that the image light 414 from the "on" pixels exits the wedge set 450 substantially perpendicular to the exit surface, while the dark state light from the 'off' pixels 410 exits at an oblique angle to the exit surface. As a result, the image light 414 is substantially unrefracted upon exiting the wedge set 456, while the dark state light from the "off" pixels 410 is substantially refracted upon exiting the wedge set 456 as shown in FIG. 4b.

By providing a solid transparent matched wedge set, the flatness of the interface is reduced, because variations in the flatness have a negligible effect as long as they are within the cone angle of the illuminating light 452. Which can be f#2.2 with a 26 degree cone angle. In a preferred embodiment, the reflective polarizer is bonded between the matched internal surfaces of the wedge set 456 using an optical adhesive so that Fresnel reflections at the interfaces on either side of the reflective polarizer 450 are reduced. The optical adhesive can be matched in refractive index to the material of the wedge set 456 and the pieces of the wedge set 456 can be all made from the same material such as BK7 glass or cast acrylic. Wherein the wedge material can be selected to have low birefringence as well to reduce non-uniformities in brightness. The wedge set 456 and the quarter wave film 454 can also be bonded to the DLP 402 to further reduce Fresnel reflections at the DLP interface losses. In addition, since the image light 414 is substantially normal to the exit surface of the wedge set 456, the flatness of the surface is not critical to maintain the wavefront of the image light 414 so that high image quality can be obtained in the displayed image without requiring very tightly toleranced flatness on the exit surface.

A yet further embodiment of the invention that is not illustrated, combines the embodiments illustrated in FIG. 4*b* and FIG. 5. In this embodiment, the wedge set 456 is comprised of three wedges with the general geometry of the wedges in the wedge set corresponding to that shown in FIGS. 5 and 5*a*. A reflective polarizer is bonded between the first and second wedges similar to that shown in FIG. 4*b*, however, a third wedge is provided similar to the embodiment of FIG. 5. Wherein there is an angled thin air gap between the second and third wedges so that the dark state light is reflected by TIR toward the side of the second wedge where it is absorbed in a light trap. This embodiment, like the embodiment shown in FIG. 4*b*, uses a polarized light source as has been previously described. The difference in this embodiment is that the image light is transmitted through the reflective polarizer and is transmitted through the angled thin air gap so that it exits normal to the exit surface of the third wedge.

Figure 5B:
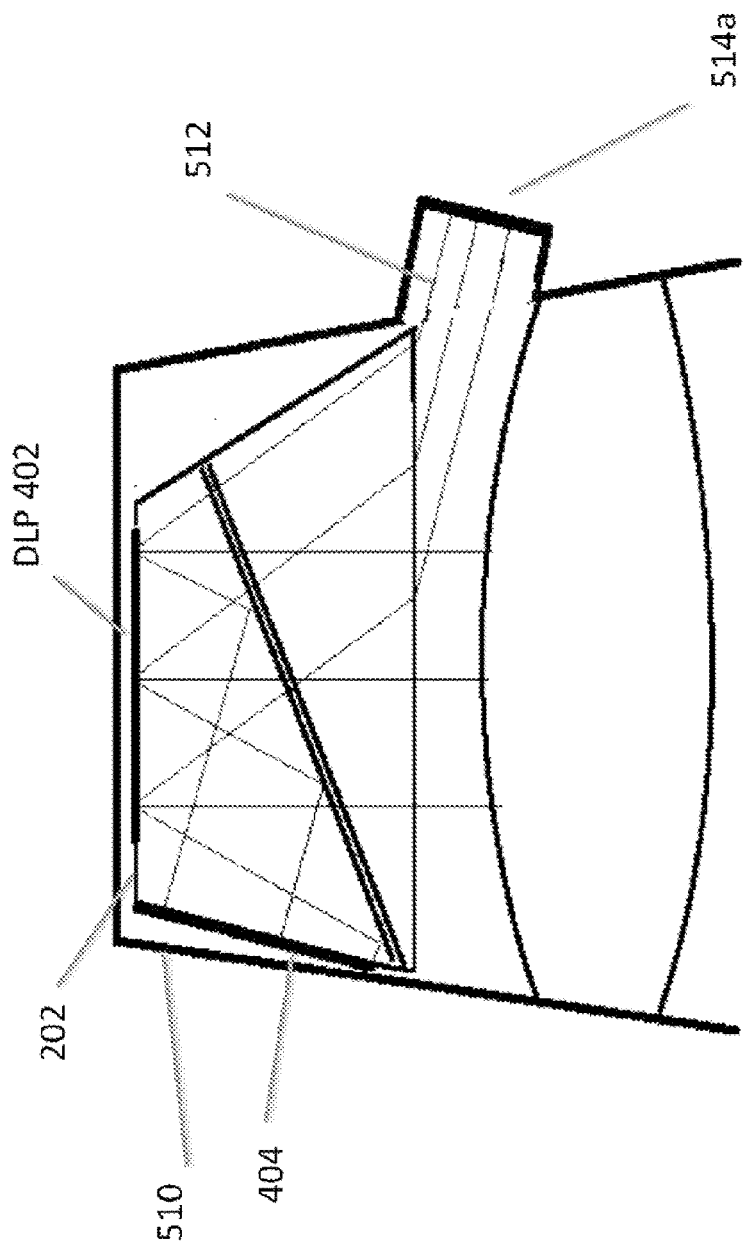
FIG. 5b illustrates an upper optical module and dark light trap according to the principles of the present invention.

FIG. 5*b* illustrates an upper optical module 202 with a dark light trap 514*a*. As described in connection with FIGS. 4 and 4*a*, image light can be generated from a DLP when using a TIR and corrective lens configuration. The upper module may be mounted in a HWC housing 510 and the housing 510 may include a dark light trap 514*a*. The dark light trap 514*a* is generally positioned/constructed/formed in a position that is optically aligned with the dark light optical axis 512. As illustrated, the dark light trap may have depth such that the trap internally reflects dark light in an attempt to further absorb the light and prevent the dark light from combining with the image light that passes through the field lens. The dark light trap may be of a shape and depth such that it absorbs the dark light. In addition, the dark light trap 514*b*, in embodiments, may be made of light absorbing materials or coated with light absorbing materials. In embodiments, the recessed light trap 514*a* may include baffles to block a view of the dark state light. This may be combined with black surfaces and textured or fiberous surfaces to help absorb the light. The baffles can be part of the light trap, associated with the housing, or field lens, etc.

Figure 5D:
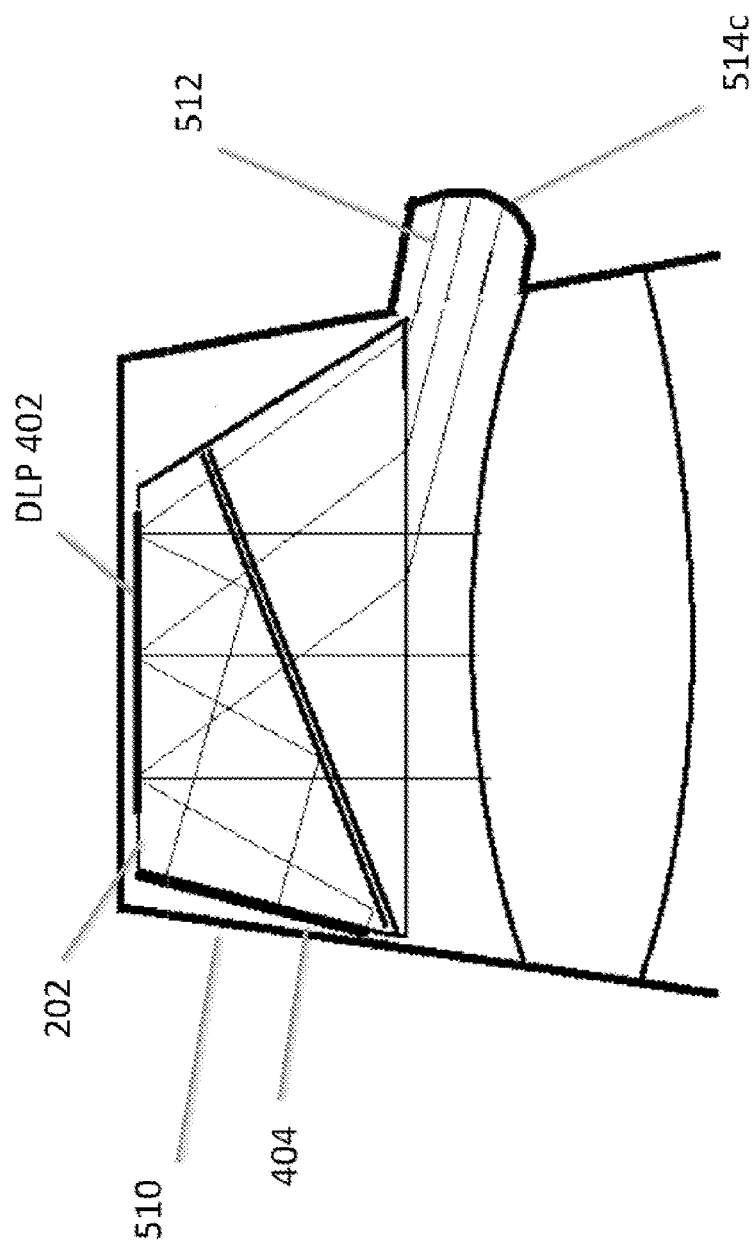
FIG. 5d illustrates an upper optical module and dark light trap according to the principles of the present invention.

FIG. 5*c* illustrates another embodiment with a light trap 514*b*. As can be seen in the illustration, the shape of the trap is configured to enhance internal reflections within the light trap 514*b* to increase the absorption of the dark light 512. FIG. 5*d* illustrates another embodiment with a light trap 514*c*. As can be seen in the illustration, the shape of the trap 514*c* is configured to enhance internal reflections to increase the absorption of the dark light 512.

FIG. 5*e* illustrates another embodiment of an upper optical module 202 with a dark light trap 514*d*. This embodiment of upper module 202 includes an off light reflection wedge 502, as illustrated and described in connection with the embodiment of FIGS. 5 and 5*a*. As can be seen in FIG. 5*e*, the light trap 514*d* is positioned along the optical path of the dark light 512. The dark light trap 514*d* may be configured as described in other embodiments herein. The embodiment of the light trap 514*d* illustrated in figure Se includes a black area on the side wall of the wedge, wherein the side wall is located substantially away from the optical axis of the image light 414. In addition, baffles 5252 may be added to one or more edges of the field lens 312 to block the view of the light trap 514*d* adjacent to the displayed image seen by the user.

Figure 6:
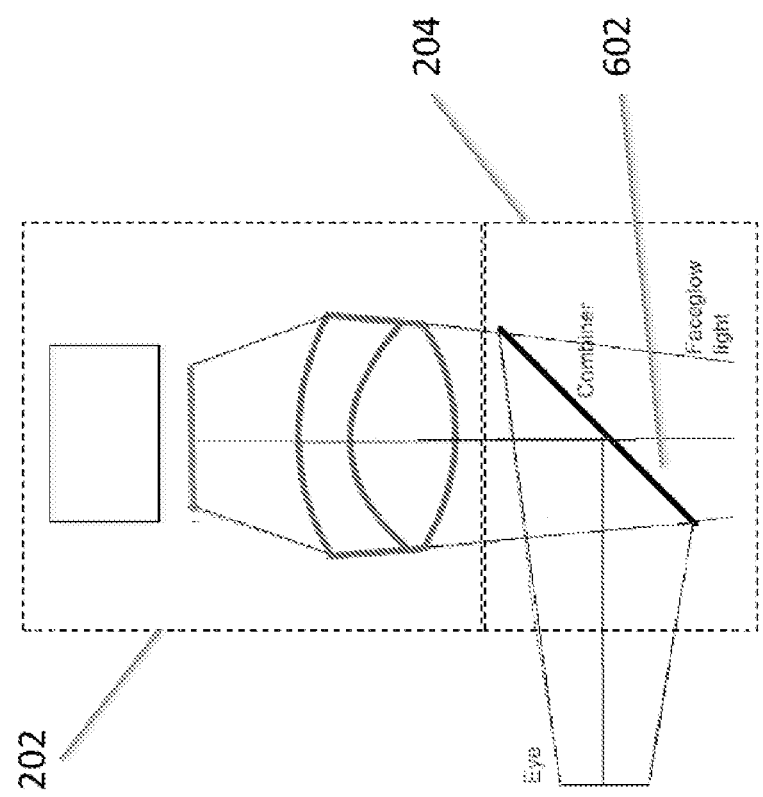
FIG. 6 illustrates upper and lower optical modules in accordance with the principles of the present invention.

FIG. 6 illustrates a combination of an upper optical module 202 with a lower optical module 204. In this embodiment, the image light projected from the upper optical module 202 may or may not be polarized. The image light is reflected off a flat combiner element 602 such that it is directed towards the user's eye. Wherein, the combiner element 602 is a partial mirror that reflects image light while transmitting a substantial portion of light from the environment so that the user can look through the combiner element and see the environment surrounding the HWC.

The combiner 602 may include a holographic pattern, to form a holographic mirror. If a monochrome image is desired, there may be a single wavelength reflection design for the holographic pattern on the surface of the combiner 602. If the intention is to have multiple colors reflected from the surface of the combiner 602, a multiple wavelength holographic mirror maybe included on the combiner surface. For example, in a three-color embodiment, where red, green and blue pixels are generated in the image light, the holographic mirror may be reflective to wavelengths substantially matching the wavelengths of the red, green and blue light provided by the light source. This configuration can be used as a wavelength specific mirror where pre-determined wavelengths of light from the image light are reflected to the user's eye. This configuration may also be made such that substantially all other wavelengths in the visible pass through the combiner element 602 so the user has a substantially clear view of the surroundings when looking through the combiner element 602. The transparency between the user's eye and the surrounding may be approximately 80% when using a combiner that is a holographic mirror. Wherein holographic mirrors can be made using lasers to produce interference patterns in the holographic material of the combiner where the wavelengths of the lasers correspond to the wavelengths of light that are subsequently reflected by the holographic mirror.

In another embodiment, the combiner element 602 may include a notch mirror comprised of a multilayer coated substrate wherein the coating is designed to substantially reflect the wavelengths of light provided by the light source and substantially transmit the remaining wavelengths in the visible spectrum. For example, in the case where red, green and blue light is provided by the light source to enable full color images to be provided to the user, the notch mirror is a tristimulus notch mirror wherein the multilayer coating is designed to reflect narrow bands of red, green and blue light that are matched to the what is provided by the light source and the remaining visible wavelengths are transmitted through the coating to enable a view of the environment through the combiner. In another example where monochrome images are provided to the user, the notch mirror is designed to reflect a single narrow band of light that is matched to the wavelength range of the light provided by the light source while transmitting the remaining visible wavelengths to enable a see-thru view of the environment. The combiner 602 with the notch mirror would operate, from the user's perspective, in a manner similar to the combiner that includes a holographic pattern on the combiner element 602.

The combiner, with the tristimulus notch mirror, would reflect the "on" pixels to the eye because of the match between the reflective wavelengths of the notch mirror and the color of the image light, and the wearer would be able to see with high clarity the surroundings. The transparency between the user's eye and the surrounding may be approximately 80% when using the tristimulus notch mirror. In addition, the image provided by the upper optical module 202 with the notch mirror combiner can provide higher contrast images than the holographic mirror combiner due to less scattering of the imaging light by the combiner.

Light can escape through the combiner 602 and may produce face glow as the light is generally directed downward onto the cheek of the user. When using a holographic mirror combiner or a tristimulus notch mirror combiner, the escaping light can be trapped to avoid face glow. In embodiments, if the image light is polarized before the combiner, a linear polarizer can be laminated, or otherwise associated, to the combiner, with the transmission axis of the polarizer oriented relative to the polarized image light so that any escaping image light is absorbed by the polarizer. In embodiments, the image light would be polarized to provide S polarized light to the combiner for better reflection. As a result, the linear polarizer on the combiner would be oriented to absorb S polarized light and pass P polarized light. This provides the preferred orientation of polarized sunglasses as well.

If the image light is unpolarized, a microlouvered film such as a privacy filter can be used to absorb the escaping image light while providing the user with a see-thru view of the environment. In this case, the absorbance or transmittance of the microlouvered film is dependent on the angle of the light. Where steep angle light is absorbed and light at less of an angle is transmitted. For this reason, in an embodiment, the combiner with the microlouver film is angled at greater than 45 degrees to the optical axis of the image light (e.g. the combiner can be oriented at 50 degrees so the image light from the file lens is incident on the combiner at an oblique angle.

Figure 7:
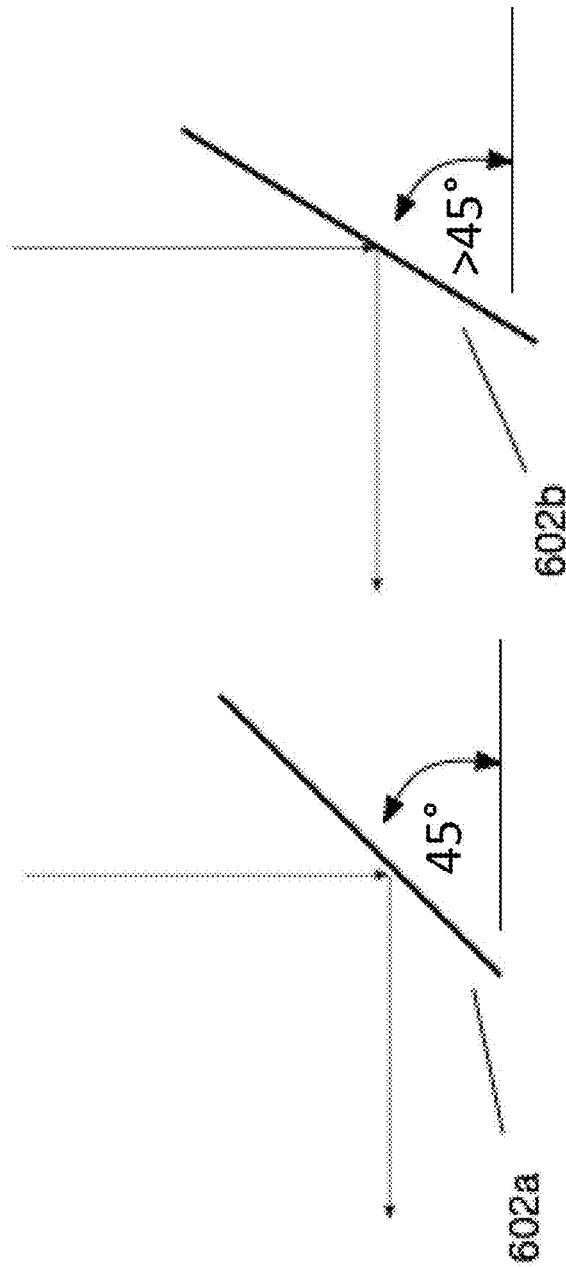
FIG. 7 illustrates angles of combiner elements in accordance with the principles of the present invention.

FIG. 7 illustrates an embodiment of a combiner element 602 at various angles when the combiner element 602 includes a holographic mirror. Normally, a mirrored surface reflects light at an angle equal to the angle that the light is incident to the mirrored surface. Typically, this necessitates that the combiner element be at 45 degrees, 602a, if the light is presented vertically to the combiner so the light can be reflected horizontally towards the wearer's eye. In embodiments, the incident light can be presented at angles other than vertical to enable the mirror surface to be oriented at other than 45 degrees, but in all cases wherein a mirrored surface is employed (including the tristimulus notch mirror described previously), the incident angle equals the reflected angle. As a result, increasing the angle of the combiner 602a requires that the incident image light be presented to the combiner 602a at a different angle which positions the upper optical module 202 to the left of the combiner as shown in FIG. 7. In contrast, a holographic mirror combiner, included in embodiments, can be made such that light is reflected at a different angle from the angle that the light is incident onto the holographic mirrored surface. This allows freedom to select the angle of the combiner element 602b independent of the angle of the incident image light and the angle of the light reflected into the wearer's eye. In embodiments, the angle of the combiner element 602b is greater than 45 degrees (shown in FIG. 7) as this allows a more laterally compact HWC design. The increased angle of the combiner element 602b decreases the front to back width of the lower optical module 204 and may allow for a thinner HWC display (i.e. the furthest element from the wearer's eye can be closer to the wearer's face).

Figure 8:
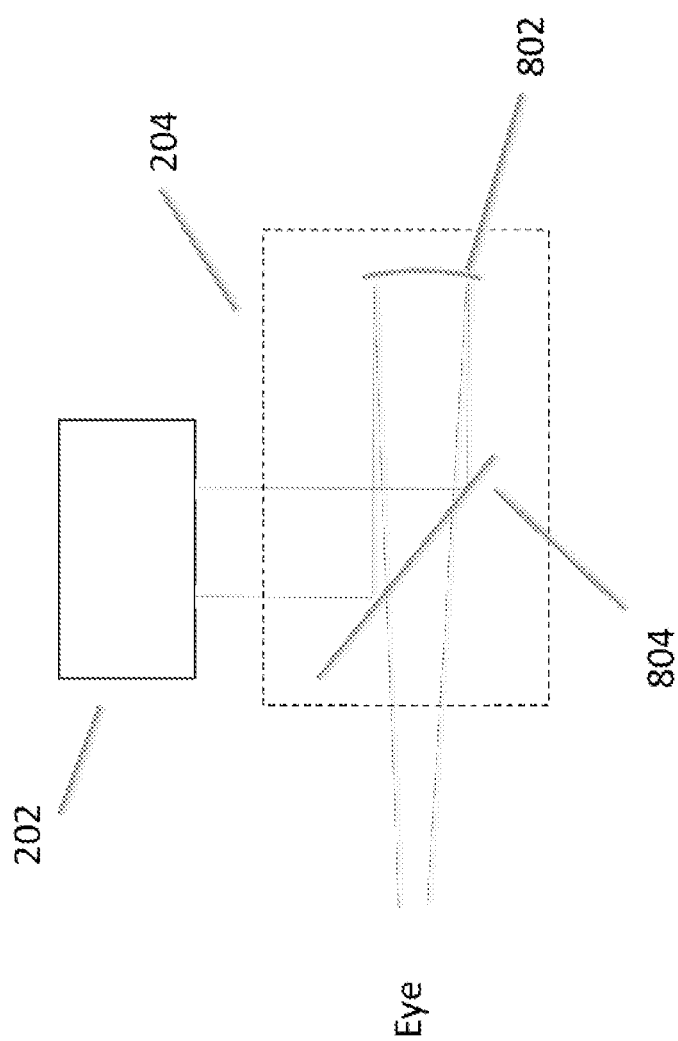
FIG. 8 illustrates upper and lower optical modules in accordance with the principles of the present invention.

FIG. 8 illustrates another embodiment of a lower optical module 204. In this embodiment, polarized image light provided by the upper optical module 202, is directed into the lower optical module 204. The image light reflects off a polarized mirror 804 and is directed to a focusing partially reflective mirror 802, which is adapted to reflect the polarized light. An optical element such as a ¼ wave film located between the polarized mirror 804 and the partially reflective mirror 802, is used to change the polarization state of the image light such that the light reflected by the partially reflective mirror 802 is transmitted by the polarized mirror 804 to present image light to the eye of the wearer. The user can also see through the polarized mirror 804 and the partially reflective mirror 802 to see the surrounding environment. As a result, the user perceives a combined image comprised of the displayed image light overlaid onto the see-thru view of the environment.

While many of the embodiments of the present invention have been referred to as upper and lower modules containing certain optical components, it should be understood that the image light and dark light production and management functions described in connection with the upper module may be arranged to direct light in other directions (e.g. upward, sideward, etc.). In embodiments, it may be preferred to mount the upper module 202 above the wearer's eye, in which case the image light would be directed downward. In other embodiments it may be preferred to produce light from the side of the wearer's eye, or from below the wearer's eye. In addition, the lower optical module is generally configured to deliver the image light to the wearer's eye and allow the wearer to see through the lower optical module, which may be accomplished through a variety of optical components.

Figure 8A:
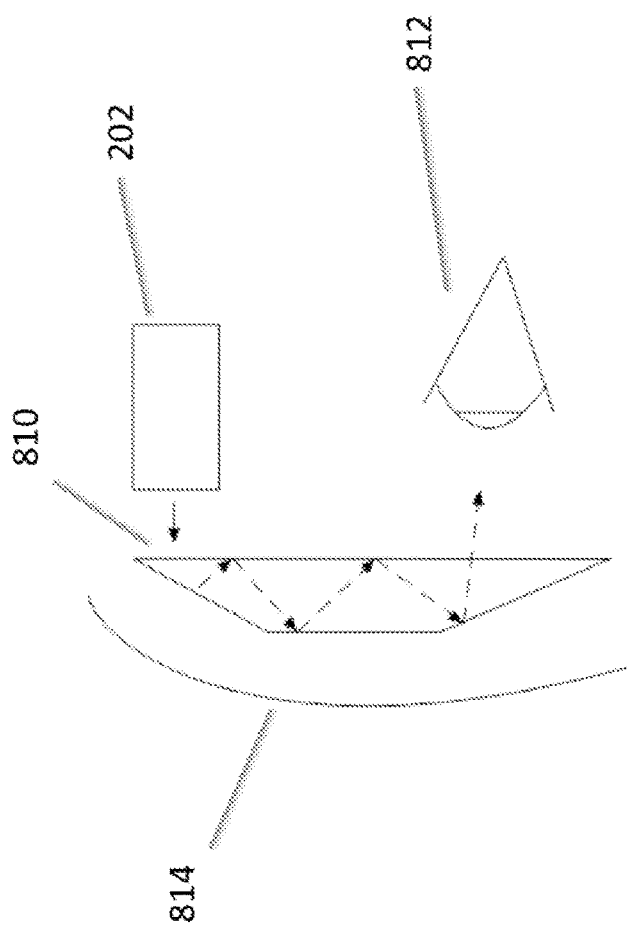
FIG. 8a illustrates upper and lower optical modules in accordance with the principles of the present invention.

FIG. 8a illustrates an embodiment of the present invention where the upper optical module 202 is arranged to direct image light into a TIR waveguide 810. In this embodiment, the upper optical module 202 is positioned above the wearer's eye 812 and the light is directed horizontally into the TIR waveguide 810. The TIR waveguide is designed to internally reflect the image light in a series of downward TIR reflections until it reaches the portion in front of the wearer's eye, where the light passes out of the TIR waveguide 812 into the wearer's eye. In this embodiment, an outer shield 814 is positioned in front of the TIR waveguide 810.

FIG. 8b illustrates an embodiment of the present invention where the upper optical module 202 is arranged to direct image light into a TIR waveguide 818. In this embodiment, the upper optical module 202 is arranged on the side of the TIR waveguide 818. For example, the upper optical module may be positioned in the arm or near the arm of the HWC when configured as a pair of head worn glasses. The TIR waveguide 818 is designed to internally reflect the image light in a series of TIR reflections until it reaches the portion in front of the wearer's eye, where the light passes out of the TIR waveguide 812 into the wearer's eye.

Figure 8C:
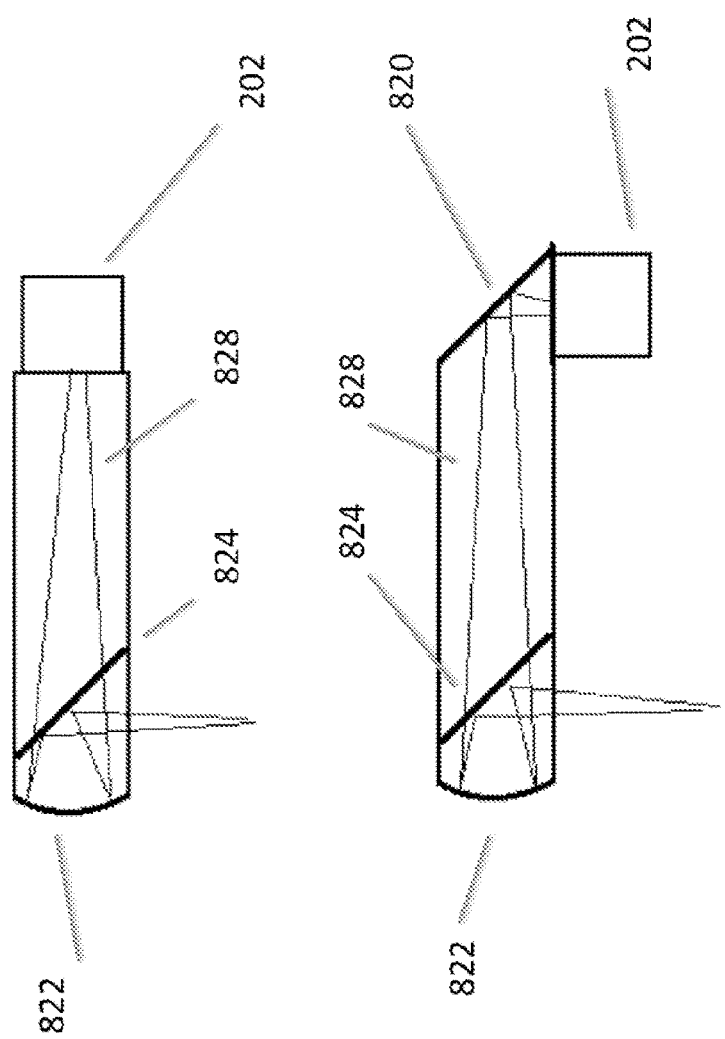
FIG. 8c illustrates upper and lower optical modules in accordance with the principles of the present invention.

FIG. 8c illustrates yet further embodiments of the present invention where an upper optical module 202 is directing polarized image light into an optical guide 828 where the image light passes through a polarized reflector 824, changes polarization state upon reflection of the optical element 822 which includes a ¼ wave film for example and then is reflected by the polarized reflector 824 towards the wearer's eye, due to the change in polarization of the image light. The upper optical module 202 may be positioned to direct light to a mirror 820, to position the upper optical module 202 laterally, in other embodiments, the upper optical module 202 may direct the image light directly towards the polarized reflector 824. It should be understood that the present invention comprises other optical arrangements intended to direct image light into the wearer's eye.

Figure 9:
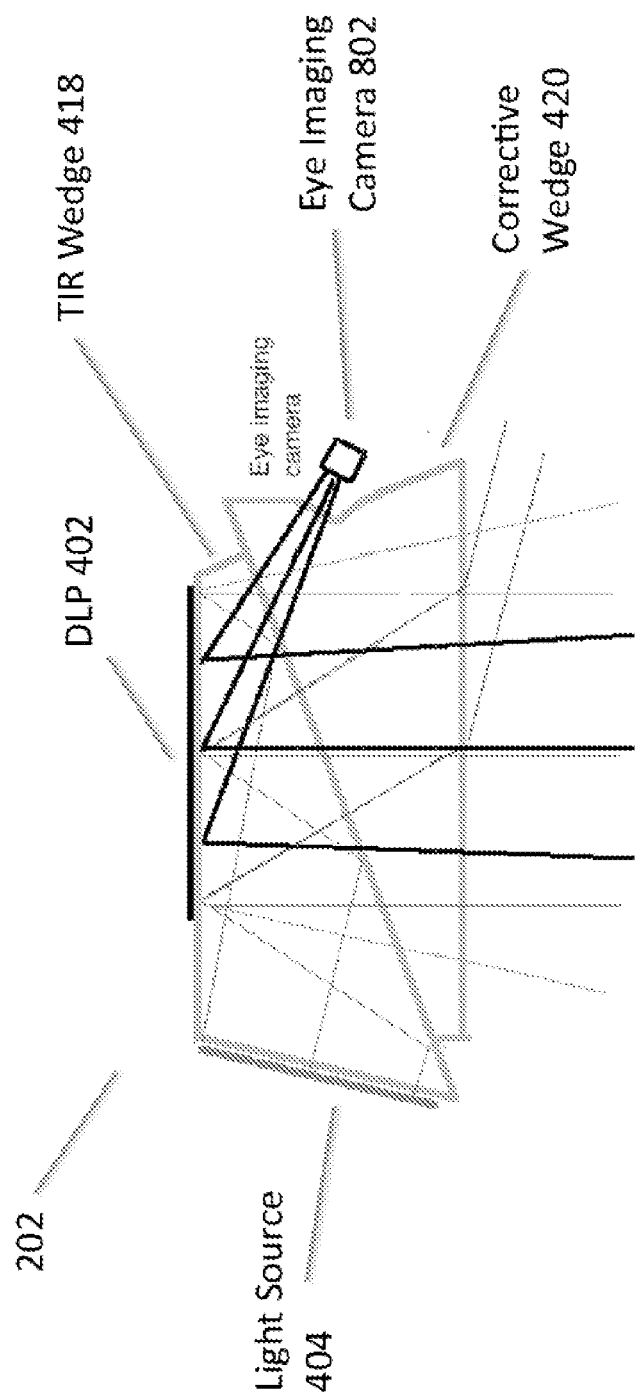
FIG. 9 illustrates an eye imaging system in accordance with the principles of the present invention.

Another aspect of the present invention relates to eye imaging. In embodiments, a camera is used in connection with an upper optical module 202 such that the wearer's eye can be imaged using pixels in the "off" state on the DLP. FIG. 9 illustrates a system where the eye imaging camera 802 is mounted and angled such that the field of view of the eye imaging camera 802 is redirected toward the wearer's eye by the mirror pixels of the DLP 402 that are in the "off" state. In this way, the eye imaging camera 802 can be used to image the wearer's eye along the same optical axis as the displayed image that is presented to the wearer. Wherein, image light that is presented to the wearer's eye illuminates the wearer's eye so that the eye can be imaged by the eye imaging camera 802. In the process, the light reflected by the eye passes back though the optical train of the lower optical module 204 and a portion of the upper optical module to where the light is reflected by the "off" pixels of the DLP 402 toward the eye imaging camera 802.

In embodiments, the eye imaging camera may image the wearer's eye at a moment in time where there are enough "off" pixels to achieve the required eye image resolution. In another embodiment, the eye imaging camera collects eye image information from "off" pixels over time and forms a time lapsed image. In another embodiment, a modified image is presented to the user wherein enough "off" state pixels are included that the camera can obtain the desired resolution and brightness for imaging the wearer's eye and the eye image capture is synchronized with the presentation of the modified image.

The eye imaging system may be used for security systems. The HWC may not allow access to the HWC or other system if the eye is not recognized (e.g. through eye characteristics including retina or iris characteristics, etc.). The HWC may be used to provide constant security access in some embodiments. For example, the eye security confirmation may be a continuous, near-continuous, real-time, quasi real-time, periodic, etc. process so the wearer is effectively constantly being verified as known. In embodiments, the HWC may be worn and eye security tracked for access to other computer systems.

The eye imaging system may be used for control of the HWC. For example, a blink, wink, or particular eye movement may be used as a control mechanism for a software application operating on the HWC or associated device.

The eye imaging system may be used in a process that determines how or when the HWC 102 delivers digitally displayed content to the wearer. For example, the eye imaging system may determine that the user is looking in a direction and then HWC may change the resolution in an area of the display or provide some content that is associated with something in the environment that the user may be looking at. Alternatively, the eye imaging system may identify different user's and change the displayed content or enabled features provided to the user. User's may be identified from a database of users eye characteristics either located on the HWC 102 or remotely located on the network 110 or on a server 112. In addition, the HWC may identify a primary user or a group of primary users from eye characteristics wherein the primary user(s) are provided with an enhanced set of features and all other user's are provided with a different set of features. Thus in this use case, the HWC 102 uses identified eye characteristics to either enable features or not and eye characteristics need only be analyzed in comparison to a relatively small database of individual eye characteristics.

FIG. 10 illustrates a light source that may be used in association with the upper optics module 202 (e.g. polarized light source if the light from the solid state light source is polarized such as polarized light source 302 and 458), and light source 404. In embodiments, to provide a uniform surface of light 1008 to be directed into the upper optical module 202 and towards the DLP of the upper optical module, either directly or indirectly, the solid state light source 1002 may be projected into a backlighting optical system 1004. The solid state light source 1002 may be one or more LEDs, laser diodes, OLEDs. In embodiments, the backlighting optical system 1004 includes an extended section with a length/distance ratio of greater than 3, wherein the light undergoes multiple reflections from the sidewalls to mix of homogenize the light as supplied by the solid state light source 1002. The backlighting optical system 1004 can also include structures on the surface opposite (on the left side as shown in FIG. 10) to where the uniform light 1008 exits the backlight 1004 to change the direction of the light toward the DLP 302 and the reflective polarizer 310 or the DLP 402 and the TIR wedge 418. The backlighting optical system 1004 may also include structures to collimate the uniform light 1008 to provide light to the DLP with a smaller angular distribution or narrower cone angle. Diffusers or polarizers can be used on the entrance or exit surface of the backlighting optical system. Diffusers can be used to spread or uniformize the exiting light from the backlight to improve the uniformity or increase the angular spread of the uniform light 1008. Elliptical diffusers that diffuse the light more in some directions and less in others can be used to improve the uniformity or spread of the uniform light 1008 in directions orthogonal to the optical axis of the uniform light 1008. Linear polarizers can be used to convert unpolarized light as supplied by the solid state light source 1002 to polarized light so the uniform light 1008 is polarized with a desired polarization state. A reflective polarizer can be used on the exit surface of the backlight 1004 to polarize the uniform light 1008 to the desired polarization state, while reflecting the other polarization state back into the backlight where it is recycled by multiple reflections within the backlight 1004 and at the solid state light source 1002. Therefore by including a reflective polarizer at the exit surface of the backlight 1004, the efficiency of the polarized light source is improved.

FIGS. 10a and 10b show illustrations of structures in backlight optical systems 1004 that can be used to change the direction of the light provided to the entrance face 1045 by the light source and then collimates the light in a direction lateral to the optical axis of the exiting uniform light 1008. Structure 1060 includes an angled sawtooth pattern in a transparent waveguide wherein the left edge of each sawtooth clips the steep angle rays of light thereby limiting the angle of the light being redirected. The steep surface at the right (as shown) of each sawtooth then redirects the light so that it reflects off the left angled surface of each sawtooth and is directed toward the exit surface 1040. The sawtooth surfaces shown on the lower surface in FIGS. 10a and 10b, can be smooth and coated (e.g. with an aluminum coating or a dielectric mirror coating) to provide a high level of reflectivity without scattering. Structure 1050 includes a curved face on the left side (as shown) to focus the rays after they pass through the exit surface 1040, thereby providing a mechanism for collimating the uniform light 1008. In a further embodiment, a diffuser can be provided between the solid state light source 1002 and the entrance face 1045 to homogenize the light provided by the solid state light source 1002. In yet a further embodiment, a polarizer can be used between the diffuser and the entrance face 1045 of the backlight 1004 to provide a polarized light source. Because the sawtooth pattern provides smooth reflective surfaces, the polarization state of the light can be preserved from the entrance face 1045 to the exit face 1040. In this embodiment, the light entering the backlight from the solid state light source 1002 passes through the polarizer so that it is polarized with the desired polarization state. If the polarizer is an absorptive linear polarizer, the light of the desired polarization state is transmitted while the light of the other polarization state is absorbed. If the polarizer is a reflective polarizer, the light of the desired polarization state is transmitted into the backlight 1004 while the light of the other polarization state is reflected back into the solid state light source 1002 where it can be recycled as previously described, to increase the efficiency of the polarized light source.

Figure 11A:
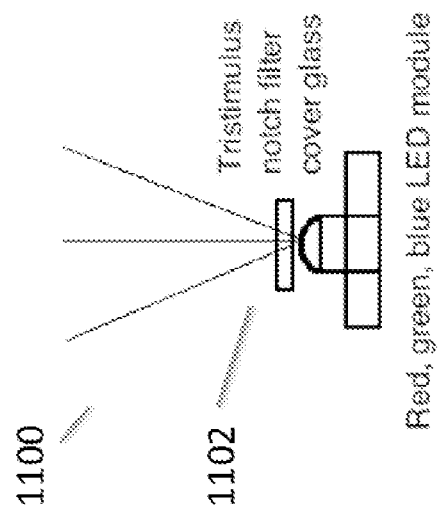
FIGS. 11a to 11d illustrate light source and filters in accordance with the principles of the present invention.
Figure 11B:
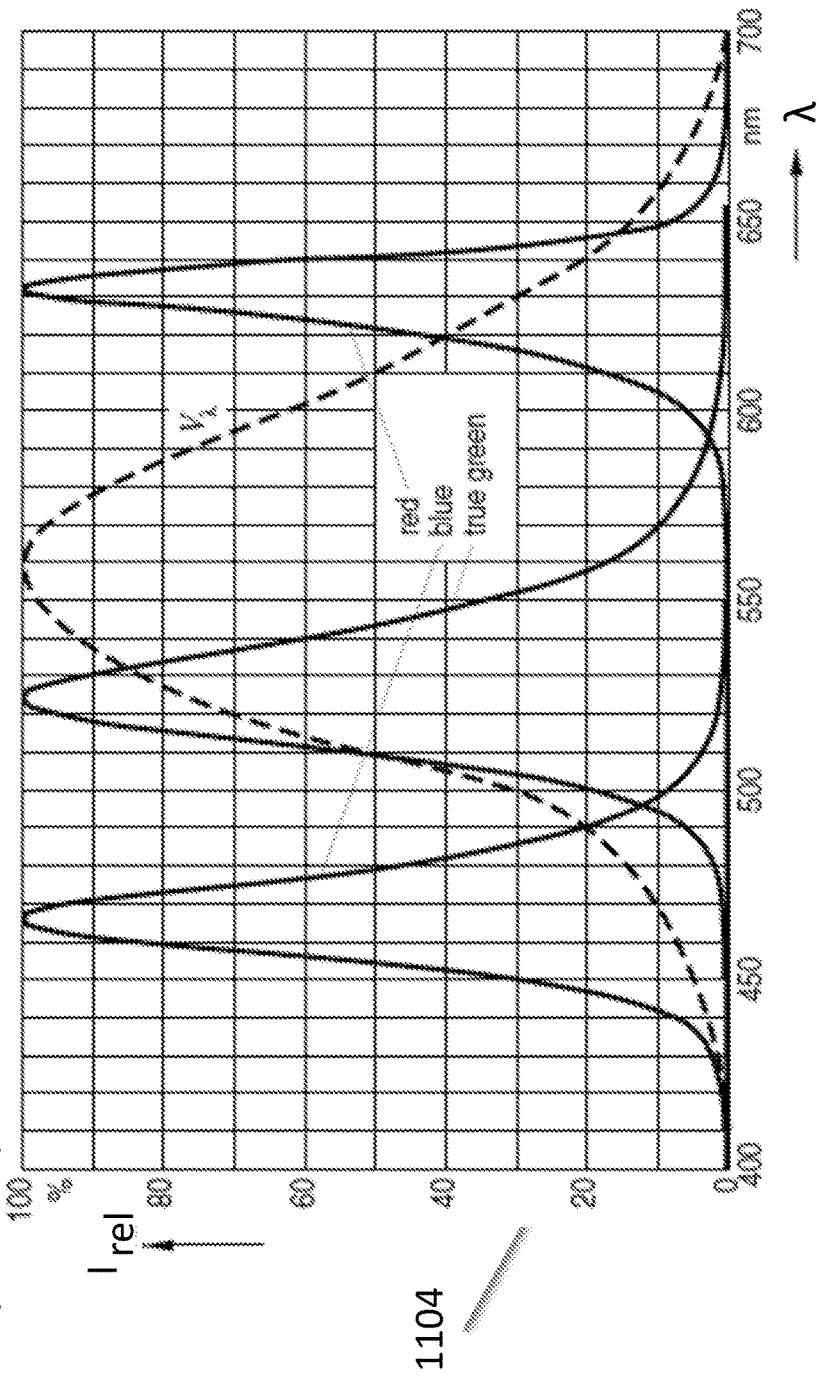
Figure 11C:
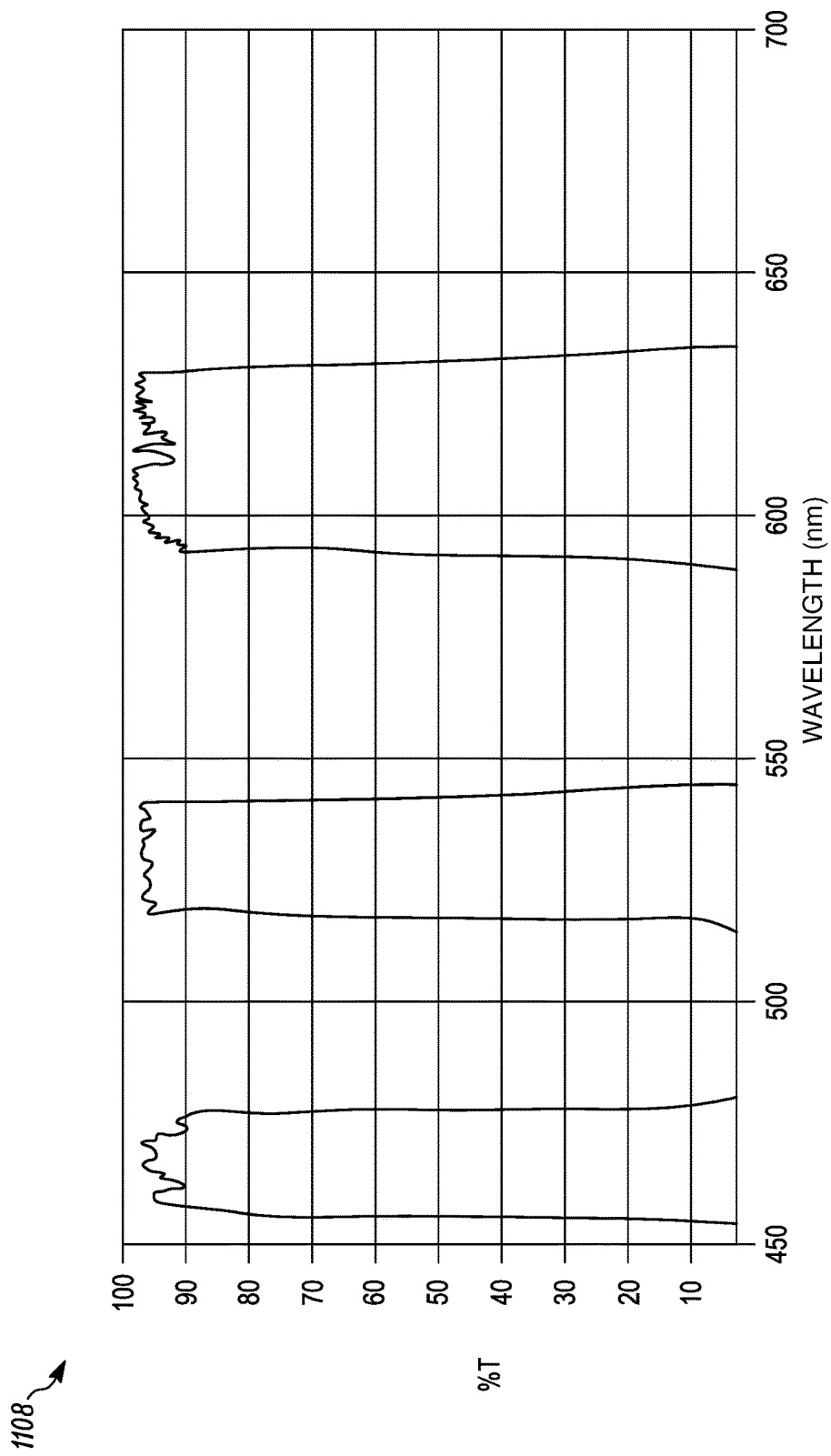
Figure 11D:
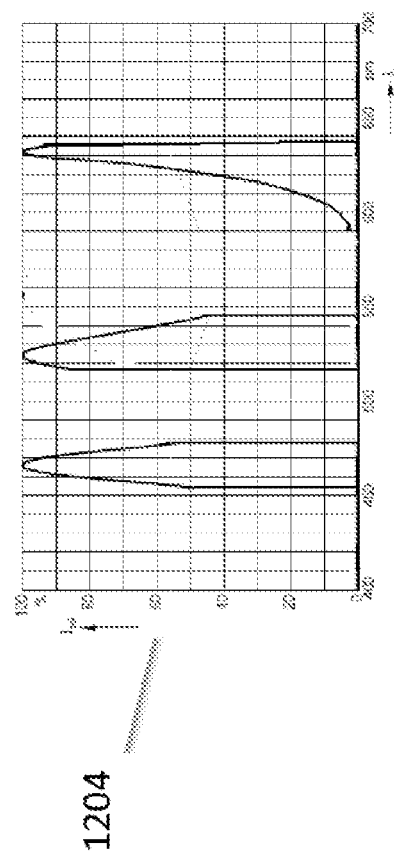

FIG. 11a illustrates a light source 1100 that may be used in association with the upper optics module 202. In embodiments, the light source 1100 may provide light to a backlighting optical system 1004 as described above in connection with FIG. 10. In embodiments, the light source 1100 includes a tristimulus notch filter 1102. The tristimulus notch filter 1102 has narrow band pass filters for three wavelengths, as indicated in FIG. 11c in a transmission graph 1108. The graph shown in FIG. 11b, as 1104 illustrates an output of three different colored LEDs. One can see that the bandwidths of emission are narrow, but they have long tails. The tristimulus notch filter 1102 can be used in connection with such LEDs to provide a light source 1100 that emits narrow filtered wavelengths of light as shown in FIG. 11d as the transmission graph 1110. Wherein the clipping effects of the tristimulus notch filter 1102 can be seen to have cut the tails from the LED emission graph 1104 to provide narrower wavelength bands of light to the upper optical module 202. The light source 1100 can be used in connection with a combiner 602 with a holographic mirror or tristimulus notch mirror to provide narrow bands of light that are reflected toward the wearer's eye with less waste light that does not get reflected by the combiner, thereby improving efficiency and reducing escaping light that can cause faceglow.

Figure 12A:
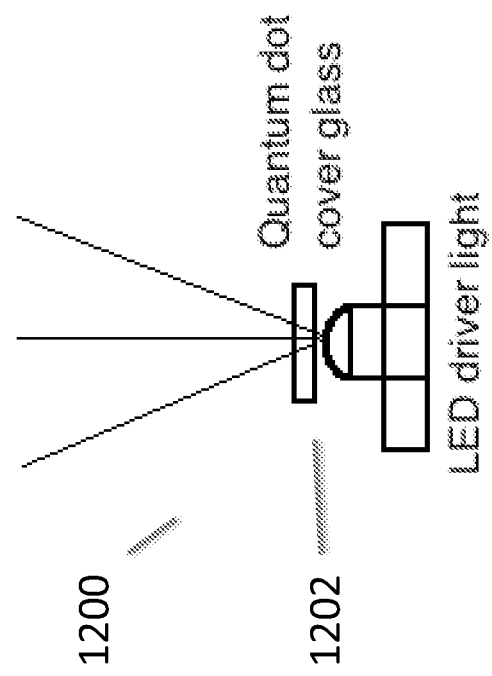
FIGS. 12a to 12c illustrate light source and quantum dot systems in accordance with the principles of the present invention.
Figure 12B:
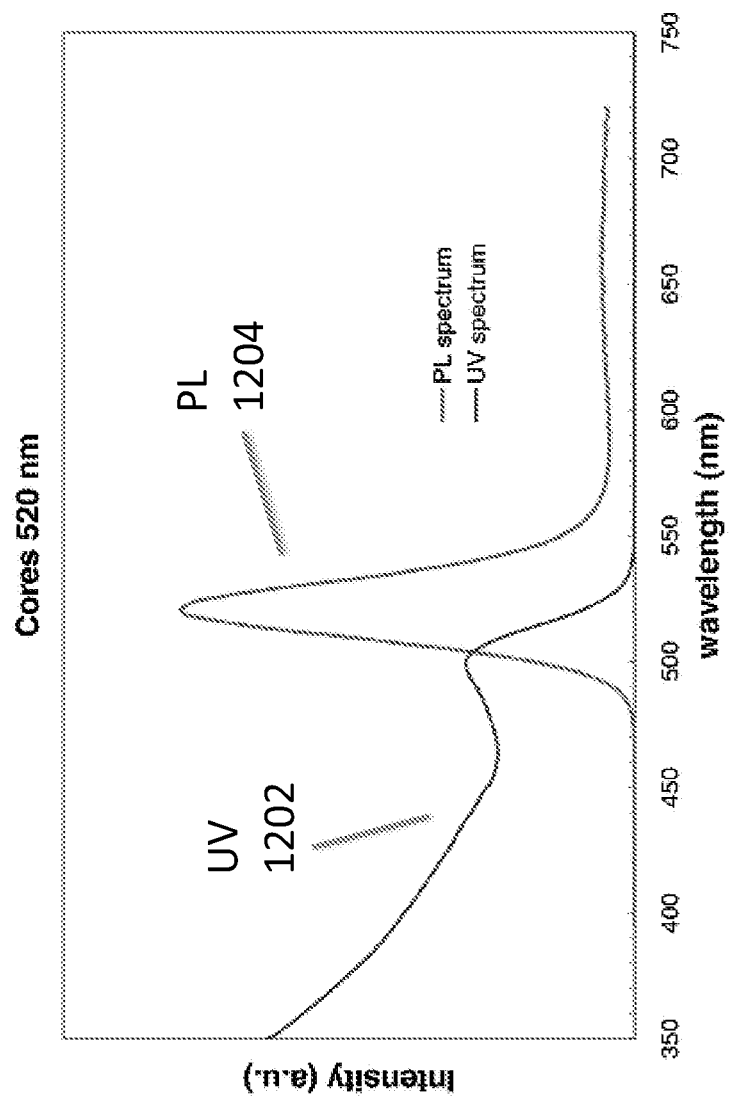
Figure 12C:
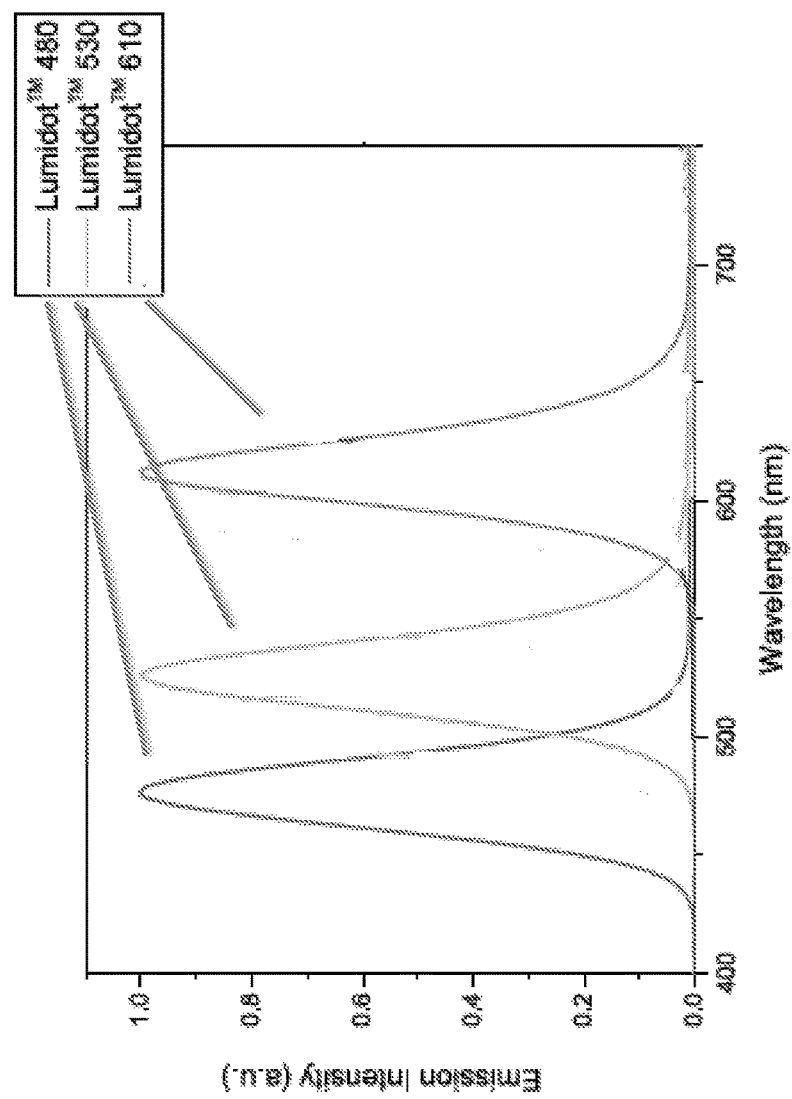

FIG. 12a illustrates another light source 1200 that may be used in association with the upper optics module 202. In embodiments, the light source 1200 may provide light to a backlighting optical system 1004 as described above in connection with FIG. 10. In embodiments, the light source 1200 includes a quantum dot cover glass 1202. Where the quantum dots absorb light of a shorter wavelength and emit light of a longer wavelength (FIG. 12b shows an example wherein a UV spectrum 1202 applied to a quantum dot results in the quantum dot emitting a narrow band shown as a PL spectrum 1204) that is dependent on the material makeup and size of the quantum dot. As a result, quantum dots in the quantum dot cover glass 1202 can be tailored to provide one or more bands of narrow bandwidth light (e.g. red, green and blue emissions dependent on the different quantum dots included as illustrated in the graph shown in FIG. 12c where three different quantum dots are used. In embodiments, the LED driver light emits UV light, deep blue or blue light. For sequential illumination of different colors, multiple light sources 1200 would be used where each light source 1200 would include a quantum dot cover glass 1202 with a quantum dot selected to emit at one of the desired colors. The light source 1100 can be used in connection with a combiner 602 with a holographic mirror or tristimulus notch mirror to provide narrow transmission bands of light that are reflected toward the wearer's eye with less waste light that does not get reflected.

Another aspect of the present invention relates to the generation of peripheral image lighting effects for a person wearing a HWC. In embodiments, a solid state lighting system (e.g. LED, OLED, etc), or other lighting system, may be included inside the optical elements of an lower optical module 204. The solid state lighting system may be arranged such that lighting effects outside of a field of view (FOV) of the presented digital content is presented to create an emersive effect for the person wearing the HWC. To this end, the lighting effects may be presented to any portion of the HWC that is visible to the wearer. The solid state lighting system may be digitally controlled by an integrated processor on the HWC. In embodiments, the integrated processor will control the lighting effects in coordination with digital content that is presented within the FOV of the HWC. For example, a movie, picture, game, or other content, may be displayed or playing within the FOV of the HWC. The content may show a bomb blast on the right side of the FOV and at the same moment, the solid state lighting system inside of the upper module optics may flash quickly in concert with the FOV image effect. The effect may not be fast, it may be more persistent to indicate, for example, a general glow or color on one side of the user. The solid state lighting system may be color controlled, with red, green and blue LEDs, for example, such that color control can be coordinated with the digitally presented content within the field of view.

FIG. 13a illustrates optical components of a lower optical module 204 together with an outer lens 1302. FIG. 13a also shows an embodiment including effects LED's 1308a and 1308b. FIG. 13a illustrates image light 1312, as described herein elsewhere, directed into the upper optical module where it will reflect off of the combiner element 1304, as described herein elsewhere. The combiner element 1304 in this embodiment is angled towards the wearer's eye at the top of the module and away from the wearer's eye at the bottom of the module, as also illustrated and described in connection with FIG. 8 (e.g. at a 45 degree angle). The image light 1312 provided by an upper optical module 202 (not shown in FIG. 13a) reflects off of the combiner element 1304 towards the collimating mirror 1310, away from the wearer's eye, as described herein elsewhere. The image light 1312 then reflects and focuses off of the collimating mirror 1304, passes back through the combiner element 1304, and is directed into the wearer's eye. The wearer can also view the surrounding environment through the transparency of the combiner element 1304, collimating mirror 1310, and outer lens 1302 (if it is included). As described herein elsewhere, various surfaces are polarized to create the optical path for the image light and to provide transparency of the elements such that the wearer can view the surrounding environment. The wearer will generally perceive that the image light forms an image in the FOV 1305. In embodiments, the outer lens 1302 may be included. The outer lens 1302 is an outer lens that may or may not be corrective and it may be designed to conceal the lower optical module components in an effort to make the HWC appear to be in a form similar to standard glasses or sunglasses.

In the embodiment illustrated in FIG. 13a, the effects LEDs 1308a and 1308b are positioned at the sides of the combiner element 1304 and the outer lens 1302 and/or the collimating mirror 1310. In embodiments, the effects LEDs 1308a are positioned within the confines defined by the combiner element 1304 and the outer lens 1302 and/or the collimating mirror. The effects LEDs 1308a and 1308b are also positioned outside of the FOV 1305. In this arrangement, the effects LEDs 1308a and 1308b can provide lighting effects within the lower optical module outside of the FOV 1305. In embodiments the light emitted from the effects LEDs 1308a and 1308b may be polarized such that the light passes through the combiner element 1304 toward the wearer's eye and does not pass through the outer lens 1302 and/or the collimating mirror 1310. This arrangement provides peripheral lighting effects to the wearer in a more private setting by not transmitting the lighting effects through the front of the HWC into the surrounding environment. However, in other embodiments, the effects LEDs 1308a and 1308b may be unpolarized so the lighting effects provided are made to be purposefully viewable by others in the environment for entertainment such as giving the effect of the wearer's eye glowing in correspondence to the image content being viewed by the wearer.

Figure 13B:
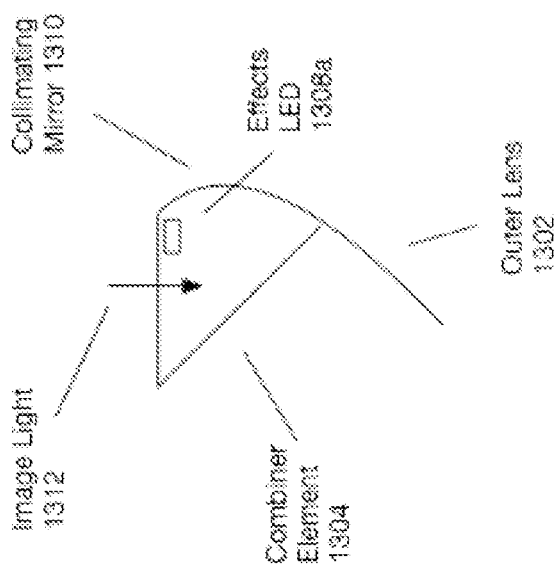

FIG. 13b illustrates a cross section of the embodiment described in connection with FIG. 13a. As illustrated, the effects LED 1308a is located in the upper-front area inside of the optical components of the lower optical module. It should be understood that the effects LED 1308a position in the described embodiments is only illustrative and alternate placements are encompassed by the present invention. Additionally, in embodiments, there may be one or more effects LEDs 1308a in each of the two sides of HWC to provide peripheral lighting effects near one or both eyes of the wearer.

FIG. 13c illustrates an embodiment where the combiner element 1304 is angled away from the eye at the top and towards the eye at the bottom (e.g. in accordance with the holographic or notch filter embodiments described herein). In this embodiment, the effects LED 1308a is located on the outer lens 1302 side of the combiner element 1304 to provide a concealed appearance of the lighting effects. As with other embodiments, the effects LED 1308a of FIG. 13c may include a polarizer such that the emitted light can pass through a polarized element associated with the combiner element 1304 and be blocked by a polarized element associated with the outer lens 1302.

Another aspect of the present invention relates to the mitigation of light escaping from the space between the wearer's face and the HWC itself. Another aspect of the present invention relates to maintaining a controlled lighting environment in proximity to the wearer's eyes. In embodiments, both the maintenance of the lighting environment and the mitigation of light escape are accomplished by including a removable and replaceable flexible shield for the HWC. Wherein the removable and replaceable shield can be provided for one eye or both eyes in correspondence to the use of the displays for each eye. For example, in a night vision application, the display to only one eye could be used for night vision while the display to the other eye is turned off to provide good see-thru when moving between areas where visible light is available and dark areas where night vision enhancement is needed.

FIG. 14a illustrates a removable and replaceable flexible eye cover 1402 with an opening 1408 that can be attached and removed quickly from the HWC 102 through the use of magnets. Other attachment methods may be used, but for illustration of the present invention we will focus on a magnet implementation. In embodiments, magnets may be included in the eye cover 1402 and magnets of an opposite polarity may be included (e.g. embedded) in the frame of the HWC 102. The magnets of the two elements would attract quite strongly with the opposite polarity configuration. In another embodiment, one of the elements may have a magnet and the other side may have metal for the attraction. In embodiments, the eye cover 1402 is a flexible elastomeric shield. In embodiments, the eye cover 1402 may be an elastomeric bellows design to accommodate flexibility and more closely align with the wearer's face. FIG. 14b illustrates a removable and replaceable flexible eye cover 1404 that is adapted as a single eye cover. In embodiments, a single eye cover may be used for each side of the HWC to cover both eyes of the wearer. In embodiments, the single eye cover may be used in connection with a HWC that includes only one computer display for one eye. These configurations prevent light that is generated and directed generally towards the wearer's face by covering the space between the wearer's face and the HWC. The opening 1408 allows the wearer to look through the opening 1408 to view the displayed content and the surrounding environment through the front of the HWC. The image light in the lower optical module 204 can be prevented from emitting from the front of the HWC through internal optics polarization schemes, as described herein, for example.

Figure 14C:
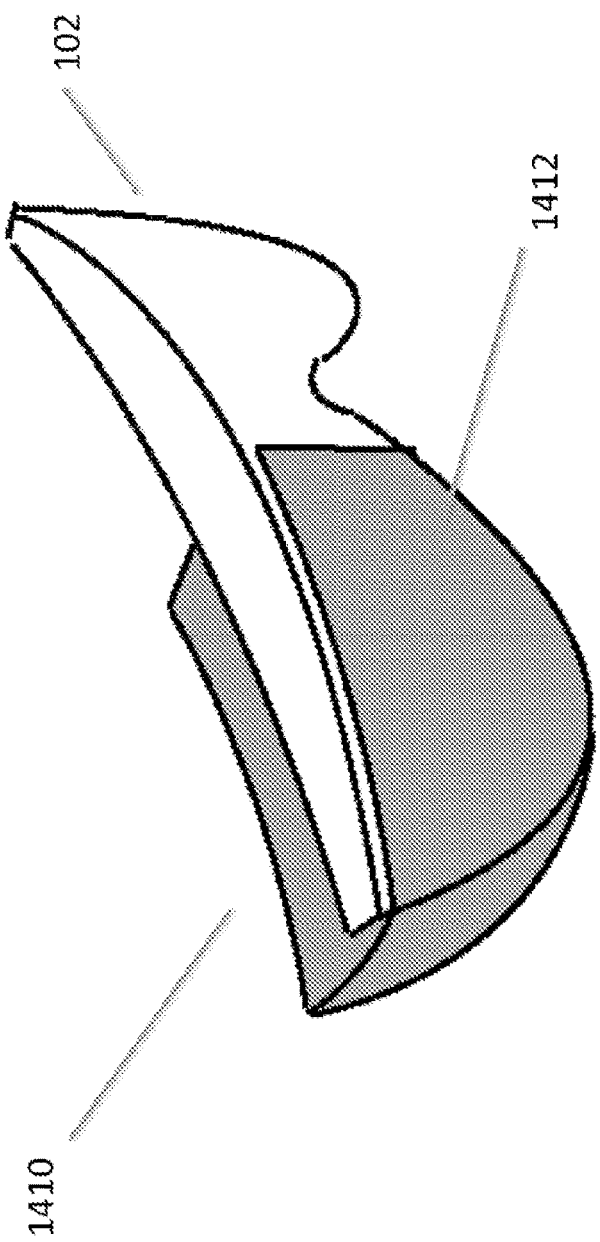

FIG. 14c illustrates another embodiment of a light suppression system. In this embodiment, the eye cover 1410 may be similar to the eye cover 1402, but eye cover 1410 includes a front light shield 1412. The front light shield 1412 may be opaque to prevent light from escaping the front lens of the HWC. In other embodiments, the front light shield 1412 is polarized to prevent light from escaping the front lens. In a polarized arrangement, in embodiments, the internal optical elements of the HWC (e.g. of the lower optical module 204) may polarize light transmitted towards the front of the HWC and the front light shield 1412 may be polarized to prevent the light from transmitting through the front light shield 1412.

In embodiments, an opaque front light shield 1412 may be included and the digital content may include images of the surrounding environment such that the wearer can visualize the surrounding environment. One eye may be presented with night vision environmental imagery and this eye's surrounding environment optical path may be covered using an opaque front light shield 1412. In other embodiments, this arrangement may be associated with both eyes.

Another aspect of the present invention relates to automatically configuring the lighting system(s) used in the HWC 102. In embodiments, the display lighting and/or effects lighting, as described herein, may be controlled in a manner suitable for when an eye cover 1408 is attached or removed from the HWC 102. For example, at night, when the light in the environment is low, the lighting system(s) in the HWC may go into a low light mode to further control any amounts of stray light escaping from the HWC and the areas around the HWC. Covert operations at night, while using night vision or standard vision, may require a solution which prevents as much escaping light as possible so a user may clip on the eye cover(s) 1408 and then the HWC may go into a low light mode. The low light mode may, in some embodiments, only go into a low light mode when the eye cover 1408 is attached if the HWC identifies that the environment is in low light conditions (e.g. through environment light level sensor detection). In embodiments, the low light level may be determined to be at an intermediate point between full and low light dependent on environmental conditions.

Another aspect of the present invention relates to automatically controlling the type of content displayed in the HWC when eye covers 1408 are attached or removed from the HWC. In embodiments, when the eye cover(s) 1408 is attached to the HWC, the displayed content may be restricted in amount or in color amounts. For example, the display(s) may go into a simple content delivery mode to restrict the amount of information displayed. This may be done to reduce the amount of light produced by the display(s). In an embodiment, the display(s) may change from color displays to monochrome displays to reduce the amount of light produced. In an embodiment, the monochrome lighting may be red to limit the impact on the wearer's eyes to maintain an ability to see better in the dark.

Referring to FIG. 15, we now turn to describe a particular external user interface 104, referred to generally as a pen 1500. The pen 1500 is a specially designed external user interface 104 and can operate as a user interface, such as to many different styles of HWC 102. The pen 1500 generally follows the form of a conventional pen, which is a familiar user handled device and creates an intuitive physical interface for many of the operations to be carried out in the HWC system 100. The pen 1500 may be one of several user interfaces 104 used in connection with controlling operations within the HWC system 100. For example, the HWC 102 may watch for and interpret hand gestures 116 as control signals, where the pen 1500 may also be used as a user interface with the same HWC 102. Similarly, a remote keyboard may be used as an external user interface 104 in concert with the pen 1500. The combination of user interfaces or the use of just one control system generally depends on the operation(s) being executed in the HWC's system 100.

While the pen 1500 may follow the general form of a conventional pen, it contains numerous technologies that enable it to function as an external user interface 104. FIG. 15 illustrates technologies comprised in the pen 1500. As can be seen, the pen 1500 may include a camera 1508, which is arranged to view through lens 1502. The camera may then be focused, such as through lens 1502, to image a surface upon which a user is writing or making other movements to interact with the HWC 102. There are situations where the pen 1500 will also have an ink, graphite, or other system such that what is being written can be seen on the writing surface. There are other situations where the pen 1500 does not have such a physical writing system so there is no deposit on the writing surface, where the pen would only be communicating data or commands to the HWC 102. The lens configuration is described in greater detail herein. The function of the camera is to capture information from an unstructured writing surface such that pen strokes can be interpreted as intended by the user. To assist in the predication of the intended stroke path, the pen 1500 may include a sensor, such as an IMU 1512. Of course, the IMU could be included in the pen 1500 in its separate parts (e.g. gyro, accelerometer, etc.) or an IMU could be included as a single unit. In this instance, the IMU 1512 is used to measure and predict the motion of the pen 1500. In turn, the integrated microprocessor 1510 would take the IMU information and camera information as inputs and process the information to form a prediction of the pen tip movement.

The pen 1500 may also include a pressure monitoring system 1504, such as to measure the pressure exerted on the lens 1502. As will be described in greater detail herein, the pressure measurement can be used to predict the user's intention for changing the weight of a line, type of a line, type of brush, click, double click, and the like. In embodiments, the pressure sensor may be constructed using any force or pressure measurement sensor located behind the lens 1502, including for example, a resistive sensor, a current sensor, a capacitive sensor, a voltage sensor such as a piezoelectric sensor, and the like.

The pen 1500 may also include a communications module 1518, such as for bi-directional communication with the HWC 102. In embodiments, the communications module 1518 may be a short distance communication module (e.g. Bluetooth). The communications module 1518 may be security matched to the HWC 102. The communications module 1518 may be arranged to communicate data and commands to and from the microprocessor 1510 of the pen 1500. The microprocessor 1510 may be programmed to interpret data generated from the camera 1508, IMU 1512, and pressure sensor 1504, and the like, and then pass a command onto the HWC 102 through the communications module 1518, for example. In another embodiment, the data collected from any of the input sources (e.g. camera 1508, IMU 1512, pressure sensor 1504) by the microprocessor may be communicated by the communication module 1518 to the HWC 102, and the HWC 102 may perform data processing and prediction of the user's intention when using the pen 1500. In yet another embodiment, the data may be further passed on through a network 110 to a remote device 112, such as a server, for the data processing and prediction. The commands may then be communicated back to the HWC 102 for execution (e.g. display writing in the glasses display, make a selection within the UI of the glasses display, control a remote external device 112, control a local external device 108), and the like. The pen may also include memory 1514 for long or short term uses.

The pen 1500 may also include a number of physical user interfaces, such as quick launch buttons 1522, a touch sensor 1520, and the like. The quick launch buttons 1522 may be adapted to provide the user with a fast way of jumping to a software application in the HWC system 100. For example, the user may be a frequent user of communication software packages (e.g. email, text, Twitter, Instagram, Facebook, Google+, and the like), and the user may program a quick launch button 1522 to command the HWC 102 to launch an application. The pen 1500 may be provided with several quick launch buttons 1522, which may be user programmable or factory programmable. The quick launch button 1522 may be programmed to perform an operation. For example, one of the buttons may be programmed to clear the digital display of the HWC 102. This would create a fast way for the user to clear the screens on the HWC 102 for any reason, such as for example to better view the environment. The quick launch button functionality will be discussed in further detail below. The touch sensor 1520 may be used to take gesture style input from the user. For example, the user may be able to take a single finger and run it across the touch sensor 1520 to affect a page scroll.

The pen 1500 may also include a laser pointer 1524. The laser pointer 1524 may be coordinated with the IMU 1512 to coordinate gestures and laser pointing. For example, a user may use the laser 1524 in a presentation to help with guiding the audience with the interpretation of graphics and the IMU 1512 may, either simultaneously or when the laser 1524 is off, interpret the user's gestures as commands or data input.

Figure 16A:
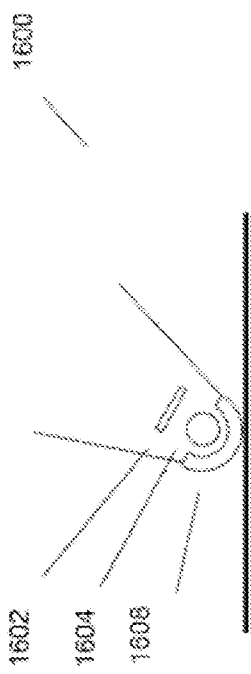
FIGS. 16a to 16c illustrate distance control systems in accordance with the principles of the present invention.
Figure 16B:
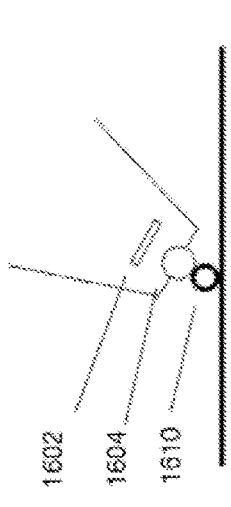
Figure 16C:
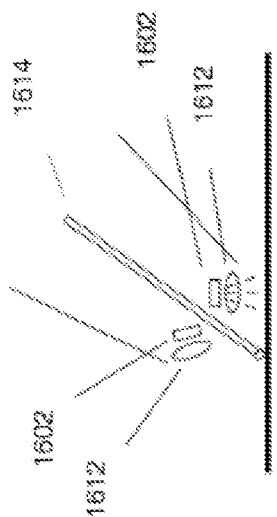

FIGS. 16A-C illustrate several embodiments of lens and camera arrangements 1600 for the pen 1500. One aspect relates to maintaining a constant distance between the camera and the writing surface to enable the writing surface to be kept in focus for better tracking of movements of the pen 1500 over the writing surface. Another aspect relates to maintaining an angled surface following the circumference of the writing tip of the pen 1500 such that the pen 1500 can be rolled or partially rolled in the user's hand to create the feel and freedom of a conventional writing instrument.

FIG. 16A illustrates an embodiment of the writing lens end of the pen 1500. The configuration includes a ball lens 1604, a camera or image capture surface 1602, and a domed cover lens 1608. In this arrangement, the camera views the writing surface through the ball lens 1604 and dome cover lens 1608. The ball lens 1604 causes the camera to focus such that the camera views the writing surface when the pen 1500 is held in the hand in a natural writing position, such as with the pen 1500 in contact with a writing surface. In embodiments, the ball lens 1604 should be separated from the writing surface to obtain the highest resolution of the writing surface at the camera 1602. In embodiments, the ball lens 1604 is separated by approximately 1 to 3 mm. In this configuration, the domed cover lens 1608 provides a surface that can keep the ball lens 1604 separated from the writing surface at a constant distance, such as substantially independent of the angle used to write on the writing surface. For instance, in embodiments the field of view of the camera in this arrangement would be approximately 60 degrees.

The domed cover lens, or other lens 1608 used to physically interact with the writing surface, will be transparent or transmissive within the active bandwidth of the camera 1602. In embodiments, the domed cover lens 1608 may be spherical or other shape and comprised of glass, plastic, sapphire, diamond, and the like. In other embodiments where low resolution imaging of the surface is acceptable. The pen 1500 can omit the domed cover lens 1608 and the ball lens 1604 can be in direct contact with the surface.

FIG. 16B illustrates another structure where the construction is somewhat similar to that described in connection with FIG. 16A; however this embodiment does not use a dome cover lens 1608, but instead uses a spacer 1610 to maintain a predictable distance between the ball lens 1604 and the writing surface, wherein the spacer may be spherical, cylindrical, tubular or other shape that provides spacing while allowing for an image to be obtained by the camera 1602 through the lens 1604. In a preferred embodiment, the spacer 1610 is transparent. In addition, while the spacer 1610 is shown as spherical, other shapes such as an oval, doughnut shape, half sphere, cone, cylinder or other form may be used.

FIG. 16C illustrates yet another embodiment, where the structure includes a post 1614, such as running through the center of the lensed end of the pen 1500. The post 1614 may be an ink deposition system (e.g. ink cartridge), graphite deposition system (e.g. graphite holder), or a dummy post whose purpose is mainly only that of alignment. The selection of the post type is dependent on the pen's use. For instance, in the event the user wants to use the pen 1500 as a conventional ink depositing pen as well as a fully functional external user interface 104, the ink system post would be the best selection. If there is no need for the 'writing' to be visible on the writing surface, the selection would be the dummy post. The embodiment of FIG. 16C includes camera(s) 1602 and an associated lens 1612, where the camera 1602 and lens 1612 are positioned to capture the writing surface without substantial interference from the post 1614. In embodiments, the pen 1500 may include multiple cameras 1602 and lenses 1612 such that more or all of the circumference of the tip 1614 can be used as an input system. In an embodiment, the pen 1500 includes a contoured grip that keeps the pen aligned in the user's hand so that the camera 1602 and lens 1612 remains pointed at the surface.

Another aspect of the pen 1500 relates to sensing the force applied by the user to the writing surface with the pen 1500. The force measurement may be used in a number of ways.

For example, the force measurement may be used as a discrete value, or discontinuous event tracking, and compared against a threshold in a process to determine a user's intent. The user may want the force interpreted as a 'click' in the selection of an object, for instance. The user may intend multiple force exertions interpreted as multiple clicks. There may be times when the user holds the pen 1500 in a certain position or holds a certain portion of the pen 1500 (e.g. a button or touch pad) while clicking to affect a certain operation (e.g. a 'right click'). In embodiments, the force measurement may be used to track force and force trends. The force trends may be tracked and compared to threshold limits, for example. There may be one such threshold limit, multiple limits, groups of related limits, and the like. For example, when the force measurement indicates a fairly constant force that generally falls within a range of related threshold values, the microprocessor 1510 may interpret the force trend as an indication that the user desires to maintain the current writing style, writing tip type, line weight, brush type, and the like. In the event that the force trend appears to have gone outside of a set of threshold values intentionally, the microprocessor may interpret the action as an indication that the user wants to change the current writing style, writing tip type, line weight, brush type, and the like. Once the microprocessor has made a determination of the user's intent, a change in the current writing style, writing tip type, line weight, brush type, and the like may be executed. In embodiments, the change may be noted to the user (e.g. in a display of the HWC 102), and the user may be presented with an opportunity to accept the change.

FIG. 17A illustrates an embodiment of a force sensing surface tip 1700 of a pen 1500. The force sensing surface tip 1700 comprises a surface connection tip 1702 (e.g. a lens as described herein elsewhere) in connection with a force or pressure monitoring system 1504. As a user uses the pen 1500 to write on a surface or simulate writing on a surface the force monitoring system 1504 measures the force or pressure the user applies to the writing surface and the force monitoring system communicates data to the microprocessor 1510 for processing. In this configuration, the microprocessor 1510 receives force data from the force monitoring system 1504 and processes the data to make predictions of the user's intent in applying the particular force that is currently being applied. In embodiments, the processing may be provided at a location other than on the pen (e.g. at a server in the HWC system 100, on the HWC 102). For clarity, when reference is made herein to processing information on the microprocessor 1510, the processing of information contemplates processing the information at a location other than on the pen. The microprocessor 1510 may be programmed with force threshold(s), force signature(s), force signature library and/or other characteristics intended to guide an inference program in determining the user's intentions based on the measured force or pressure. The microprocessor 1510 may be further programmed to make inferences from the force measurements as to whether the user has attempted to initiate a discrete action (e.g. a user interface selection 'click') or is performing a constant action (e.g. writing within a particular writing style). The inferencing process is important as it causes the pen 1500 to act as an intuitive external user interface 104.

FIG. 17B illustrates a force 1708 versus time 1710 trend chart with a single threshold 1718. The threshold 1718 may be set at a level that indicates a discrete force exertion indicative of a user's desire to cause an action (e.g. select an object in a GUI). Event 1712, for example, may be interpreted as a click or selection command because the force quickly increased from below the threshold 1718 to above the threshold 1718. The event 1714 may be interpreted as a double click because the force quickly increased above the threshold 1718, decreased below the threshold 1718 and then essentially repeated quickly. The user may also cause the force to go above the threshold 1718 and hold for a period indicating that the user is intending to select an object in the GUI (e.g. a GUI presented in the display of the HWC 102) and 'hold' for a further operation (e.g. moving the object).

While a threshold value may be used to assist in the interpretation of the user's intention, a signature force event trend may also be used. The threshold and signature may be used in combination or either method may be used alone. For example, a single-click signature may be represented by a certain force trend signature or set of signatures. The single-click signature(s) may require that the trend meet a criteria of a rise time between x any y values, a hold time of between a and b values and a fall time of between c and d values, for example. Signatures may be stored for a variety of functions such as click, double click, right click, hold, move, etc. The microprocessor 1510 may compare the real-time force or pressure tracking against the signatures from a signature library to make a decision and issue a command to the software application executing in the GUI.

FIG. 17C illustrates a force 1708 versus time 1710 trend chart with multiple thresholds 1718. By way of example, the force trend is plotted on the chart with several pen force or pressure events. As noted, there are both presumably intentional events 1720 and presumably non-intentional events 1722. The two thresholds 1718 of FIG. 4C create three zones of force: a lower, middle and higher range. The beginning of the trend indicates that the user is placing a lower zone amount of force. This may mean that the user is writing with a given line weight and does not intend to change the weight, the user is writing. Then the trend shows a significant increase 1720 in force into the middle force range. This force change appears, from the trend to have been sudden and thereafter it is sustained. The microprocessor 1510 may interpret this as an intentional change and as a result change the operation in accordance with preset rules (e.g. change line width, increase line weight, etc.). The trend then continues with a second apparently intentional event 1720 into the higher-force range. During the performance in the higher-force range, the force dips below the upper threshold 1718. This may indicate an unintentional force change and the microprocessor may detect the change in range however not affect a change in the operations being coordinated by the pen 1500. As indicated above, the trend analysis may be done with thresholds and/or signatures.

Generally, in the present disclosure, instrument stroke parameter changes may be referred to as a change in line type, line weight, tip type, brush type, brush width, brush pressure, color, and other forms of writing, coloring, painting, and the like.

Another aspect of the pen 1500 relates to selecting an operating mode for the pen 1500 dependent on contextual information and/or selection interface(s). The pen 1500 may have several operating modes. For instance, the pen 1500 may have a writing mode where the user interface(s) of the pen 1500 (e.g. the writing surface end, quick launch buttons 1522, touch sensor 1520, motion based gesture, and the like) is optimized or selected for tasks associated with writing. As another example, the pen 1500 may have a wand mode where the user interface(s) of the pen is optimized or selected for tasks associated with software or device control (e.g. the HWC 102, external local device, remote device 112, and the like). The pen 1500, by way of another example, may have a presentation mode where the user interface(s) is optimized or selected to assist a user with giving a presentation (e.g. pointing with the laser pointer 1524 while using the button(s) 1522 and/or gestures to control the presentation or applications relating to the presentation). The pen may, for example, have a mode that is optimized or selected for a particular device that a user is attempting to control. The pen 1500 may have a number of other modes and an aspect of the present invention relates to selecting such modes.

FIG. 18A illustrates an automatic user interface(s) mode selection based on contextual information. The microprocessor 1510 may be programmed with IMU thresholds 1814 and 1812. The thresholds 1814 and 1812 may be used as indications of upper and lower bounds of an angle 1804 and 1802 of the pen 1500 for certain expected positions during certain predicted modes. When the microprocessor 1510 determines that the pen 1500 is being held or otherwise positioned within angles 1802 corresponding to writing thresholds 1814, for example, the microprocessor 1510 may then institute a writing mode for the pen's user interfaces. Similarly, if the microprocessor 1510 determines (e.g. through the IMU 1512) that the pen is being held at an angle 1804 that falls between the predetermined wand thresholds 1812, the microprocessor may institute a wand mode for the pen's user interface. Both of these examples may be referred to as context based user interface mode selection as the mode selection is based on contextual information (e.g. position) collected automatically and then used through an automatic evaluation process to automatically select the pen's user interface(s) mode.

As with other examples presented herein, the microprocessor 1510 may monitor the contextual trend (e.g. the angle of the pen over time) in an effort to decide whether to stay in a mode or change modes. For example, through signatures, thresholds, trend analysis, and the like, the microprocessor may determine that a change is an unintentional change and therefore no user interface mode change is desired.

Figure 18B:
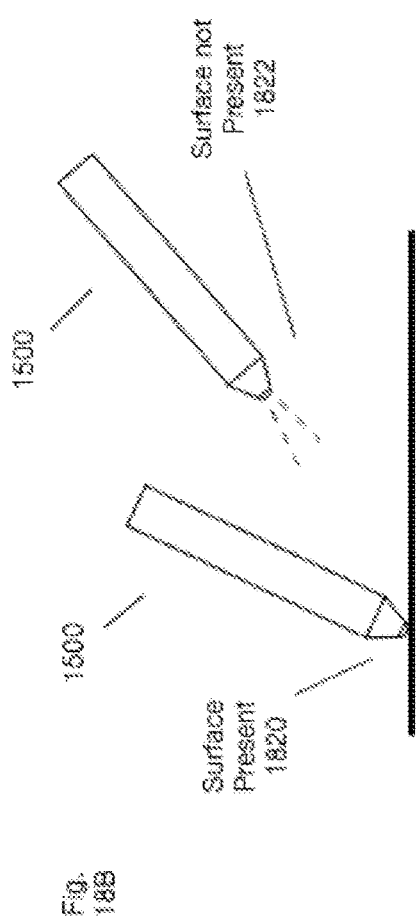

FIG. 18B illustrates an automatic user interface(s) mode selection based on contextual information. In this example, the pen 1500 is monitoring (e.g. through its microprocessor) whether or not the camera at the writing surface end 1508 is imaging a writing surface in close proximity to the writing surface end of the pen 1500. If the pen 1500 determines that a writing surface is within a predetermined relatively short distance, the pen 1500 may decide that a writing surface is present 1820 and the pen may go into a writing mode user interface(s) mode. In the event that the pen 1500 does not detect a relatively close writing surface 1822, the pen may predict that the pen is not currently being used to as a writing instrument and the pen may go into a non-writing user interface(s) mode.

Figure 18C:
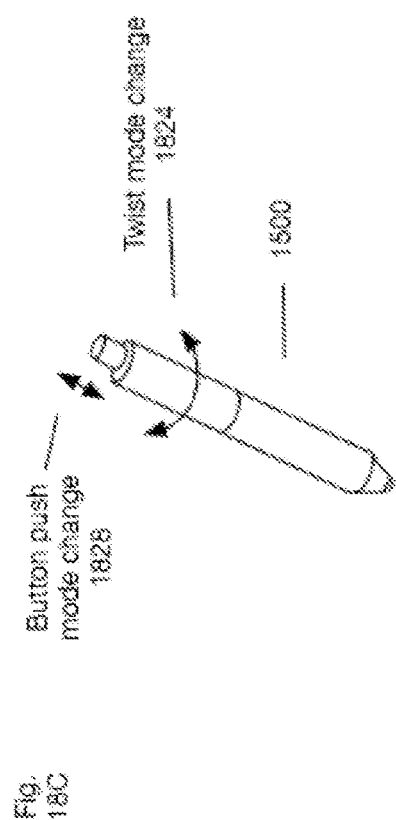

FIG. 18C illustrates a manual user interface(s) mode selection. The user interface(s) mode may be selected based on a twist of a section 1824 of the pen 1500 housing, clicking an end button 1828, pressing a quick launch button 1522, interacting with touch sensor 1520, detecting a predetermined action at the pressure monitoring system (e.g. a click), detecting a gesture (e.g. detected by the IMU), etc. The manual mode selection may involve selecting an item in a GUI associated with the pen 1500 (e.g. an image presented in the display of HWC 102).

In embodiments, a confirmation selection may be presented to the user in the event a mode is going to change. The presentation may be physical (e.g. a vibration in the pen 1500), through a GUI, through a light indicator, etc.

FIG. 19 illustrates a couple pen use-scenarios 1900 and 1901. There are many use scenarios and we have presented a couple in connection with FIG. 19 as a way of illustrating use scenarios to further the understanding of the reader. As such, the use-scenarios should be considered illustrative and non-limiting.

Use scenario 1900 is a writing scenario where the pen 1500 is used as a writing instrument. In this example, quick launch button 122A is pressed to launch a note application 1910 in the GUI 1908 of the HWC 102 display 1904. Once the quick launch button 122A is pressed, the HWC 102 launches the note program 1910 and puts the pen into a writing mode. The user uses the pen 1500 to scribe symbols 1902 on a writing surface, the pen records the scribing and transmits the scribing to the HWC 102 where symbols representing the scribing are displayed 1912 within the note application 1910.

Use scenario 1901 is a gesture scenario where the pen 1500 is used as a gesture capture and command device. In this example, the quick launch button 122B is activated and the pen 1500 activates a wand mode such that an application launched on the HWC 102 can be controlled. Here, the user sees an application chooser 1918 in the display(s) of the HWC 102 where different software applications can be chosen by the user. The user gestures (e.g. swipes, spins, turns, etc.) with the pen to cause the application chooser 1918 to move from application to application. Once the correct application is identified (e.g. highlighted) in the chooser 1918, the user may gesture or click or otherwise interact with the pen 1500 such that the identified application is selected and launched. Once an application is launched, the wand mode may be used to scroll, rotate, change applications, select items, initiate processes, and the like, for example.

In an embodiment, the quick launch button 122A may be activated and the HWC 102 may launch an application chooser presenting to the user a set of applications. For example, the quick launch button may launch a chooser to show all communication programs (e.g. SMS, Twitter, Instagram, Facebook, email, etc.) available for selection such that the user can select the program the user wants and then go into a writing mode. By way of further example, the launcher may bring up selections for various other groups that are related or categorized as generally being selected at a given time (e.g. Microsoft Office products, communication products, productivity products, note products, organizational products, and the like)

Figure 20:
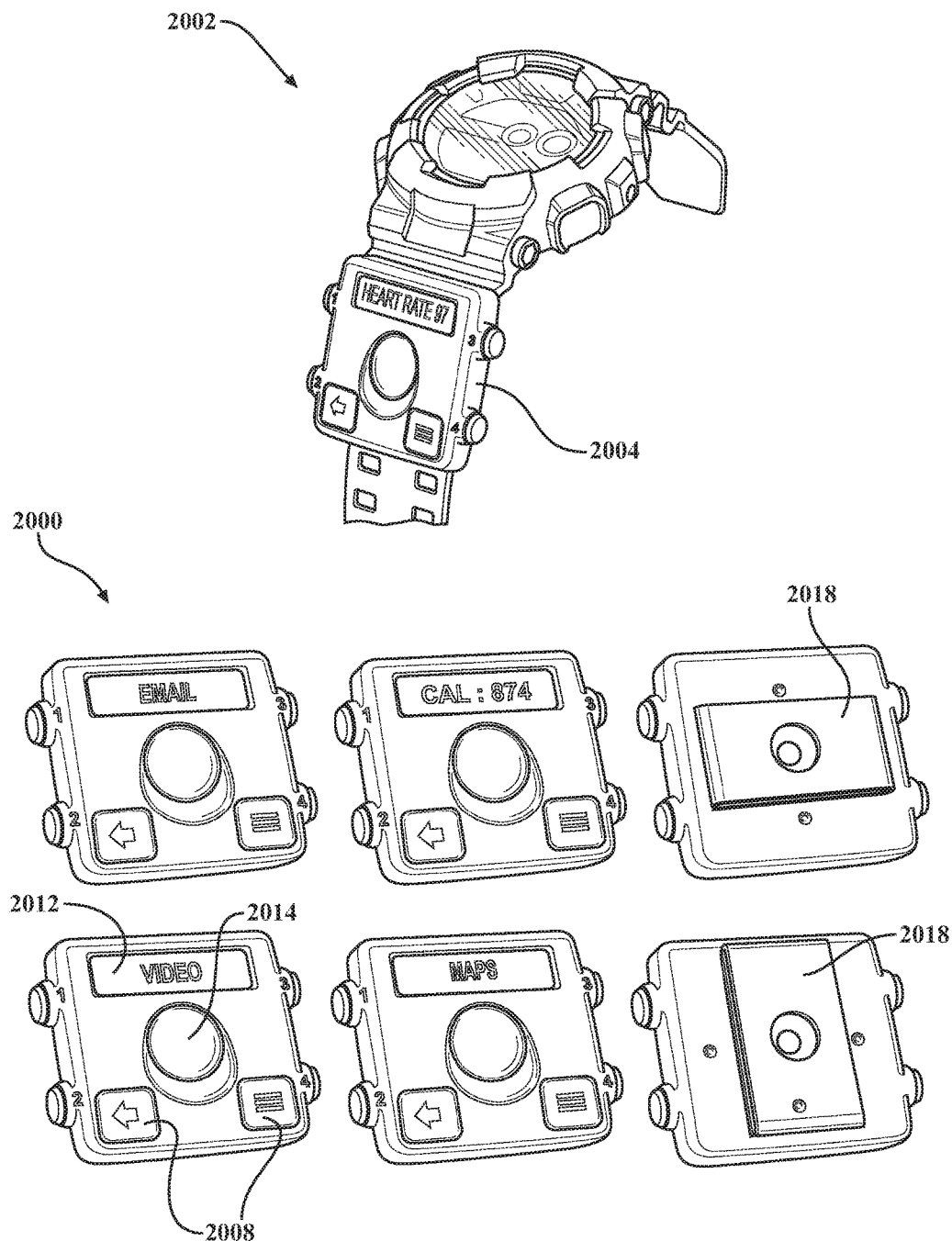
FIG. 20 illustrates external user interfaces in accordance with the principles of the present invention.

FIG. 20 illustrates yet another embodiment of the present invention. FIG. 2000 illustrates a watchband clip on controller 2000. The watchband clip on controller may be a controller used to control the HWC 102 or devices in the HWC system 100. The watchband clip on controller 2000 has a fastener 2018 (e.g. rotatable clip) that is mechanically adapted to attach to a watchband, as illustrated at 2004.

The watchband controller 2000 may have quick launch interfaces 2008 (e.g. to launch applications and choosers as described herein), a touch pad 2014 (e.g. to be used as a touch style mouse for GUI control in a HWC 102 display) and a display 2012. The clip 2018 may be adapted to fit a wide range of watchbands so it can be used in connection with a watch that is independently selected for its function. The clip, in embodiments, is rotatable such that a user can position it in a desirable manner. In embodiments the clip may be a flexible strap. In embodiments, the flexible strap may be adapted to be stretched to attach to a hand, wrist, finger, device, weapon, and the like.

In embodiments, the watchband controller may be configured as a removable and replaceable watchband. For example, the controller may be incorporated into a band with a certain width, segment spacing's, etc. such that the watchband, with its incorporated controller, can be attached to a watch body. The attachment, in embodiments, may be mechanically adapted to attach with a pin upon which the watchband rotates. In embodiments, the watchband controller may be electrically connected to the watch and/or watch body such that the watch, watch body and/or the watchband controller can communicate data between them.

The watchband controller may have 3-axis motion monitoring (e.g. through an IMU, accelerometers, magnetometers, gyroscopes, etc.) to capture user motion. The user motion may then be interpreted for gesture control.

In embodiments, the watchband controller may comprise fitness sensors and a fitness computer. The sensors may track heart rate, calories burned, strides, distance covered, and the like. The data may then be compared against performance goals and/or standards for user feedback.

Another aspect of the present invention relates to visual display techniques relating to micro Doppler ("mD") target tracking signatures ("mD signatures"). mD is a radar technique that uses a series of angle dependent electromagnetic pulses that are broadcast into an environment and return pulses are captured. Changes between the broadcast pulse and return pulse are indicative of changes in the shape, distance and angular location of objects or targets in the environment. These changes provide signals that can be used to track a target and identify the target through the mD signature. Each target or target type has a unique mD signature. Shifts in the radar pattern can be analyzed in the time domain and frequency domain based on mD techniques to derive information about the types of targets present (e.g. whether people are present), the motion of the targets and the relative angular location of the targets and the distance to the targets. By selecting a frequency used for the mD pulse relative to known objects in the environment, the pulse can penetrate the known objects to enable information about targets to be gathered even when the targets are visually blocked by the known objects. For example, pulse frequencies can be used that will penetrate concrete buildings to enable people to be identified inside the building. Multiple pulse frequencies can be used as well in the mD radar to enable different types of information to be gathered about the objects in the environment. In addition, the mD radar information can be combined with other information such as distance measurements or images captured of the environment that are analyzed jointly to provide improved object identification and improved target identification and tracking. In embodiments, the analysis can be performed on the HWC or the information can be transmitted to a remote network for analysis and results transmitted back to the HWC. Distance measurements can be provided by laser range finding, structured lighting, stereoscopic depth maps or sonar measurements. Images of the environment can be captured using one or more cameras capable of capturing images from visible, ultraviolet or infrared light. The mD radar can be attached to the HWC, located adjacently (e.g. in a vehicle) and associated wirelessly with the HWC or located remotely. Maps or other previously determined information about the environment can also be used in the analysis of the mD radar information. Embodiments of the present invention relate to visualizing the mD signatures in useful ways.

Figure 21:
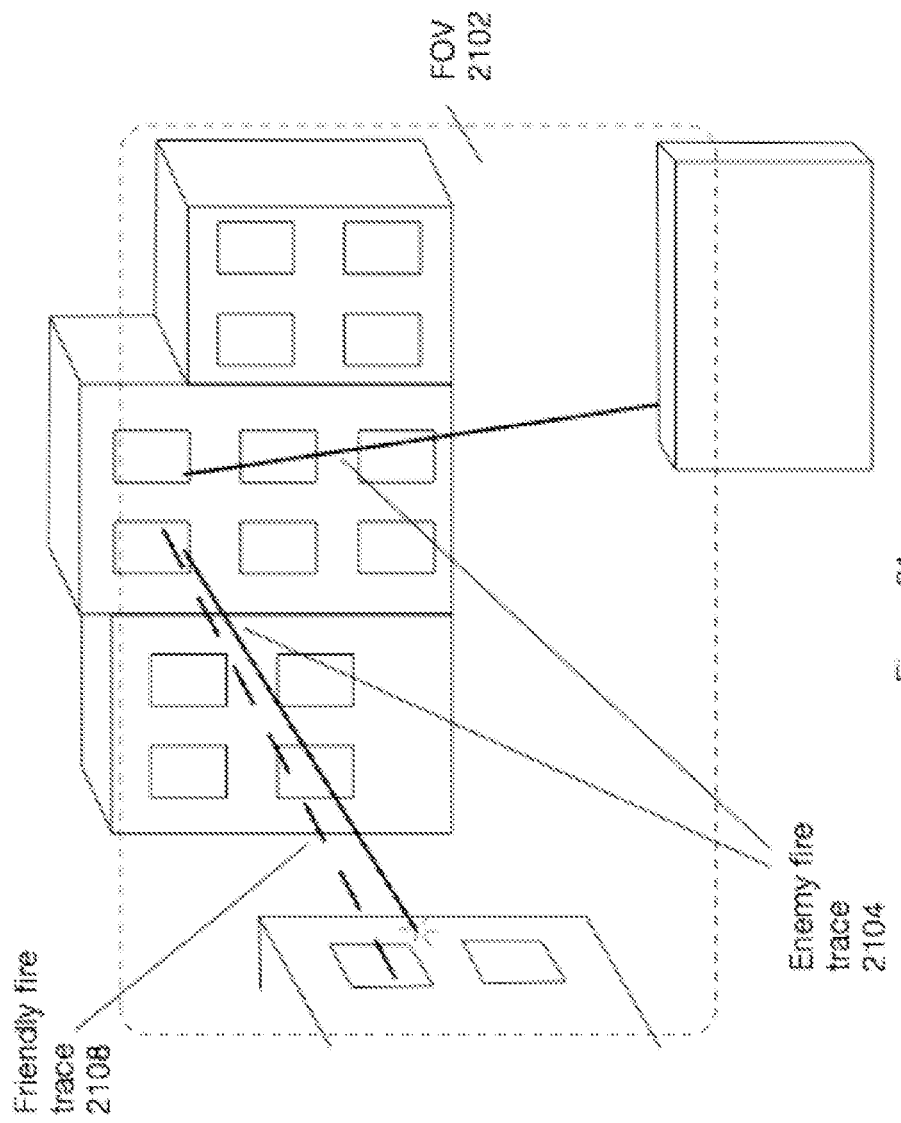
FIG. 21 illustrates mD trace representations presented in accordance with the principles of the present invention.

FIG. 21 illustrates a FOV 2102 of a HWC 102 from a wearer's perspective. The wearer, as described herein elsewhere, has a see-through FOV 2102 wherein the wearer views adjacent surroundings, such as the buildings illustrated in FIG. 21. The wearer, as described herein elsewhere, can also see displayed digital content presented within a portion of the FOV 2102. The embodiment illustrated in FIG. 21 is indicating that the wearer can see the buildings and other surrounding elements in the environment and digital content representing traces, or travel paths, of bullets being fired by different people in the area. The surroundings are viewed through the transparency of the FOV 2102. The traces are presented via the digital computer display, as described herein elsewhere. In embodiments, the trace presented is based on a mD signature that is collected and communicated to the HWC in real time. The mD radar itself may be on or near the wearer of the HWC 102 or it may be located remote from the wearer. In embodiments, the mD radar scans the area, tracks and identifies targets, such as bullets, and communicates traces, based on locations, to the HWC 102.

There are several traces 2108 and 2104 presented to the wearer in the embodiment illustrated in FIG. 21. The traces communicated from the mD radar may be associated with GPS locations and the GPS locations may be associated with objects in the environment, such as people, buildings, vehicles, etc, both in latitude and longitude perspective and an elevation perspective. The locations may be used as markers for the HWC such that the traces, as presented in the FOV, can be associated, or fixed in space relative to the markers. For example, if the friendly fire trace 2108 is determined, by the mD radar, to have originated from the upper right window of the building on the left, as illustrated in FIG. 21, then a virtual marker may be set on or near the window. When the HWC views, through it's camera or other sensor, for example, the building's window, the trace may then virtually anchor with the virtual marker on the window. Similarly, a marker may be set near the termination position or other flight position of the friendly fire trace 2108, such as the upper left window of the center building on the right, as illustrated in FIG. 21. This technique fixes in space the trace such that the trace appears fixed to the environmental positions independent of where the wearer is looking. So, for example, as the wearer's head turns, the trace appears fixed to the marked locations.

In embodiments, certain user positions may be known and thus identified in the FOV. For example, the shooter of the friendly fire trace 2108 may be from a known friendly combatant and as such his location may be known. The position may be known based on his GPS location based on a mobile communication system on him, such as another HWC 102. In other embodiments, the friendly combatant may be marked by another friendly. For example, if the friendly position in the environment is known through visual contact or communicated information, a wearer of the HWC 102 may use a gesture or external user interface 104 to mark the location. If a friendly combatant location is known the originating position of the friendly fire trace 2108 may be color coded or otherwise distinguished from unidentified traces on the displayed digital content. Similarly, enemy fire traces 2104 may be color coded or otherwise distinguished on the displayed digital content. In embodiments, there may be an additional distinguished appearance on the displayed digital content for unknown traces.

In addition to situationally associated trace appearance, the trace colors or appearance may be different from the originating position to the terminating position. This path appearance change may be based on the mD signature. The mD signature may indicate that the bullet, for example, is slowing as it propagates and this slowing pattern may be reflected in the FOV 2102 as a color or pattern change. This can create an intuitive understanding of wear the shooter is located. For example, the originating color may be red, indicative of high speed, and it may change over the course of the trace to yellow, indicative of a slowing trace. This pattern changing may also be different for a friendly, enemy and unknown combatant. The enemy may go blue to green for a friendly trace, for example.

FIG. 21 illustrates an embodiment where the user sees the environment through the FOV and may also see color coded traces, which are dependent on bullet speed and combatant type, where the traces are fixed in environmental positions independent on the wearer's perspective. Other information, such as distance, range, range rings, time of day, date, engagement type (e.g. hold, stop firing, back away, etc.) may also be displayed in the FOV.

Figure 22:
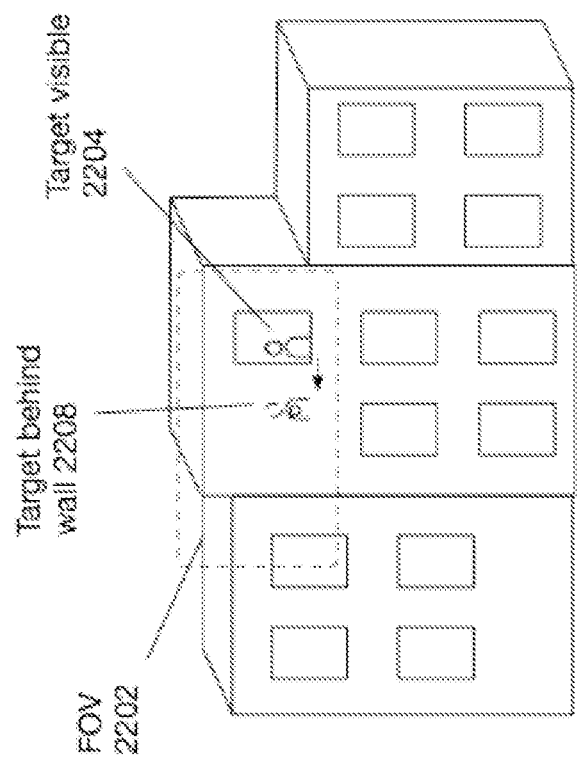
FIG. 22 illustrates mD trace representations presented in accordance with the principles of the present invention.

Another aspect of the present invention relates to mD radar techniques that trace and identify targets through other objects, such as walls (referred to generally as through wall mD), and visualization techniques related therewith. FIG. 22 illustrates a through wall mD visualization technique according to the principles of the present invention. As described herein elsewhere, the mD radar scanning the environment may be local or remote from the wearer of a HWC 102. The mD radar may identify a target (e.g. a person) that is visible 2204 and then track the target as he goes behind a wall 2208. The tracking may then be presented to the wearer of a HWC 102 such that digital content reflective of the target and the target's movement, even behind the wall, is presented in the FOV 2202 of the HWC 102. In embodiments, the target, when out of visible sight, may be represented by an avatar in the FOV to provide the wearer with imagery representing the target.

mD target recognition methods can identify the identity of a target based on the vibrations and other small movements of the target. This can provide a personal signature for the target. In the case of humans, this may result in a personal identification of a target that has been previously characterized. The cardio, heart beat, lung expansion and other small movements within the body may be unique to a person and if those attributes are pre-identified they may be matched in real time to provide a personal identification of a person in the FOV 2202. The person's mD signatures may be determined based on the position of the person. For example, the database of personal mD signature attributes may include mD signatures for a person standing, sitting, laying down, running, walking, jumping, etc. This may improve the accuracy of the personal data match when a target is tracked through mD signature techniques in the field. In the event a person is personally identified, a specific indication of the person's identity may be presented in the FOV 2202. The indication may be a color, shape, shade, name, indication of the type of person (e.g. enemy, friendly, etc.), etc. to provide the wearer with intuitive real time information about the person being tracked. This may be very useful in a situation where there is more than one person in an area of the person being tracked. If just one person in the area is personally identified, that person or the avatar of that person can be presented differently than other people in the area.

Figure 23:
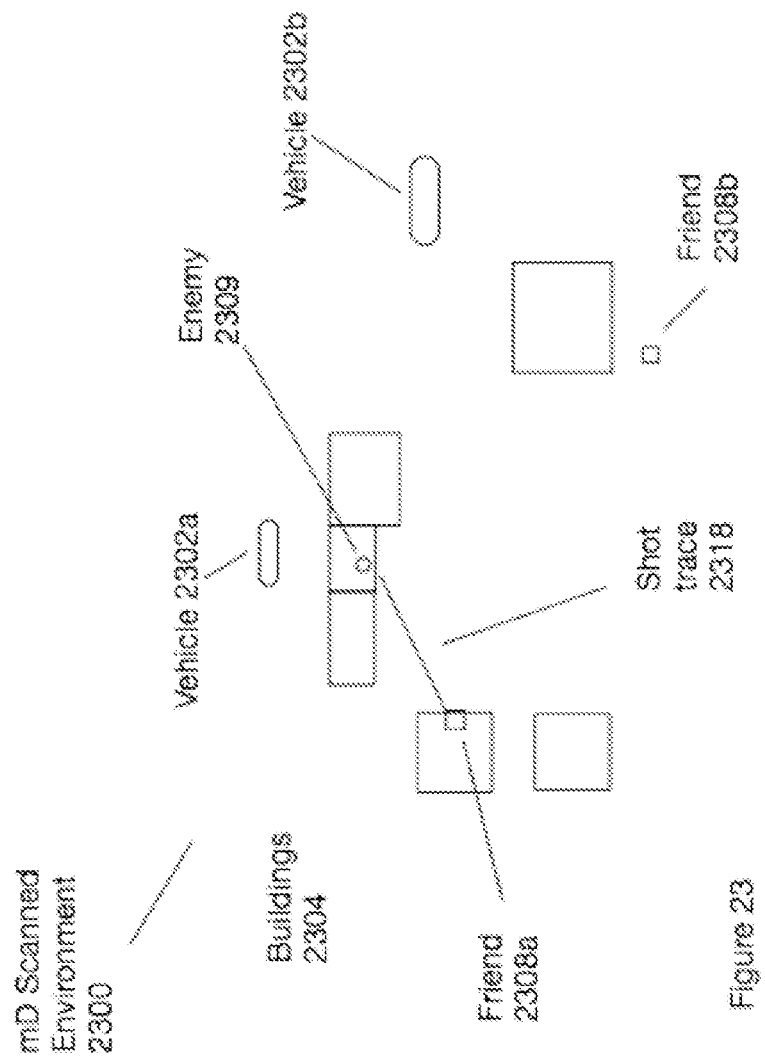
FIG. 23 illustrates an mD scanned environment in accordance with the principles of the present invention.

FIG. 23 illustrates an mD scanned environment 2300. An mD radar may scan an environment in an attempt to identify objects in the environment. In this embodiment, the mD scanned environment reveals two vehicles 2302a and 2302b, en enemy combatant 2309, two friendly combatants 2308a and 2308b and a shot trace 2318. Each of these objects may be personally identified or type identified. For example, the vehicles 2302a and 2302b may be identified through the mD signatures as a tank and heavy truck. The enemy combatant 2309 may be identified as a type (e.g. enemy combatant) or more personally (e.g. by name). The friendly combatants may be identified as a type (e.g. friendly combatant) or more personally (e.g. by name). The shot trace 2318 may be characterized by type of projectile or weapon type for the projectile, for example.

Figure 23A:
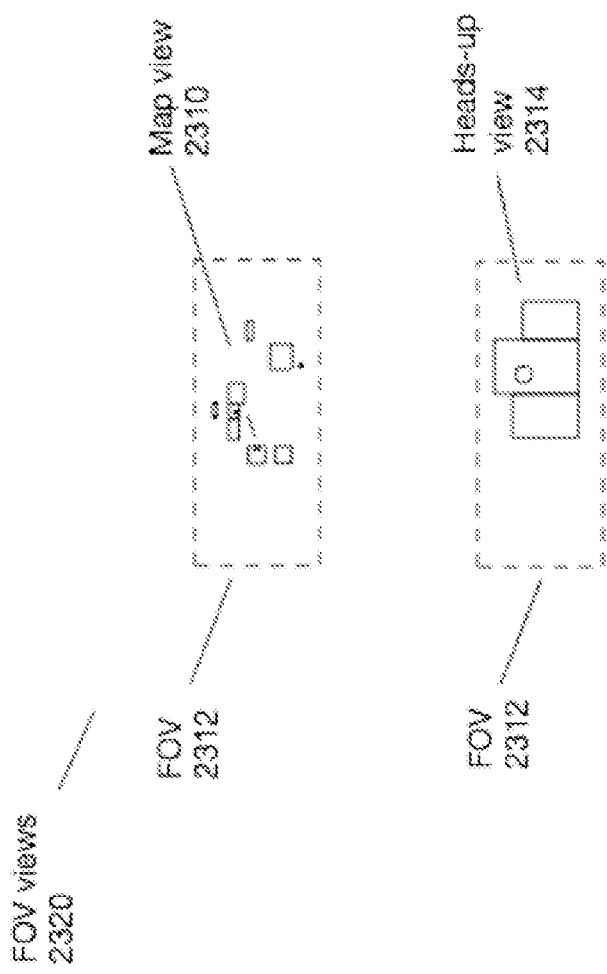
FIG. 23a illustrates mD trace representations presented in accordance with the principles of the present invention.

FIG. 23a illustrates two separate HWC 102 FOV display techniques according to the principles of the present invention. FOV 2312 illustrates a map view 2310 where the mD scanned environment is presented. Here, the wearer has a perspective on the mapped area so he can understand all tracked targets in the area. This allows the wearer to traverse the area with knowledge of the targets. FOV 2312 illustrates a heads-up view to provide the wearer with an augmented reality style view of the environment that is in proximity of the wearer.

An aspect of the present invention relates to suppression of extraneous or stray light. As discussed herein elsewhere, eyeglow and faceglow are two such artifacts that develop from such light. Eyeglow and faceglow can be caused by image light escaping from the optics module. The escaping light is then visible, particularly in dark environments when the user is viewing bright displayed images with the HWC. Light that escapes through the front of the HWC is visible as eyeglow as it that light that is visible in the region of the user's eyes. Eyeglow can appear in the form of a small version of the displayed image that the user is viewing. Light that escapes from the bottom of the HWC shines onto the user's face, cheek or chest so that these portions of the user appear to glow. Eyeglow and faceglow can both increase the visibility of the user and highlight the use of the HWC, which may be viewed negatively by the user. As such, reducing eyeglow and faceglow is advantageous. In combat situations (e.g. the mD trace presentation scenarios described herein) and certain gaming situations, the suppression of extraneous or stray light is very important.

The disclosure relating to FIG. 6 shows an example where a portion of the image light passes through the combiner 602 such that the light shines onto the user's face, thereby illuminating a portion of the user's face in what is generally referred to herein as faceglow. Faceglow be caused by any portion of light from the HWC that illuminates the user's face.

An example of the source for the faceglow light can come from wide cone angle light associated with the image light incident onto the combiner 602. Where the combiner can include a holographic mirror or a notch mirror in which the narrow bands of high reflectivity are matched to wavelengths of light by the light source. The wide cone angle associated with the image light corresponds with the field of view provided by the HWC. Typically the reflectivity of holographic mirrors and notch mirrors is reduced as the cone angle of the incident light is increased above 8 degrees. As a result, for a field of view of 30 degrees, substantial image light can pass through the combiner and cause faceglow.

Figure 24:
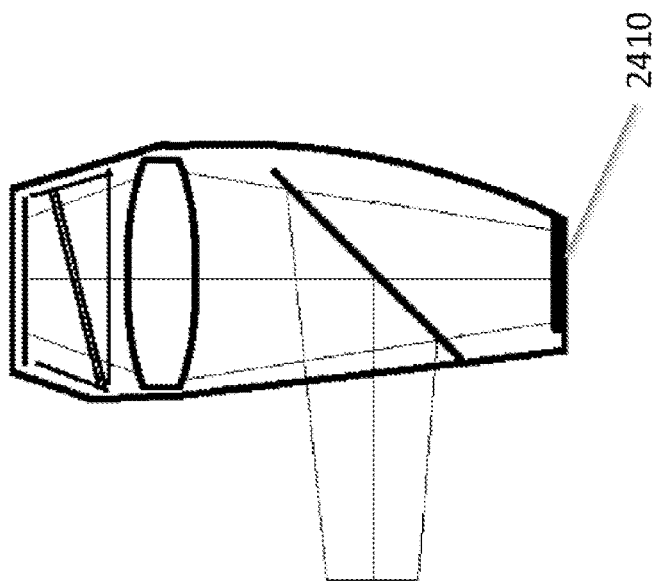
FIG. 24 illustrates a stray light suppression technology in accordance with the principles of the present invention.

FIG. 24 shows an illustration of a light trap 2410 for the faceglow light. In this embodiment, an extension of the outer shield len of the HWC is coated with a light absorbing material in the region where the converging light responsible for faceglow is absorbed in a light trap 2410. The light absorbing material can be black or it can be a filter designed to absorb only the specific wavelengths of light provided by the light source(s) in the HWC. In addition, the surface of the light trap 2410 may be textured or fibrous to further improve the absorption.

Figure 25:
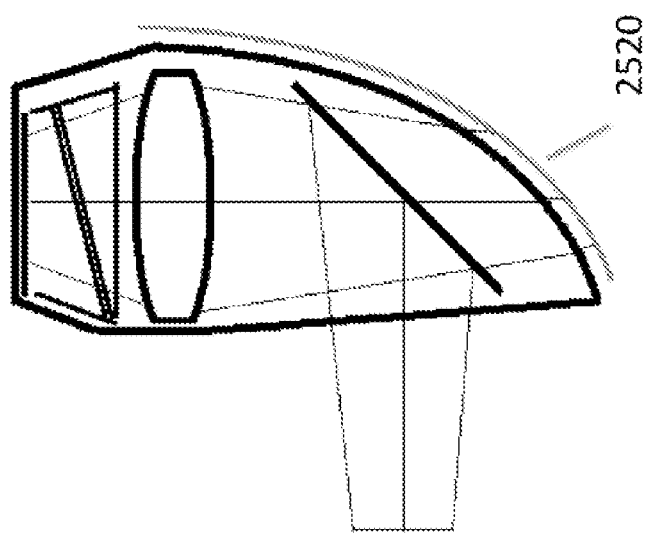
FIG. 25 illustrates a stray light suppression technology in accordance with the principles of the present invention.

FIG. 25 illustrates an optical system for a HWC that includes an outer absorptive polarizer 2520 to block the faceglow light. In this embodiment, the image light is polarized and as a result the light responsible for faceglow is similarly polarized. The absorptive polarizer is oriented with a transmission axis such that the faceglow light is absorbed and not transmitted. In this case, the rest of the imaging system in the HWC may not require polarized image light and the image light may be polarized at any point before the combiner. In embodiments, the transmission axis of the absorptive polarizer 2520 is oriented vertically so that external glare from water (S polarized light) is absorbed and correspondingly, the polarization of the image light is selected to be horizontal (S polarization). Consequently, image light that passes through the combiner 602 and is then incident onto the absorptive polarizer 2520, is absorbed. In FIG. 25 the absorptive polarizer 2520 is shown outside the shield lens, alternatively the absorptive polarizer 2520 can be located inside the shield lens.

Figure 26:
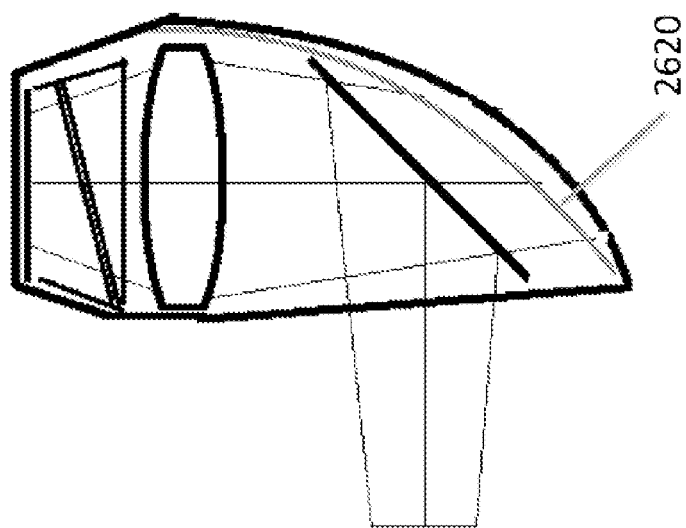
FIG. 26 illustrates a stray light suppression technology in accordance with the principles of the present invention.

FIG. 26 illustrates an optical system for a HWC that includes a film with an absorptive notch filter 2620. In this case, the absorptive notch filter absorbs narrow bands of light that are selected to match the light provided by the optical system's light source. As a result, the absorptive notch filter is opaque with respect to the faceglow light and is transparent to the remainder of the wavelengths included in the visible spectrum so that the user has a clear view of the surrounding environment. A triple notch filter suitable for this approach is available from Iridian Spectral Technologies, Ottawa, ON: http://www.ilphotonics.com/cdv2/Iridian-Interference %20Filters/New%20filters/Triple%20Notch%20Filter.pdf In embodiments, the combiner 602 may include a notch mirror coating to reflect the wavelengths of light in the image light and a notch filter 2620 can be selected in correspondence to the wavelengths of light provided by the light source and the narrow bands of high reflectivity provided by the notch mirror. In this way, image light that is not reflected by the notch mirror is absorbed by the notch filter 2620. In embodiments of the invention the light source can provide one narrow band of light for a monochrome imaging or three narrow bands of light for full color imaging. The notch mirror and associated notch filter would then each provide one narrow band or three narrow bands of high reflectivity and absorption respectively.

Figure 27:
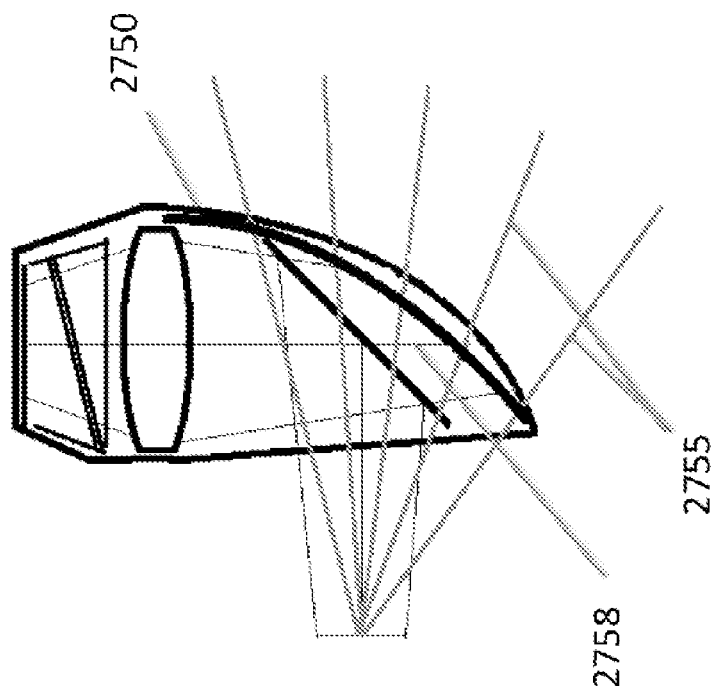
FIG. 27 illustrates a stray light suppression technology in accordance with the principles of the present invention.

FIG. 27 includes a microlouver film 2750 to block the faceglow light. Microlouver film is sold by 3M as ALCF-P, for example and is typically used as a privacy filter for computer. See http://multimedia.3 m.com/mws/mediawebserver?mwsId=SSSSSuH8gc7nZxtUoY_x lY_eevUqe17zHvTSevTSeSSSSSS--&fn=ALCF-P_ABR2_Control_Film_DS.pdf The microlouver film transmits light within a somewhat narrow angle (e.g. 30 degrees of normal and absorbs light beyond 30 degrees of normal). In FIG. 27, the microlouver film 2750 is positioned such that the faceglow light 2758 is incident beyond 30 degrees from normal while the see-through light 2755 is incident within 30 degrees of normal to the microlouver film 2750. As such, the faceglow light 2758 is absorbed by the microlouver film and the see-through light 2755 is transmitted so that the user has a bright see-thru view of the surrounding environment.

We now turn back to a description of eye imaging technologies. Aspects of the present invention relate to various methods of imaging the eye of a person wearing the HWC 102. In embodiments, technologies for imaging the eye using an optical path involving the "off" state and "no power" state, which is described in detail below, are described. In embodiments, technologies for imaging the eye with optical configurations that do not involve reflecting the eye image off of DLP mirrors is described. In embodiments, unstructured light, structured light, or controlled lighting conditions, are used to predict the eye's position based on the light reflected off of the front of the wearer's eye. In embodiments, a reflection of a presented digital content image is captured as it reflects off of the wearer's eye and the reflected image may be processed to determine the quality (e.g. sharpness) of the image presented. In embodiments, the image may then be adjusted (e.g. focused differently) to increase the quality of the image presented based on the image reflection.

FIGS. 28*a*, 28*b* and 28*c* show illustrations of the various positions of the DLP mirrors. FIG. 28*a* shows the DLP mirrors in the "on" state 2815. With the mirror in the "on" state 2815, illumination light 2810 is reflected along an optical axis 2820 that extends into the lower optical module 204. FIG. 28*b* shows the DLP mirrors in the "off" state 2825. With the mirror in the "off" state 2825, illumination light 2810 is reflected along an optical axis 2830 that is substantially to the side of optical axis 2820 so that the "off" state light is directed toward a dark light trap as has been described herein elsewhere. FIG. 28*c* shows the DLP mirrors in a third position, which occurs when no power is applied to the DLP. This "no power" state differs from the "on" and "off" states in that the mirror edges are not in contact with the substrate and as such are less accurately positioned. FIG. 28*c* shows all of the DLP mirrors in the "no power" state 2835. The "no power" state is achieved by simultaneously setting the voltage to zero for the "on" contact and "off" contact for a DLP mirror, as a result, the mirror returns to a no stress position where the DLP mirror is in the plane of the DLP platform as shown in FIG. 28*c*. Although not normally done, it is also possible to apply the "no power" state to individual DLP mirrors. When the DLP mirrors are in the "no power" state they do not contribute image content. Instead, as shown in FIG. 28*c*, when the DLP mirrors are in the "no power" state, the illumination light 2810 is reflected along an optical axis 2840 that is between the optical axes 2820 and 2830 that are respectively associated with the "on" and "off" states and as such this light doesn't contribute to the displayed image as a bright or dark pixel. This light can however contribute scattered light into the lower optical module 204 and as a result the displayed image contrast can be reduced or artifacts can be created in the image that detract from the image content. Consequently, it is generally desirable, in embodiments, to limit the time associated with the "no power" state to times when images are not displayed or to reduce the time associated with having DLP mirrors in the "no power" state so that the affect of the scattered light is reduced.

FIG. 29 shows an embodiment of the invention that can be used for displaying digital content images to a wearer of the HWC 102 and capturing images of the wearer's eye. In this embodiment, light from the eye 2971 passes back through the optics in the lower module 204, the solid corrective wedge 2966, at least a portion of the light passes through the partially reflective layer 2960, the solid illumination wedge 2964 and is reflected by a plurality of DLP mirrors on the DLP 2955 that are in the "no power" state. The reflected light then passes back through the illumination wedge 2964 and at least a portion of the light is reflected by the partially reflective layer 2960 and the light is captured by the camera 2980.

For comparison, illuminating light rays 2973 from the light source 2958 are also shown being reflected by the partially reflective layer 2960. Where the angle of the illuminating light 2973 is such that the DLP mirrors, when in the "on" state, reflect the illuminating light 2973 to form image light 2969 that substantially shares the same optical axis as the light from the wearer's eye 2971. In this way, images of the wearer's eye are captured in a field of view that overlaps the field of view for the displayed image content. In contrast, light reflected by DLP mirrors in the "off" state form dark light 2975 which is directed substantially to the side of the image light 2969 and the light from eye 2971. Dark light 2975 is directed toward a light trap 2962 that absorbs the dark light to improve the contrast of the displayed image as has been described above in this specification.

In an embodiment, partially reflective layer 2960 is a reflective polarizer. The light that is reflected from the eye 2971 can then be polarized prior to entering the corrective wedge 2966 (e.g with an absorptive polarizer between the upper module 202 and the lower module 204), with a polarization orientation relative to the reflective polarizer that enables the light reflected from the eye 2971 to substantially be transmitted by the reflective polarizer. A quarter wave retarder layer 2957 is then included adjacent to the DLP 2955 (as previously disclosed in FIG. 3*b*) so that the light reflected from the eye 2971 passes through the quarter wave retarder layer 2957 once before being reflected by the plurality of DLP mirrors in the "no power" state and then passes through a second time after being reflected. By passing through the quarter wave retarder layer 2957 twice, the polarization state of the light from the eye 2971 is reversed, such that when it is incident upon the reflective polarizer, the light from the eye 2971 is then substantially reflected toward the camera 2980. By using a partially reflective layer 2960 that is a reflective polarizer and polarizing the light from the eye 2971 prior to entering the corrective wedge 2964, losses attributed to the partially reflective layer 2960 are reduced.

FIG. 28*c* shows the case wherein the DLP mirrors are simultaneously in the "no power" state, this mode of operation can be particularly useful when the HWC 102 is first put onto the head of the wearer. When the HWC 102 is first put onto the head of the wearer, it is not necessary to display an image yet. As a result, the DLP can be in a "no power" state for all the DLP mirrors and an image of the wearer's eyes can be captured. The captured image of the wearer's eye can then be compared to a database, using iris identification techniques, or other eye pattern identification techniques to determine, for example, the identity of the wearer.

In a further embodiment illustrated by FIG. 29 all of the DLP mirrors are put into the "no power" state for a portion of a frame time (e.g. 50% of a frame time for the displayed digital content image) and the capture of the eye image is synchronized to occur at the same time and for the same duration. By reducing the time that the DLP mirrors are in the "no power" state, the time where light is scattered by the DLP mirrors being in the "no power" state is reduced such that the wearer doesn't perceive a change in the displayed image quality. This is possible because the DLP mirrors have a response time on the order of microseconds while typical frame times for a displayed image are on the order of 0.016 seconds. This method of capturing images of the wearer's eye can be used periodically to capture repetitive images of the wearer's eye. For example, eye images could be captured for 50% of the frame time of every 10th frame displayed to the wearer. In another example, eye images could be captured for 10% of the frame time of every frame displayed to the wearer.

Alternately, the "no power" state can be applied to a subset of the DLP mirrors (e.g. 10% of the DLP mirrors) within while another subset is in busy generating image light for content to be displayed. This enables the capture of an eye image(s) during the display of digital content to the wearer. The DLP mirrors used for eye imaging can, for example, be distributed randomly across the area of the DLP to minimize the impact on the quality of the digital content being displayed to the wearer. To improve the displayed image perceived by the wearer, the individual DLP mirrors put into the "no power" state for capturing each eye image, can be varied over time such as in a random pattern, for example. In yet a further embodiment, the DLP mirrors put into the "no power" state for eye imaging may be coordinated with the digital content in such a way that the "no power" mirrors are taken from a portion of the image that requires less resolution.

In the embodiments of the invention as illustrated in FIGS. 9 and 29, in both cases the reflective surfaces provided by the DLP mirrors do not preserve the wavefront of the light from the wearer's eye so that the image quality of captured image of the eye is somewhat limited. It may still be useful in certain embodiments, but it is somewhat limited. This is due to the DLP mirrors not being constrained to be on the same plane. In the embodiment illustrated in FIG. 9, the DLP mirrors are tilted so that they form rows of DLP mirrors that share common planes. In the embodiment illustrated in FIG. 29, the individual DLP mirrors are not accurately positioned to be in the same plane since they are not in contact with the substrate. Examples of advantages of the embodiments associated with FIG. 29 are: first, the camera 2980 can be located between the DLP 2955 and the illumination light source 2958 to provide a more compact upper module 202. Second, the polarization state of the light reflected from the eye 2971 can be the same as that of the image light 2969 so that the optical path of the light reflected from the eye and the image light can be the same in the lower module 204.

Figure 30:
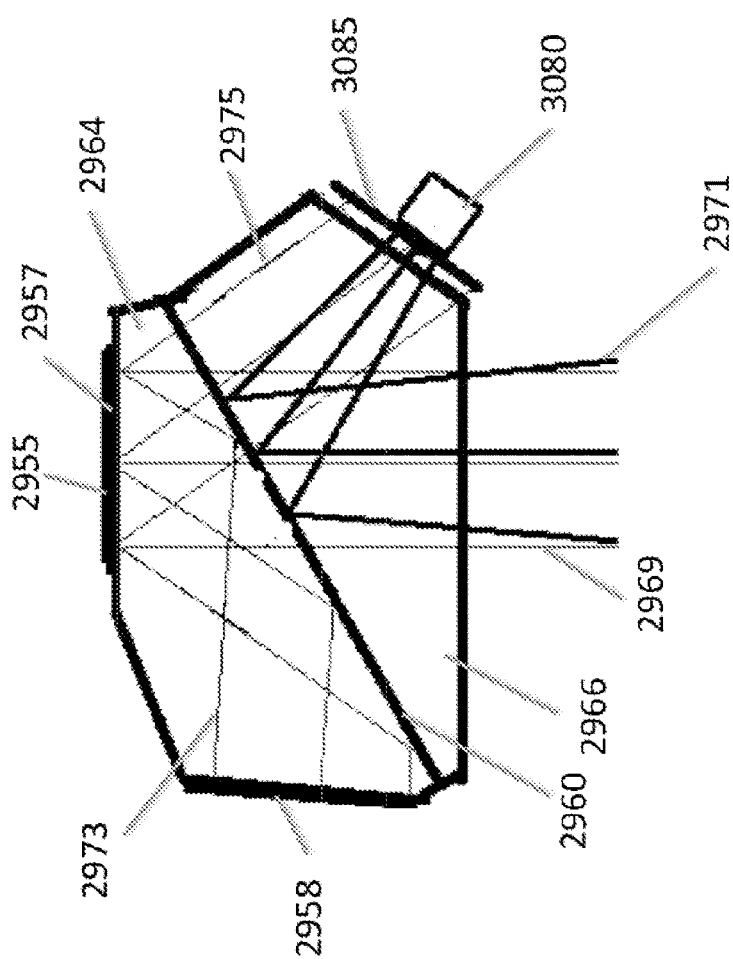

FIG. 30 shows an illustration of an embodiment for displaying images to the wearer and simultaneously capturing images of the wearer's eye, wherein light from the eye 2971 is reflected towards a camera 3080 by the partially reflective layer 2960. The partially reflective layer 2960 can be an optically flat layer such that the wavefront of the light from the eye 2971 is preserved and as a result, higher quality images of the wearer's eye can be captured. In addition, since the DLP 2955 is not included in the optical path for the light from the eye 2971, and the eye imaging process shown in FIG. 30 does not interfere with the displayed image, images of the wearer's eye can be captured independently (e.g. with independent of timing, impact on resolution, or pixel count used in the image light) from the displayed images.

In the embodiment illustrated in FIG. 30, the partially reflective layer 2960 is a reflective polarizer, the illuminating light 2973 is polarized, the light from the eye 2971 is polarized and the camera 3080 is located behind a polarizer 3085. The polarization axis of the illuminating light 2973 and the polarization axis of the light from the eye are oriented perpendicular to the transmission axis of the reflective polarizer so that they are both substantially reflected by the reflective polarizer. The illumination light 2973 passes through a quarter wave layer 2957 before being reflected by the DLP mirrors in the DLP 2955. The reflected light passes back through the quarter wave layer 2957 so that the polarization states of the image light 2969 and dark light 2975 are reversed in comparison to the illumination light 2973. As such, the image light 2969 and dark light 2975 are substantially transmitted by the reflective polarizer. Where the DLP mirrors in the "on" state provide the image light 2969 along an optical axis that extends into the lower optical module 204 to display an image to the wearer. At the same time, DLP mirrors in the "off" state provide the dark light 2975 along an optical axis that extends to the side of the upper optics module 202. In the region of the corrective wedge 2966 where the dark light 2975 is incident on the side of the upper optics module 202, an absorptive polarizer 3085 is positioned with it's transmission axis perpendicular to the polarization axis of the dark light and parallel to the polarization axis of the light from the eye so that the dark light 2975 is absorbed and the light from the eye 2971 is transmitted to the camera 3080.

Figure 31:
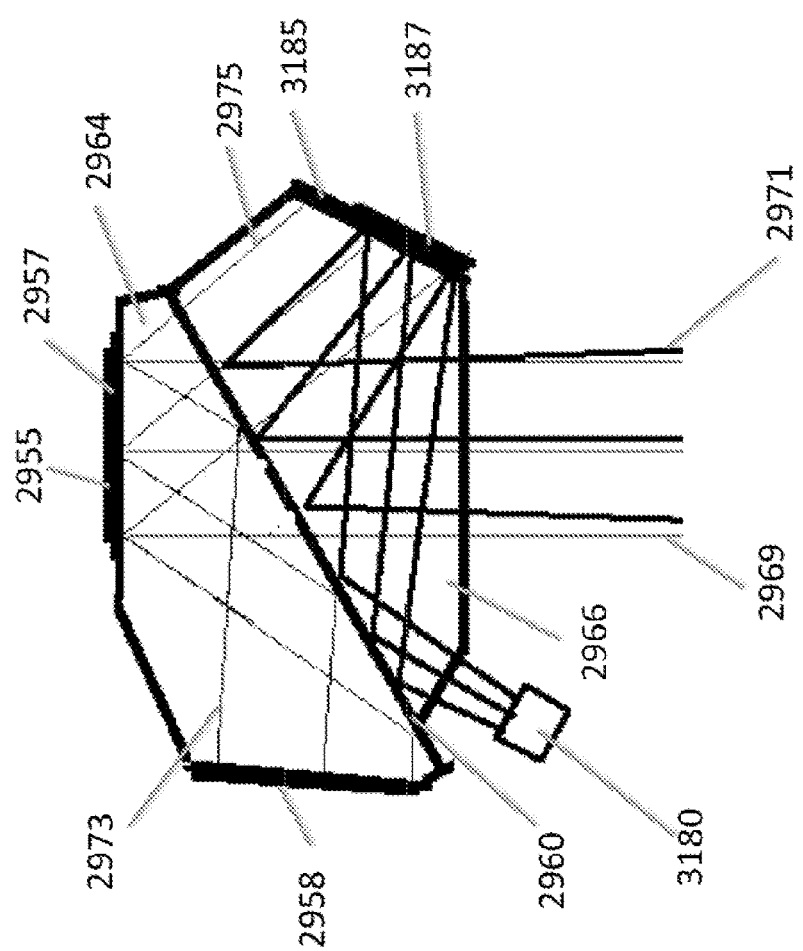

FIG. 31 shows an illustration of another embodiment of a system for displaying images and simultaneously capturing image of the wearer's eye that is similar to the one shown in FIG. 30. The difference in the system shown in FIG. 31 is that the light from the eye 2971 is subjected to multiple reflections before being captured by the camera 3180. To enable the multiple reflections, a mirror 3187 is provided behind the absorptive polarizer 3185. Therefore, the light from the eye 2971 is polarized prior to entering the corrective wedge 2966 with a polarization axis that is perpendicular to the transmission axis of the reflective polarizer that comprises the partially reflective layer 2960. In this way, the light from the eye 2971 is reflected first by the reflective polarizer, reflected second by the mirror 3187 and reflected third by the reflective polarizer before being captured by the camera 3180. While the light from the eye 2971 passes through the absorptive polarizer 3185 twice, since the polarization axis of the light from the eye 2971 is oriented parallel to the polarization axis of the light from the eye 2971, it is substantially transmitted by the absorptive polarizer 3185. As with the system described in connection with FIG. 30, the system shown in FIG. 31 includes an optically flat partially reflective layer 2960 that preserves the wavefront of the light from the eye 2971 so that higher quality images of the wearer's eye can be captured. Also, since the DLP 2955 is not included in the optical path for the light reflected from the eye 2971 and the eye imaging process shown in FIG. 31 does not interfere with the displayed image, images of the wearer's eye can be captured independently from the displayed images.

FIG. 32 shows an illustration of a system for displaying images and simultaneously capturing images of the wearer's eye that includes a beam splitter plate 3212 comprised of a reflective polarizer, which is held in air between the light source 2958, the DLP 2955 and the camera 3280. The illumination light 2973 and the light from the eye 2971 are both polarized with polarization axes that are perpendicular to the transmission axis of the reflective polarizer. As a result, both the illumination light 2973 and the light from the eye 2971 are substantially reflected by the reflective polarizer. The illumination light 2873 is reflected toward the DLP 2955 by the reflective polarizer and split into image light 2969 and dark light 3275 depending on whether the individual DLP mirrors are respectively in the "on" state or the "off" state. By passing through the quarter wave layer 2957 twice, the polarization state of the illumination light 2973 is reversed in comparison to the polarization state of the image light 2969 and the dark light 3275. As a result, the image light 2969 and the dark light 3275 are then substantially transmitted by the reflective polarizer. The absorptive polarizer 3285 at the side of the beam splitter plate 3212 has a transmission axis that is perpendicular to the polarization axis of the dark light 3275 and parallel to the polarization axis of the light from the eye 2971 so that the dark light 3275 is absorbed and the light from the eye 2971 is transmitted to the camera 3280. As in the system shown in FIG. 30, the system shown in FIG. 31 includes an optically flat beam splitter plate 3212 that preserves the wavefront of the light from the eye 2971 so that higher quality images of the wearer's eye can be captured. Also, since the DLP 2955 is not included in the optical path for the light from the eye 2971 and the eye imaging process shown in FIG. 31 does not interfere with the displayed image, images of the wearer's eye can be captured independently from the displayed images.

Eye imaging systems where the polarization state of the light from the eye 2971 needs to be opposite to that of the image light 2969 (as shown in FIGS. 30, 31 and 32), need to be used with lower modules 204 that include combiners that will reflect both polarization states. As such, these upper modules 202 are best suited for use with the lower modules 204 that include combiners that are reflective regardless of polarization state, examples of these lower modules are shown in FIGS. 6, 8*a*, 8*b*, 8*c* and 24-27.

Figure 33:
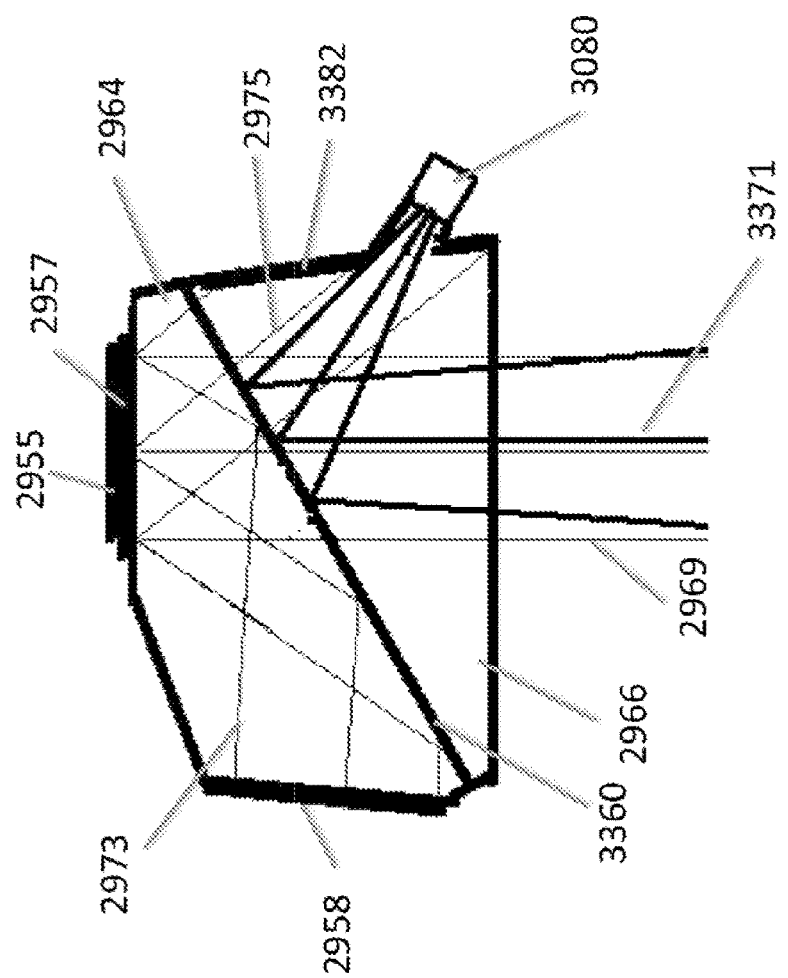

In a further embodiment shown in FIG. 33, the partially reflective layer 3360 is comprised of a reflective polarizer on the side facing the illumination light 2973 and a short pass dichroic mirror on the side facing the light from the eye 3371 and the camera 3080. Where the short pass dichroic mirror is a dielectric mirror coating that transmits visible light and reflects infrared light. The partially reflective layer 3360 can be comprised of a reflective polarizer bonded to the inner surface of the illumination wedge 2964 and a short pass dielectric mirror coating on the opposing inner surface of the corrective wedge 2966, wherein the illumination wedge 2964 and the corrective wedge 2966 are then optically bonded together. Alternatively, the partially reflective layer 3360 can be comprised of a thin substrate that has a reflective polarizer bonded to one side and a short pass dichroic mirror coating on the other side, where the partially reflective layer 3360 is then bonded between the illumination wedge 2964 and the corrective wedge 2966. In this embodiment, an infrared light is included to illuminate the eye so that the light from the eye and the images captured of the eye are substantially comprised of infrared light. The wavelength of the infrared light is then matched to the reflecting wavelength of the shortpass dichroic mirror and the wavelength that the camera can capture images, for example an 800 nm wavelength can be used. In this way, the short pass dichroic mirror transmits the image light and reflects the light from the eye. The camera 3080 is then positioned at the side of the corrective wedge 2966 in the area of the absorbing light trap 3382, which is provided to absorb the dark light 2975. By positioning the camera 3080 in a depression in the absorbing light trap 3382, scattering of the dark light 2975 by the camera 3080 can be reduced so that higher contrast images can be displayed to the wearer. An advantage of this embodiment is that the light from the eye need not be polarized, which can simplify the optical system and increase efficiency for the eye imaging system.

In yet another embodiment shown in FIG. 32*a* a beam splitter plate 3222 is comprised of a reflective polarizer on the side facing the illumination light 2973 and a short pass dichroic mirror on the side facing the light from the eye 3271 and the camera 3280. An absorbing surface 3295 is provided to trap the dark light 3275 and the camera 3280 is positioned in an opening in the absorbing surface 3295. In this way the system of FIG. 32 can be made to function with unpolarized light from the eye 3271.

Figure 34:
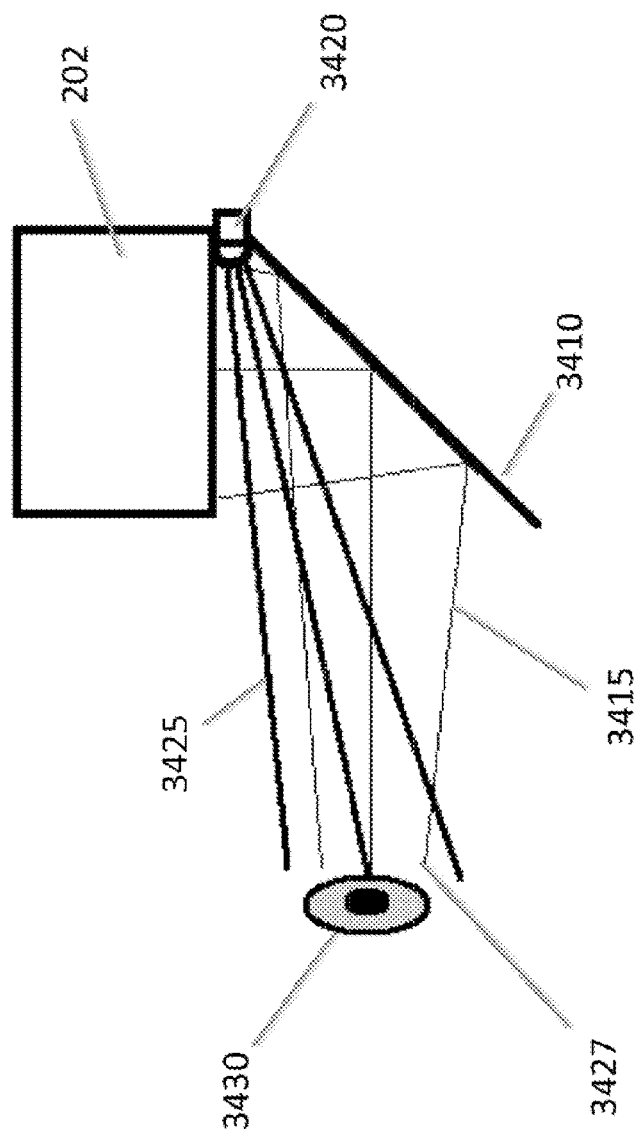
FIGS. 34 and 34a illustrate structured eye lighting systems according to the principles of the present invention.
Figure 34A:
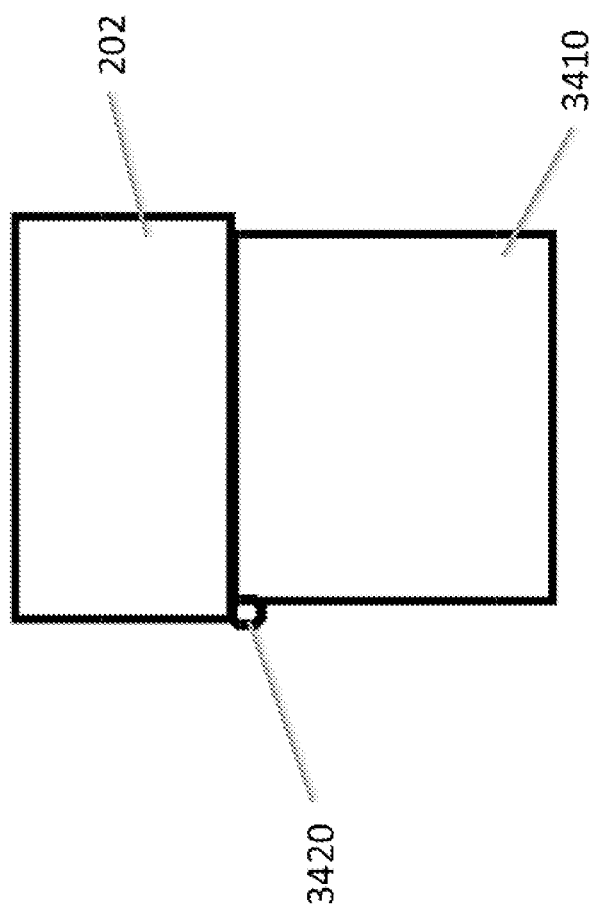

In embodiments directed to capturing images of the wearer's eye, light to illuminate the wearer's eye can be provided by several different sources including: light from the displayed image (i.e. image light); light from the environment that passes through the combiner or other optics; light provided by a dedicated eye light, etc. FIGS. 34 and 34*a* show illustrations of dedicated eye illumination lights 3420. FIG. 34 shows an illustration from a side view in which the dedicated illumination eye light 3420 is positioned at a corner of the combiner 3410 so that it doesn't interfere with the image light 3415. The dedicated eye illumination light 3420 is pointed so that the eye illumination light 3425 illuminates the eyebox 3427 where the eye 3430 is located when the wearer is viewing displayed images provided by the image light 3415. FIG. 34*a* shows an illustration from the perspective of the eye of the wearer to show how the dedicated eye illumination light 3420 is positioned at the corner of the combiner 3410. While the dedicated eye illumination light 3420 is shown at the upper left corner of the combiner 3410, other positions along one of the edges of the combiner 3410, or other optical or mechanical components, are possible as well. In other embodiments, more than one dedicated eye light 3420 with different positions can be used. In an embodiment, the dedicated eye light 3420 is an infrared light that is not visible by the wearer (e.g. 800 nm) so that the eye illumination light 3425 doesn't interfere with the displayed image perceived by the wearer.

Figure 35:
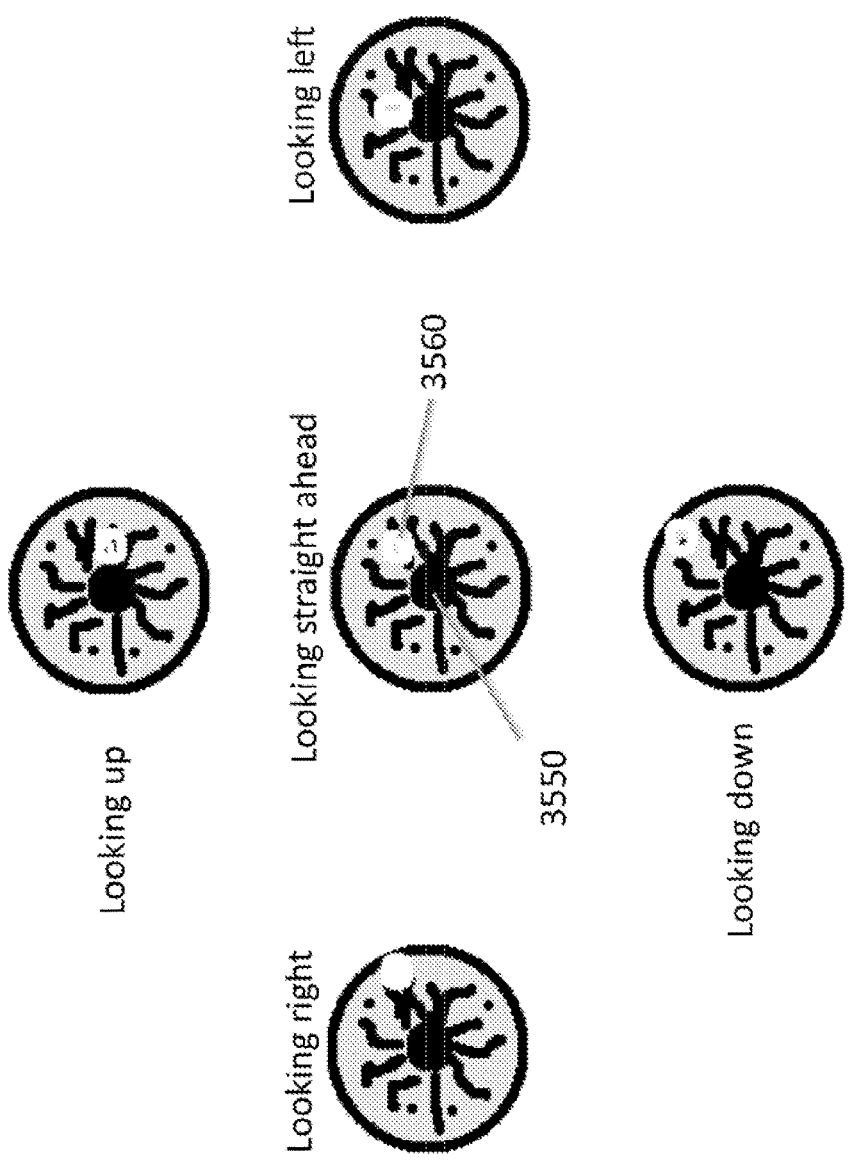
FIG. 35 illustrates eye glint in the prediction of eye direction analysis in accordance with the principles of the present invention.

FIG. 35 shows a series of illustrations of captured eye images that show the eye glint (i.e. light that reflects off the front of the eye) produced by a dedicated eye light. In this embodiment of the invention, captured images of the wearer's eye are analyzed to determine the relative positions of the iris 3550, pupil, or other portion of the eye, and the eye glint 3560. The eye glint is a reflected image of the dedicated eye light 3420 when the dedicated light is used. FIG. 35 illustrates the relative positions of the iris 3550 and the eye glint 3560 for a variety of eye positions. By providing a dedicated eye light 3420 in a fixed position, combined with the fact that the human eye is essentially spherical, or at least a reliably repeatable shape, the eye glint provides a fixed reference point against which the determined position of the iris can be compared to determine where the wearer is looking, either within the displayed image or within the see-through view of the surrounding environment. By positioning the dedicated eye light 3420 at a corner of the combiner 3410, the eye glint 3560 is formed away from the iris 3550 in the captured images. As a result, the positions of the iris and the eye glint can be determined more easily and more accurately during the analysis of the captured images, since they do not interfere with one another. In a further embodiment, the combiner includes an associated cut filter that prevents infrared light from the environment from entering the HWC and the camera is an infrared camera, so that the eye glint is only provided by light from the dedicated eye light. For example, the combiner can include a low pass filter that passes visible light while absorbing infrared light and the camera can include a high pass filter that absorbs visible light while passing infrared light.

In an embodiment of the eye imaging system, the lens for the camera is designed to take into account the optics associated with the upper module 202 and the lower module

204. This is accomplished by designing the camera to include the optics in the upper module 202 and optics in the lower module 204, so that a high MTF image is produced, at the image sensor in the camera, of the wearer's eye. In yet a further embodiment, the camera lens is provided with a large depth of field to eliminate the need for focusing the camera to enable sharp image of the eye to be captured. Where a large depth of field is typically provided by a high f/# lens (e.g. f/#>5). In this case, the reduced light gathering associated with high f/# lenses is compensated by the inclusion of a dedicated eye light to enable a bright image of the eye to be captured. Further, the brightness of the dedicated eye light can be modulated and synchronized with the capture of eye images so that the dedicated eye light has a reduced duty cycle and the brightness of infrared light on the wearer's eye is reduced.

In a further embodiment, FIG. 36*a* shows an illustration of an eye image that is used to identify the wearer of the HWC. In this case, an image of the wearer's eye 3611 is captured and analyzed for patterns of identifiable features 3612. The patterns are then compared to a database of eye images to determine the identity of the wearer. After the identity of the wearer has been verified, the operating mode of the HWC and the types of images, applications, and information to be displayed, can be adjusted and controlled in correspondence to the determined identity of the wearer. Examples of adjustments to the operating mode depending on who the wearer is determined to be or not be include: making different operating modes or feature sets available, shutting down or sending a message to an external network, allowing guest features and applications to run, etc.

FIG. 36*b* is an illustration of another embodiment using eye imaging, in which the sharpness of the displayed image is determined based on the eye glint produced by the reflection of the displayed image from the wearer's eye surface. By capturing images of the wearer's eye 3611, an eye glint 3622, which is a small version of the displayed image can be captured and analyzed for sharpness. If the displayed image is determined to not be sharp, then an automated adjustment to the focus of the HWC optics can be performed to improve the sharpness. This ability to perform a measurement of the sharpness of a displayed image at the surface of the wearer's eye can provide a very accurate measurement of image quality. Having the ability to measure and automatically adjust the focus of displayed images can be very useful in augmented reality imaging where the focus distance of the displayed image can be varied in response to changes in the environment or changes in the method of use by the wearer.

Although embodiments of HWC have been described in language specific to features, systems, computer processes and/or methods, the appended claims are not necessarily limited to the specific features, systems, computer processes and/or methods described. Rather, the specific features, systems, computer processes and/or and methods are disclosed as non-limited example implementations of HWC. All documents referenced herein are hereby incorporated by reference.

I claim:

1. An image source for a head-worn display, comprising:
   a digital light processing (DLP) display positioned to reflect on-pixel light in-line with transfer optics adapted to present the on-pixel light to an eye of a user as image light, the DLP display further positioned to reflect off-pixel light in-line with a dark light trap; and
   a camera positioned to capture eye-image light originating as a reflection from the eye of the user, wherein, prior to being captured by the camera, the eye-image light reflects off of a plurality of mirrors of the DLP display and then off of a reflective surface positioned to reflect the eye-image light towards the camera.

2. The image source of claim 1, wherein the eye-image light is reflected off of off-pixel mirrors of the DLP display.

3. The image source of claim 1, wherein the eye-image light is reflected off of no-power-pixel mirrors of the DLP display.

4. The image source of claim 1, wherein the reflective surface is a partially reflective and partially transmissive surface.

5. The image source of claim 4, wherein the reflection and transmission properties are polarization dependent.

6. The image source of claim 1, wherein the eye-image light is captured by the camera simultaneously with image light being transferred to the eye of the user.

7. The image source of claim 1, wherein a subset of mirrors of the DLP display are dedicated to reflect eye-image light.

* * * * *